United States Patent
Miller

(12) 
(10) Patent No.: US 6,218,106 B1
(45) Date of Patent: *Apr. 17, 2001

(54) RESTRICTION FRAGMENT LENGTH POLYMORPHISM TEST FOR HAPLOTYPING DOMESTICATED FOWL

(75) Inventor: Marcia M. Miller, Altadena, CA (US)

(73) Assignee: City of Hope, Duarte, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/374,219

(22) Filed: Jan. 18, 1995

Related U.S. Application Data

(62) Division of application No. 07/865,662, filed on Apr. 7, 1992, now Pat. No. 5,451,670, which is a continuation of application No. 07/688,326, filed on Apr. 22, 1991, now abandoned, which is a continuation-in-part of application No. 07/588,922, filed on Sep. 27, 1990, now abandoned, which is a continuation-in-part of application No. 07/210,405, filed on Jun. 23, 1988, now abandoned, which is a continuation-in-part of application No. 07/130,529, filed on Dec. 9, 1987, now abandoned, which is a continuation-in-part of application No. 07/068,176, filed on Jun. 30, 1987, now abandoned, which is a continuation-in-part of application No. 07/413,301, filed on Sep. 28, 1989, now abandoned.

(51) Int. Cl.$^7$ .............................. C12Q 1/68; C07H 21/04
(52) U.S. Cl. ................................ 435/6; 536/24.31; 536/27
(58) Field of Search ..................... 435/6, 183; 536/24.31, 536/27

(56) References Cited

U.S. PATENT DOCUMENTS 4,988,617   1/1991   Landegren et al. .

OTHER PUBLICATIONS

*Nucleic Acid Hybridisation, A Practical Approach*, Eds. B.D. Hames and S.J. Higgins, IRL Press, Washington, D.C. (1985) (Table of Contents only).

*Primary Examiner*—Bradley L. Sisson
(74) *Attorney, Agent, or Firm*—Rothwell, Figg, Ernst & Manbeck, P.C.

(57) ABSTRACT

The major histocompatibility complex (MHC) of domesticated fowl, the B system, is known to contain three subregions which are identified as B-F, B-G and B-L. This invention includes a cDNA clone encoding a B-G antigen of the B system. MHC haplotyping is accomplished by use of novel probes provided by clones to detect restriction fragment length polymorphism (RFLP) patterns typical for various B-G subregion alleles.

Additional information concerning this invention is set forth in the attached manuscript entitled "Hypervariable sequence diversity in Ig V-like and leucine heptad domains in chicken histocompatibility B-G antigens".

4 Claims, 37 Drawing Sheets

| | |
|---|---|
| GAC ATC AGA TGG ATC CAG CAG CGG TCC TCT CGG CTT GTG CAC CAC TAC<br>Asp Ile Arg Trp Ile Gln Gln Arg Ser Ser Arg Leu Val His His Tyr<br>1                    5                             10                          15 | 48 |
| CGA AAT GGA GTG GAC CTG GGG CAC ATG GAG GAA TAT AAA GGG AGA ACA<br>Arg Asn Gly Val Asp Leu Gly His Met Glu Glu Tyr Lys Gly Arg Thr<br>                    20                            25                          30 | 96 |
| GAA CTG CTC AGG GAT GGT CTC TCT GAT GGA AAC CTG GAT TTG CGC ATC<br>Glu Leu Leu Arg Asp Gly Leu Ser Asp Gly Asn Leu Asp Leu Arg Ile<br>          35                          40                            45 | 144 |
| ACT GCT GTG ACC TCC TCT GAT AGT GGC TCC TAC AGC TGT GCT GTG CAA<br>Thr Ala Val Thr Ser Ser Asp Ser Gly Ser Tyr Ser Cys Ala Val Gln<br>    50                            55                        60 | 192 |
| GAT GGT GAT GCC TAT GCA GAA GCT GTG GTG AAC CTG GAG GTG TCA GAC<br>Asp Gly Asp Ala Tyr Ala Glu Ala Val Val Asn Leu Glu Val Ser Asp<br>65                    70                        75                        80 | 240 |
| CCC TTT TCT ATG ATC ATC ATC CTT TAC TGG ACA GTG GCT CTG GCT GTG<br>Pro Phe Ser Met Ile Ile Ile Leu Tyr Trp Thr Val Ala Leu Ala Val<br>                        85                          90                          95 | 288 |
| ATC ATC ACA CTT CTG GTT GGG TCA TTT GTC GTC AAT GTT TTT CTC CAT<br>Ile Ile Thr Leu Leu Val Gly Ser Phe Val Val Asn Val Phe Leu His<br>          100                        105                        110 | 336 |
| AGA AAG AAA GTG GCA CAA GAG CAG AGA GCT GAA GAG AAA AGA TGC AGA<br>Arg Lys Lys Val Ala Gln Glu Gln Arg Ala Glu Glu Lys Arg Cys Arg<br>          115                        120                        125 | 384 |
| GTT GGT GGA GAA AGC TGC AGC ATT GGA GAG AAA AGA TGC AGA GTT GGC<br>Val Gly Gly Glu Ser Cys Ser Ile Gly Glu Lys Arg Cys Arg Val Gly<br>          130                        135                        140 | 432 |
| GGA ACA AGC AGC GCA ATC GAA GCA AAG AGA TGC AAT GTT GGA CAA ACA<br>Gly Thr Ser Ser Ala Ile Glu Ala Lys Arg Cys Asn Val Gly Gln Thr<br>145                    150                        155                        160 | 480 |
| CGT TCT AAA CTG GAG GAA AGA CAG AGC AAG TGG AGA TTG GAA TTC<br>Arg Ser Lys Leu Glu Glu Arg Gln Ser Lys Trp Arg Leu Glu Phe<br>                  165                        170                        175 | 525 |

FIG. 6

CLONE bg28

```
GACATCAGAT GGATCCAGCA GCGGTCCTCT CGGCTTGTGC ACCACTACCG AAATGGAGTG      60
GACCTGGGGC AGATGGAGGA ATATAAAGGG AGAACAGAAC TGCTCAGGGA TGGTCTCTCT     120
GATGGAAACC TGGATTTGCG CATCACTGCT GTGACCTCCT CTGATAGTGG CTCCTACAGC     180
TGTGCTGTGC AAGATGGTGA TGCCTATGCA GAAGCTGTGG TGAACCTGGA GGTGTCAGAC     240
CCCTTTTCTA TGATCATCCT TTACTGGACA GTGGCTCTGG CTGTGATCAT CACACTTCTG     300
GTTGGGTCAT TTGTCGTCAA TGTTTTTCTC CATAGAAAGA AAGTGGCACA GAGCAGAGAG     360
CTGAAGAGAA AAGATGCAGA GTTGGTGGAG AAAGCTGCAG CATTGGAGAG AAAAGATGCA     420
GAGTTGGCGG AACAAGCAGC GCAATCGAAG CAAAGAGATG CAATGTTGGA CAAACACGTT     480
CTAAAACTGG AGGAAAAGAC AGACGAAGTG GAGATTGGAA TTC                       523
```

FIG. 7

CLONE bg32.1

```
CGGTGAACAG ATGGAGAGAA GGAATGCAAA GTTGGAGGCA GCAGCTGTAA AACTGGGACA      60
CAAAGCTAAA GAATCAGAGA AACAGAAATC GGAGCTGAAG GAGCGCCATG AGGAGATGGC     120
AGAACAAACT GAAGCAGTGG TGGTAGAAAC TGAAGAATAG GAAAAACCAT CTGAAGAATC     180
AGATTGAGAG ATGAACTGCG CCTCACAATA AGCACAGGAG TTAAGCTTCT TAGATCAATA     240
ACTGCACAGC ATACAAAACC ACAATAACTC AAACAGAGTA AGGAGGAGCC AGTGTTTGTG     300
TTGAGTGAGA ACACTGCAGT TCTGTCAGCC AAAGCTGCCT GAGGGACCGC CCAATTGAGG     360
GTGTGTGACC TCCAACTCAA ATCCAGTTGG AAGAAAGAAA CCATAGAAAG GAAGGAAAGG     420
GGAGGAAGAC AGAGATCCTG GAAGAGATAT GGGCATTTGG GGAAATAGTG TGATCATGTA     480
TCAGGCTTTG TGGACATCTA ATGAATATGT CATGCTTTTG TAACTACAAG CATGCACGCA     540
GAAACAAAGG TAGAAAACTG CTTTGGGTGT TAGCACTGTT CTCTGTCACT ATATAATAAA     600
GAATACCTGC TGATGGCAAT GGAACAAAAA AAAA                                 634
```

FIG. 11

```
ATCCGTTCGA GCTCTCTCCT CCTACAGCTG CTGCCCTCAT ATTCTCCCCA CACTTCTTCC      60
CCATATTCTT TCCAAATCCT CTTCCCCATC TCCTCCACCG TCTCTTTCTC AGAGTCCTTC     120
CTCTCTCTCC CTAAATTCTT CCCCCCTCCT CTCCTCCAGC ACAGATGCGC TTCACATCGG     180
GATGCAACCA CCCCAGTTTC ACCCTCCCCT GGAGGACCCT CCTGCCTTAT CTCGTGGCTC     240
TGCACCTCCT CCAGCCGGGA TCAGCCCAGC TCAGGGTGGT GGCGCCGAGC CTCCGTGTCA     300
CTGCCATCGT GGGACAGGAT GTCGTGCTGC GCTGCCACTT GTGCCCTTGC AAGGATGCTT     360
GGAGATTGGA CATCAGATGG ATCCTGCAGC GGTCCTCTGG TTTTGTGCAC CACTATCAAA     420
ATGGAGTGGA CCTTGGGCAG ATGGAGGGAT ATAAAGGGAG AACAGAACTG CTCAGGGATG     480
GTCTCTATGA TGGAAACCTG GATTTGCGCA TCACTGCTGT GAGCACCTCC GATAGTGGCT     540
CATACAGCTG TGCTGTGCAG GATGGTGATG GCTATGCAGA CGCTGTGGTG GACCTGGAGG     600
TGTCAGATCC CTTTTCCCAG ATCGTCCATC CCTGGAAGGT GGCTCTGGCT GTGGTCGTCA     660
CAATTCTCGT TGGGTCATTT GTCATCAATG TTTTTCTCTG TAGGAAGAAA GCGGCACAGA     720
GCAGAGAGCT GAGTGAGTCC TTCCAGCCCC TTCCACCACC AAAGTCCCTT TAATGGAACT     780
GATAGAAGAC TGCAGAGTGC TGGGTTTATG CCTTGTGCTG GGCCATGGG ATCTATGGGA      840
CCTTGGGATG TGTTGGGGCC GTGGGATGTG CTGGGGTCGT GGGATCTGTC AACCCTGATT     900
GATCCACTTC AGAACTCTTG CCCAATCGGT TCCTTCCGAT TCATTTAACT CCTTCTTGAG     960
GCCAAAGTGG TCATTGGCCA CATCCCATAA AAAGGGTTT GGGGTCAGGG TGTGGGAGCT     1020
GATCGCATGG AAACGTGTCC CCTCTGACCA TGCATTTCAT TTGCTTCTAT TTTGCAGAGA    1080
GAAAAGATGC AGCGTTGGCG GAACTAGATG AGATATCGGG TTTAAGTGCT GAAAATCTGA    1140
AGCAATTAGC TTCAAAACTG AACGAAAATG CTGACGAAGT GGAGGATTGC AATTCAGAGC    1200
TGAAGAAAGA CTGTGAAGAG ATGGGTTCTG GCGTTGGAGA TCTGAAGGAA CTGGCTGCAA    1260
AATTGGAGGA ATATATTGCA GTGAATCGGA GAAGGAATGT AAAGTTGAAT AATATAGCTG    1320
CCAAACTGGC ACAACAAACT AAAGAATTGG AGAAACAGCA TTCACAGTTC ACAGACACT     1380
TTCAGCGTAT GGATTTAAGT GCTGTAAACC AGAAGAAACT GGTTACAAAA CTGGAGGAAC    1440
ACTTTGAATG GATGGAGAGA AGGAATGTAA AGTTGGAGAT ACCAGCTGTA ATACTGGGGC    1500
AACAAGCTAA AGAATCAGAG AAACAGAAAT CGGAGCTGAA GGAGCGCCAT GAGGAGATGG    1560
CAGAACAAAC TGAAGCAGTG GTGGTAGATA CTGAAGAAGC GGAAAAACCA TCTGAAGAAT    1620
TGGATTGAGA GATGAACTGC GCCTCACAGT AACCACAGGA GTTAAGCTTC ATAGATCAAT    1680
GACTGCACAG CATACAAAAA CCACGATACC TCAAACAGAG CAAGGAAATC CACAGCGAGA    1740
ACAAGAGGAG CCAGTGTTTG TGTTGAGTGA GAACACTGCA GTTCT                    1785
```

FIG. 12

```
TTCTGCCCTC ATATTCTCCC CACACTTCTT CCCCATATTC TTTCCAAATC CTCTTCCCCA      60
TCTCCTCCAT CGTCTCCTTC TCAGAGTCCT TCCTCTCTCT CCCTAAATTC TTCCCCCCTC     120
CTCTTCTCCA GCACAGATGG CCTTCACATC GGGCTGCAAC CACCCCAGTT TCACCCTCCC     180
CTGGAGGACC CTCCTGCCTT ATCTCGTGGC TCTGCACCTC CTCCAGCCGG GATCAGCCCA     240
GATCACGGTG GTGGCACCGA GCCTCCGTGT CACTGCCATC GTGGGACAGG ATGTTGTGCT     300
GCGCTGCCAC TTGTCCCCAT GCAAGGATGT TCGGAATTCA GACATCAGAT GGATCCAGCA     360
GCGGTCCTCT CGGCTTGTGC ACCACTACCG AAATGGAGTG GACCTGGGGC AGATGGAGGA     420
ATATAAAGGG AGAACAGAAC TGCTCAGGGA TGGTCTCTCT GATGGAAACC TGGATTTGCG     480
CATCACTGCT GTGACCTCCT CTGATAGTGG CTCCTACAGC TGTGCTGTGC AAGATGGTGA     540
TGCCTATGCA GAAGCTGTGG TGAACCTGGA GGTGTCAGAC CCCTTTTCTA TGATCATCCT     600
TTACTGGACA GTGGCTCTGG CTGTGATCAT CACACTTCTG GTTGGGTCAT TTGTCGTCAA     660
TGTTTTTCTC CATAGAAAGA AGTGGCACA GAGCAGAGAG CTGAAGAGAA AGATGCAGA      720
GTTGGTGGAG AAAGCTGCAG CATTGGAGAG AAAAGATGCA GAGTTGGCGG AACAAGCAGC     780
GCAATCGAAG CAAAGAGATG CAATGTTGGA CAAACACGTT CTAAAACTGG AGGAAAAGAC     840
AGACGAAGTG GAGAACTGGA ATTCAGTGCT GAAAAAGAC AGTGAAGAGA TGGGTTATGG      900
CTTTGGAGAT CTGAAGAAAC TGGCTGCAGA ACTGGAGAAA CACTCTGAAG AGATGGGGAC     960
AAGGGATTTA AAGTTGGAGC GACTAGCTGC CAAACTGGAA CATCAAACTA AGAATTGGA     1020
GAAACAGCAT TCACAGTTCC AGAGACACTT TCAGAATATG TATTTAAGTG CTGGAAAACA    1080
GAAGAAAATG GTTACAAAAC TGGAGGAACA CTGTGAATGG ATGGTGAGAA GGAATGTAAA    1140
GTTGGAGATA CCAGCTGTAA AAGTGGGGCA ACAAGCTAAA GAATCAGAGG AACAGAAATC    1200
GGAGCTGAAG GAGCACCATG AGGAGACGGG GCAACAAGCT AAAGAATCAG AGAAACAGAA    1260
ATCGGAGCTG AAGGAGCGCC ATGAGGAGAT GGCAGAACAA ACTGAAGCAG TGGTGGTAGA    1320
AACTGAAGAA TAGGAAAAAC CATCTGAAGA ATTGGATTGA GAGATGAACT GCGCCTCGCA    1380
GTAACCACAG GAGTTAAGCT TCATAGATCA ATAACTGCAC AGCATACAAA ACCACAATAA    1440
CTCAAACAGG GTAAGGAGGA GCCAGTGTTT GTGTTGAGTG AGAACACTGC AGTTCTGTCA    1500
GCCAAAGCTG CCTGAGGGAC CGCCCAATTG AGGGTGTGCG ACCTCCAACT CAAAGCCAAT    1560
```

FIG. 13A

```
TGGAAGAAAG AAACCATAGA AAGGAAGAAA AGGGGAGGAA GACAGAGATC CTGGAAGAGA    1620

TATGGGCATT TGGGGAAATA GTGTGACCAT GTATCAGGCT TTGTGGACAT CTAACGAATA    1680

TGTCATGTTT TTGTAAATAC AAGCATGCAC GCAGAAACAA AGGGAGAAAA CTGCTTTGGG    1740

TGTTAGCACT GTTCTCTGTC CCTATATAAT AAAGAATACC TGCTGATGGC AAAAAAAAAA    1800

AAAAAAAAAA AAAAAA                                                    1816
```

FIG. 13B

```
AAATGAAGAC TTCAGGATCC TTCCATAAAA GCTATCAGTT TGACTTCAGA GAGGGCTATT      60
CTCGGTGTTT GCAAGAAGCT TTCCATCGTC TCCTTCTCAG AGTCCTTCCT CTCTCTCCCT     120
AAATTCTTCC CCCCTCCTCT TCTCCAGCAC AGATGGCCTT CACATCGGGC TGCAACCACC     180
CCAGTTTCAC CCTCCCCTGG AGGACCCTCC TGCCTTATCT CGTGGCTCTG CACCTCCTCC     240
AGCCGGGATC AGCCCAGATC ACGGTGGTGG CACCGAGCCT CCGTGTCACT GCCATCGTGG     300
GACAGGATGT TGTGCTGCGC TGCCACTTGT CCCCATGCAA GGATGTTCGG AATTCAGACA     360
TCAGATGGAT CCAGCAGCGG TCCTCTCGGC TTGTGCACCA CTACCGAAAT GGAGTGGACC     420
TGGGGCAGAT GGAGGAATAT AAAGGGAGAA CAGAACTGCT CAGGGATGGT CTCTCTGATG     480
GAAACCTGGA TTTGCGCATC ACTGCTGTGA CCTCCTCTGA TAGTGGCTCC TACAGCTGTG     540
CTGTGCAAGA TGGTGATGCC TATGCAGAAG CTGTGGTGAA CCTGGAGGTG TCAGACCCCT     600
TTTCTATGAT CATCCTTTAC TGGACAGTGG CTCTGGCTGT GATCATCACA CTTCTGGTTG     660
GGTCATTTGT CGTCAATGTT TTTCTCCATA GAAAGAAAGT GGCACAGAGC AGAGAGCTGA     720
AGAGAAAAGA TGCAGAGTTG GTGGAGAAAG CTGCAGCATT GGAGAGAAAA GATGCAGAGT     780
TGGCGGAACA AGCAGCGCAA TCGAAGCAAA GAGATGCAAT GTTGGACAAA CACGTTCTAA     840
AACTGGAGGA AAAGACAGAC GAAGTGGAGA ATTGGAATTC AGTGCTGAAA AAGACAGTG     900
AAGAGATGGG TTATGGCTTT GGAGATCTGA AGAAACTGGC TGCAGAACTG GAGAAACACT     960
CTGAAGAGAT GGGGACAAGG GATTTAAAGT TGGAGCGACT AGCTGCCAAA CTGGAACATC    1020
AAACTAAAGA ATTGGAGAAA CAGCATTCAC AGTTCCAGAG ACACTTTCAG AATATGTATT    1080
TAAGTGCTGG AAAACAGAAG AAAATGGTTA CAAAACTGGA GGAACACTGT GAATGGATGG    1140
TGAGAAGGAA TGTAAAGTTG GAGATACCAG CTGTAAAAGT GGGGCAACAA GCTAAAGAAT    1200
CAGAGGAACA GAAATCGGAG CTGAAGGAGC ACCATGAGGA GACGGGGCAA CAAGCTAAAG    1260
AATCAGAGAA ACAGAAATCG GAGCTGAAGG AGCGCCATGA GGAGATGGAA CAAACTGAAG    1320
CAGTGGTGGT AGAAACTGAA GAATAGGAAA AACCATCTGA GAATTGGAT TGAGAGATGA    1380
ACTGCGCCTC GCAGTAACCA CAGGAGTTAA GCTTCATAGA TCAATAACTG CACAGCATAC    1440
AAAATCACAA TAACTCAAAC AGGGTAAGGA GGAGCCAGTG TTTGTGTTGA GTGAGAACAC    1500
TGCAGTTCTG TCAGCCAAAG CTGCCTGAGG GACCGCCCAA TTGAGGGTGT GCGACCTCCA    1560
```

FIG. 14A

```
ACTCAAAGCC AATTGGAAGA AAGAAACCAT AGAAAGGAAG AAAAGGGGAG GAAGACAGAG    1620
ATCCTGGAAG AGATATGGGC ATTTGGGGAA ATAGTGTGAC CATGTATCAG GCTTTGTGGA    1680
CATCTAACGA ATATGTCATG TTTTTGTAAA TACAAGCATG CACGCAGAAA CAAAGGGAGA    1740
AAACTGCTTT GGGTGTTAGC ACTGTTCTCT GTCCCTATAT AATAAAGAAT ACCTGCTGAT    1800
GGCAATGGAA AAAAAAAAA AA                                              1822
```

FIG. 14B

```
ATCCGCTCGA GCTCTCTCCT CCTACAGTTT CTGCCCTCAT ATTCTCCCCA CACTTCTTCC    60
CCATATTCTT TCCAAATCCT CTTCCCCATC TCCTCCATCG TCTCCTTCTC AGAGTCCTTC   120
CTCTCTCTCC CTAAATTCTT CCCCCCTCCT CTTCTCCAGC ACAGATGGCC TTCACATCGG   180
GCTGCAACCA CCCCAGTTTC ACCCTCCCCT GGAGGACCCT CCTGCCTTAT CTCGTGGCTC   240
TGCACCTCCT CCAGCCGGGA TCAGCCCAGA TCACGGTGGT GGCACCGAGC CTCCGTGTCA   300
CTGCCATCGT GGGACAGGAT GTTGTGCTGC GCTGCCACTT GTCCCCATGC AAGGATGTTC   360
GGAATTCAGA CATCAGATGG ATCCAGCAGC GGTCCTCTCG GCTTGTGCAC CACTACCGAA   420
ATGGAGTGGA CCTGGGGCAG ATGGAGGAAT ATAAAGGGAG AACAGAACTG CTCAGGGATG   480
GTCTCTCTGA TGGAAACCTG GATTTGCGCA TCACTGCTGT GACCTCCTCT GATAGTGGCT   540
CCTACAGCTG TGCTGTGCAA GATGGTGATG CCTATGCAGA AGCTGTGGTG AACCTGGAGG   600
TGTCAGACCC CTTTTCTATG ATCATCCTTT ACTGGACAGT GGCTCTGGCT GTGATCATCA   660
CACTTCTGGT TGGGTCATTT GTCGTCAATG TTTTTCTCCA TAGAAAGAAA GTGGCACAGA   720
GCAGAGAGCT GAGTGAGTCC TTCCATCCCC ATCCACCAAC CAAAGTCCCT TTAATGGAAC   780
TGACAGCAGA CTGCAGAGTG CTGGGTTATG CCATGTGCTG GGGCCATGAG CTATGTTGAG   840
GCTTTGGAAT GTGTTGGGGT TGTGGGATGT ACTGGGGTCG TGGGATGTGT TATTCCTGGC   900
TGATTCACGT GGAAAAACCT TTCACAATCG GTTCCTTCCA GTTTGTTTAA TTCCTTCTTG   960
GGCCCAAAGT GGTCATTGGA CTCCTCCCAG AAAAAAGGGT TTGGGGTCAG GGTGTGAGAG  1020
CTGATGGCAC GGAAACGTGT CCCCTCTGAC CATGCATTTC ATTTGCTTCT ATTTTGCAGA  1080
GAGAAAAGAT GCAGAGTTGG GTAAGTCTCC TTCCCTAAAG CGAGGGAATT CAGGGTGTCC  1140
CCATGGCATC AGCCGTGGAA TTAGTAGCTG TCCTCTCTGA CAATTCACTG CTCTGCTCTT  1200
TCCTTTCCAG TGGAGAAAGC TGCAGCATTG GGTGAGTTAT ATTCCCCAAG CCAAAGTACT  1260
TTGGGTCTTC CCATTGGAAG TTATTTCCTC AGACCATCCT TTCTGTTGTG TTTGCTTTGG  1320
CATCATGTTA GTAAAATGCC TTCTTGGGAC CAAAGTGGTC ATTGGCCACT TCCCAGAAAA  1380
AAAGGTTTGG GGTCAGGGTG TGGGAGCTGA TGGCATGGAA ACATGTTCCC TCTGACCATG  1440
CATTTCCTTT GCTTCTTTTT CCAGAGAGAA AAGATGCAGA GTTGGCGGAA CAAGCAGCGC  1500
AATCGAGTGA GTCTCCCCCT CCATTTTTAT TATTTTTAAA TGTTCAGCCT CCGGTAGCTG  1560
```

FIG. 15A

```
TGGGATGAGA TGTTCCTCTC ATCATACACT GACTCTGCTT TTCCTTTGCA GAGCAAAGAG    1620
ATGCAATGTT GGACAAACAC GTTCTAAAAC TGGGTGAGTC CTCACTCCCA AATTATAAAG    1680
CAAAGGGTTC TGCCTGTGTG AGCTGTGGGA TCAGACGTTC CTCTCATCGT GCATTGCTTT    1740
TCTCTTTCTT TTTCAGAGGA AAAGACAGAC GAAGTGGAGA ATTGGAATTC AGTGCTGAGT    1800
AAGTTGCAGT CACTGAACTG AGGGAATGTG GGGTCTTCCT AAGGGACTGC GTAGGGGAGA    1860
AGTTCCCATG CACTGCTTTT CTCTTTCTTT TCCAGAAAAA GACAGTGAAG AGATGGGTTA    1920
TGGCTTTGGA GATCTGAGTA AGTCTCCCTC CCAACATGGA AGGAATTTAT GGTCTTAGCA    1980
TGGGATCAGC CATGGGATGA TCATCTGACC CCTCTCATCA TGCAATTCAT ATTTGTTCCT    2040
TTTGCAGAGA AACTGGCTGC AGAACTGGAG AAACACTCTG AAGAGATGGG GACAAGGGAT    2100
TTAAAGTTGG AGCGACTAGC TGCCAAACTG GAACATCAAA CTAAAGAATT GGAGAAACAG    2160
CATTCACAGT TCCAGAGACA CTTTCAGAAT ATGTATTTAA GTGCTGGAAA ACAGAGTAAG    2220
TCTCCCTCCC TGCACAGAAG GAACTTACGG TTTTCCCATG GGATCAGCCA TGGGACGATC    2280
ATCCGACTCT TCTCATCATG AATTTCGTCT TTCTTTCTTT TGCAGAGAAA ATGGTTACAA    2340
AACTGGAGGA ACACTGTGAA TGGATGGTGA GAAGGAATGT AAAGTTGGAG ATACCAGCTG    2400
TAAAAGTGGG GCAACAAGCT AAAGAATCAG AGGAACAGAA ATCGGAGCTG AAGGAGCACC    2460
ATGAGGAGAC GGGGCAACAA GCTAAAGAAT CAGAGAAACA GAAATCGGAG CTGAAGGAGC    2520
GCCATGAGGA GATGGCAGAA CAAACTGAAG CAGTGGTGGT AGAAACTGAA GAATAGGGTG    2580
AGTCTTTCCC AAACCAAAGC AATACGGGGT TTCCCATGGC ATGACAAGCT GTCCCACCTC    2640
AGCATCCGTT CCTTTTTCTT TCTTTTCCAG AAAAACCATC TGAAGAATTG GATTGAGAGA    2700
TGAACTGCGC CTCGCAGTAA CCACAGGAGT TAAGCTTCAT AGATCAATAA CTGCACAGCA    2760
TACAAAACCA CAATAACTCA ACAGGGTAA GGAGGAGCCA GTGTTTGTGT TGAGTGAGAA    2820
CACTGCAGTT CTGTCAGCCA AAGCTGCCTG AGGGACCGCC CAATTGAGGG TGTGCGACCT    2880
CCAACTCAAA GCCAATTGGA AGAAAGAAAC CATAGAAAGG AAGAAAAGGG GAGGAAGACA    2940
GAGATCCTGG AAGAGATATG GGCATTTGGG GAAATAGTGT GACCATGTAT CAGGCTTTGT    3000
GGACATCTAA CGAATATGTC ATGTTTTTGT AAATACAAGC ATGCACGCAG AAACAAAGGG    3060
AGAAAACTGC TTTGGGTGTT AGCACTGTTC TCTGTCCCTA TAATAAAG AATACCTGCT    3120
GATGGCAAAA AAAA                                                       3134
```

FIG. 15B

```
CGATGTTCGG AATTCAGACA TCAGATGGAT CCAGCTGCGG TCCTCTAGGA TTGTGCACCA         60
CTACCAAAAT GGAGAGGACC TGGATCAGAT GGAGGAATAT GAAGGGAGAA CAGAACTGCT        120
CAGGGATGGT CTCTCTGATG GAAACCTGGA TTTGCGCATC ACTGCTGTGA GCTCCTCTGA        180
CAGTGGCTCG TACAGCTGTG CTGTGCAAGA TGATGATGGC TATGCAGAAG CTGTGGTGAA        240
CCTGGAGGTG TCAGATCCCT TTTCCCAGAT CGTCCATCCC TGGAAGGTGG CTCTGCCTGT        300
GGTCGTCACA ATTCTCGTTG GGTCATTTGT CATCATTGTT TTTCTCTATA GGAAGAAAGT        360
GGCACAGAGC AGAGAGCTGA AGGGAAAAGA TGCAGCACTG GCGGAACTAC CTGCGATATT        420
GGGTGTATGT ACTGCAAATT TGAAGATCCT AGCTTCAAAA CTGATGAAAC AAATGGAAAA        480
ATTGGAGATT CAGAATTCAC TCTTGAAGAA ACGGTATGAG ATTACGGAGG AACTGGCTGC        540
AGATCTGGAG GAACATCTTG CTGAGAAGGA TTTAAGCACT GCAGATCTGA AGCTACTAGC        600
TGCAAAACTG GTGGAACAAA GAAGCAGT GGAGGAACGG GATTCACAGC TGAGGAAACA        660
GTATGAAAAG TTGGGTTCGC GTGCTACAAA TCTGAAGACA CAACTTAAAA AGTTGGAGAA        720
CGAAATTGAA GAAGTGGAGA ACACCTTAA AAAGATTGGT ATACGTGCTC CTAATCTGAA        780
GCTACACATG GCAGAACTGG TGGATCAAGC TGAAGCAGTG GAGAAACGGA ATCAGAGCT        840
GAAGAGCTAT TTGACAAATA TAGGTTTACG TGCTGCAGAG CTGAAAAAAT ACATTGCAGC        900
ACTGGAGAAA CGAATTGAAG CATTGGAAAC TAAAGAATTG GAACAACCAT CTAAAGAACA        960
GGATTGAAAG ATGAACTGCG CCTCACAGTA ACCACAGGAG TTAAGCTTCA TAGACTGCAG       1020
ACTGCACAGG ATAGCAACAT CGCCATAACG CAAAGCAAGC AAGGAAATCC ACACGGGGAA       1080
CAAGAGGAGC CAGTGTTTGT ATTGAGTGAG AACACTGCAG TTCTGCAAGC CACAGCTGCC       1140
TGAGGGACCA GCAAACTGAG GGTGTGTGAC CTCCATCTCA AATCCAGTTG AAGAAAGAC       1200
ACCATAGAAA AGAAGACTAC AAGAGGAAGA CAGAGATCCT GGAAAAGGGA CAGACATTTT       1260
GGGAATGAAC ATGGCCATGT ATCAGGGTTT GAGGAATTCT AATGAATATG TAAGGCTTCT       1320
GGAAATATAA ACATGCACAC AGAAGTAAAG GTAGAAAACT GCTTTGGGTG TTAACACTGT       1380
TCTCTATCAC AATATAATAA AGAAATACCT GCTGATGGCG ATGGAAAAGA AAAAAAAAA       1440
AAAAAAAAA                                                                    1449
```

FIG. 16

```
GCTCCTTCTG CATATTCTTC CTGAACTTTT TCTAAATCTT CTTTCCAGAT CTTCTTCCCC      60
ATCTGCTCCA GCACCTCCTC CTTGTATCCC CTTCCCCAAT CTTCCCTTCC CCACCTCCTT     120
CTCCTATCAT CTCTCATCTT TTACCCATTT TCTACCCACC TTCTGCCCCA TCTCCTCCAT     180
CATCTCCTTC TCAGTCTCCT TCCTCTCTCT CCTTTCCCCA ACTCCTCCCC CCCTCCTCTT     240
```

| | | | | | |
|---|---|---|---|---|---|
| CTCCAGCACA G | ATG CAC TTC ACA TCG | GGC TGC AAC CAC CCC | AGT TTC ACC | | 290 |
| | Met His Phe Thr Ser | Gly Cys Asn His Pro | Ser Phe Thr | | |
| | 1  5 | 10 | | | |

```
CTC CCC TGG AGG ACC CTC CTG CCT TAT CTC ATG GCT CTG CAC CTC CTC      338
Leu Pro Trp Arg Thr Leu Leu Pro Tyr Leu Met Ala Leu His Leu Leu
     15              20              25

CAG CCG GGA TCA GCC CAG CAA AGG GTG GTG GCA CCG AGC CTC CGT GTC      386
Gln Pro Gly Ser Ala Gln Gln Arg Val Val Ala Pro Ser Leu Arg Val
 30              35              40              45

ACT GCC ATC GTG GGA CAG GAT GTT GTG CTG CGC TGC CAG TTG TCC CCT      434
Thr Ala Ile Val Gly Gln Asp Val Val Leu Arg Cys Gln Leu Ser Pro
                 50              55              60

TGC AAG GAA GCT TGG AGA TCA GAC AAC AGA TGG ATC CAG CTG CGG TCC      482
Cys Lys Glu Ala Trp Arg Ser Asp Asn Arg Trp Ile Gln Leu Arg Ser
         65              70              75

TCT CGG CTT GTG CAC CAC TAT CAA TAT GGA TTG GAC CTG GGG CAG ATG      530
Ser Arg Leu Val His His Tyr Gln Tyr Gly Leu Asp Leu Gly Gln Met
             80              85              90

GAG GAA TAT AAA GGG AGG ACA GAA CTA CTC AGG AAG GGT CTC TCT GAT      578
Glu Glu Tyr Lys Gly Arg Thr Glu Leu Leu Arg Lys Gly Leu Ser Asp
         95              100             105

GGA AAC CTG GAT TTG CGC TTC ACT GCT GTG AGC ACC TCC GAT AAT GGC      626
Gly Asn Leu Asp Leu Arg Phe Thr Ala Val Ser Thr Ser Asp Asn Gly
110             115             120             125

TCA TAC AGC TGT GCT GTG CAA GAT GAT GAT GGC TAC GGA GAC GCT GTT      674
Ser Tyr Ser Cys Ala Val Gln Asp Asp Asp Gly Tyr Gly Asp Ala Val
                 130             135             140

GTG GAG CTG GAG GTG TCA GAT CCC TTT TCC CAG ATC GTC CAT CCC TGG      722
Val Glu Leu Glu Val Ser Asp Pro Phe Ser Gln Ile Val His Pro Trp
             145             150             155

AAG GTG GCT CTG GCT GTG GTT GTC ACA ATT CTG GTT GGG TCA TCT GTC      770
Lys Val Ala Leu Ala Val Val Val Thr Ile Leu Val Gly Ser Ser Val
         160             165             170
```

FIG. 17A

| | |
|---|---:|
| ATC AAT GTT TTT CTC TAT AGA AAG AAA GCT GCA CAG AGC AGA GAG CTG<br>Ile Asn Val Phe Leu Tyr Arg Lys Lys Ala Ala Gln Ser Arg Glu Leu<br>175                      180                185 | 818 |
| AGT GAGTCCTTCC AGCACCTTCC ACCACCAAAG TCCCTTTAAT GGAACTGATA<br>Ser<br>190 | 871 |
| GAAGACTGCA GAGTGCTGGG TTTATGCCAT GGGCTGGGGC TGTGGGATCT TTGGGGCTTG | 931 |
| GGATGTGTTG GGGCCGTGGG ATGTGCTGGG GTCGTGGGAT CTGTCAATCC TGATTGCTCC | 991 |
| TCTTCAGAAC TCTTGCCCAA TCGGTTCCTT CCGATTCATT TAACTCCTTC TTGGACCAAA | 1051 |
| GTGGTCATTG GCCTCTTACT AGAAAGAAAA GATTTGGGGT CTGGGTATGG GAGCAGCCAT | 1111 |
| GGGATGAGAA GGTGTTCCCT CTGACCATAC ATTTCTTTTG CTTCTATTTT GCA GAG<br>                                                                  Glu<br>                                                                  1 | 1167 |
| AGA AAA GAT GCA ATG TTG GGT CCC GGT GCT GAA AAG CTG AAG AAA TTA<br>Arg Lys Asp Ala Met Leu Gly Pro Gly Ala Glu Lys Leu Lys Lys Leu<br>              5                        10                    15 | 1215 |
| GCT TCA AAA CTG AAC GAA AAT GCT GAC GAA GTG GAG AAT TGC AAT TTA<br>Ala Ser Lys Leu Asn Glu Asn Ala Asp Glu Val Glu Asn Cys Asn Leu<br>        20                      25                    30 | 1263 |
| GAG CTG AAA AAA GAC TGT GAC GAG ATG AGT TCT GCC GTT GCA GAT CTG<br>Glu Leu Lys Lys Asp Cys Asp Glu Met Ser Ser Ala Val Ala Asp Leu<br>         35                   40                   45 | 1311 |
| AAG AAA TTG GCT GCA GTG ATT TGG ATA TGG GAT TTA AAG TTG TAT AAT<br>Lys Lys Leu Ala Ala Val Ile Trp Ile Trp Asp Leu Lys Leu Tyr Asn<br>50                   55                   60                65 | 1359 |
| CTA GCT GCC AAA CTG GGA CAA CAA ACT AAA GAA CTG GAG GAA CAG CAT<br>Leu Ala Ala Lys Leu Gly Gln Gln Thr Lys Glu Leu Glu Glu Gln His<br>             70                    75                    80 | 1407 |
| TCA CAG TTC CAG GGT CAC TTT CAG CAT ATG GAT TTA AGT GCT GTA AAA<br>Ser Gln Phe Gln Gly His Phe Gln His Met Asp Leu Ser Ala Val Lys<br>                85                    90                   95 | 1455 |
| CAG AAG AAA CTG GTT ACA AAA CTG GAG GAA CAC TGT AAT CAG ATG GTG<br>Gln Lys Lys Leu Val Thr Lys Leu Glu Glu His Cys Asn Gln Met Val<br>         100                    105                 110 | 1503 |
| AGA AGG AAT GTA AAG TTG GAG GCA GCA GCT GTA AAA CTG GGG CAA CAA<br>Arg Arg Asn Val Lys Leu Glu Ala Ala Ala Val Lys Leu Gly Gln Gln<br>         115                    120                 125 | 1551 |
| GCT AAA GAA TCA GAG GAA CAG AAA TCG GAG CTG AAG GAG CGC CAT GAG<br>Ala Lys Glu Ser Glu Glu Gln Lys Ser Glu Leu Lys Glu Arg His Glu<br>130                   135                    140                145 | 1599 |

FIG. 17B

```
GAG ATG GCA GAA CAA ACT GAA GCA GTG GTG GTA GAT ACT GAA GAA TAG        1647
Glu Met Ala Glu Gln Thr Glu Ala Val Val Val Asp Thr Glu Glu  *
            150                 155                 160

GGTGAGTCTT CCCCAAACCA AAGCAATACG GGGTTTCCCA TGGCATGACA AGCTGTCCCA      1707

CCTCAGCATC CGTTGCTTTT TATTTCTTTT CCAGAAAAAC CATCTGAAGA ATTGGATTGA      1767

GAGATGAACT GCGCCTCACA GTAACCACAG GAGTTAAGCT TCATAGATCA ATTACTACAC      1827

AGCATAAAAA ACCACGATTC CACAAACAGA GCAAGGAAAT CCACAGCGAG AACAAGAGGA      1887

GCCAGTGTTT GTGTTGAGTG AGAACACTGC AGTTCTGTGA GCCAAAGCTG CCTGAGGGAC      1947

CGCCGAACTG AGGGTGTGCG ACCTCCAACT CAAAGCAATT GGAAGAAAGA AACCATAGAA      2007

AGGAAGGAAA GGGGAGGAAG ACAGAGATCC TGGAAGAGAT ATGGGCATTT GGGGAAATAG      2067

TGTGACCATG TATCAGGCTT TGTGGACATC TAATGAGTAT GTAATGCTTA TGGAAGTAGA      2127

AGCATGCACG CAGAAACAAA GGTAGAAAAC TGCTTTGGGT GTTAACACTG TTCTCTGTCA      2187

CTATATAATA AAGAATACCT GCTGATGGCA                                      2217
```

FIG. 17C

```
AAAGGAGTGA GTTGTGTACA GGGGGGGTTAA ATGCTTTATA GACAAGAAAG AAATTGCTCT     60
AAAAGAGACT TATTCATCAT CATCATCATC TTCCTCCTCC TCTTCTTCCT CTTCTTCGTC    120
CTCTTCATCC TCTTCGTCTT CGTCCTCATC TTCCTCTTCT TCCTTCTTCT TCTTGCTCTT    180
CTCGGCCTTG GCAACTACTT TTTTGCCTGC ATCAACCTTC CCTTTGGCCC GGTATGCAGC    240
GATATCCTTC TCAGTCTCCT TCCTCTCTCT CCTTGGCCCA ACTCCTCCCC CCTCCTCTTC    300
TCCAGCACAG ATGGCCTTCA CATCGAGCTG CAACCACCCC AGTTTCACCC TCCCCTGGAG    360
GACCCTCCTG CCTTATCTCG TGGCTCTGCA CCACCTCCAG CCGGGATCAG CCCAGCTCAG    420
GGTGGTGGCA CCGAGCCTCC GTGTCACTGC CATTGTGGGA CAGGACGTCG TCTGCGCTGT    480
CACTTGTCTC CTTGCAAGAA TGCTTGGAAT TCAGACATCA GATGGATCCA GCACCGTTCC    540
TCTAGGATTG TGCACCACTA CCAAGACGGA GTGGACCTGG AGCAGATGGA GGAATATAAA    600
GGGAGGACAG AACTGCTCAG GGATGGTCTC TCTGATGGAA ACCTGGATTT GCGCATCACT    660
GCTGTGAGCA CCTCTGATAG TGGCTCATAC AGCTGTGCTG TGCAGGATGA TGATGGCTAT    720
GCAGAAGCTT TGGTGGAGCT GGAGGTGTCA GATCCCTTTT CCCAGATCGT CCATCCCTGG    780
AAGGTGGCTC TGGCTGTGAT CGTCACAATT CTGGTTGGGT CATCGGTCAT CATTGTTTTT    840
CTCTGTAGAA AGAAAGAGAG AAAAGATGGA GAGTTGGCGG AACAAGCTGA AATACTGGAG    900
AGAAAAGATG CAATGTTGAC GGAACAAGCT GAAACACTGG AGAAAAAAGA TGTAATGTTG    960
AAGGAACAAG CTATGATAGC GGAATCAAAT GCTGAAGATC TGAAGAAACT GGCTGCGAAA   1020
CTGGAGAAAC ACTCTGAAGA GATGGGGACA AGGGATTTAA AGTTGGATAA ATTAGCTGCC   1080
AAACTGGAAC ATCAAACTAA AGAATTGGAG AAACAGAAAT CGGAGCTGAA GAGTCACTTT   1140
CAGTATATGG ATTTCAATGC TGGAAAACAG AAGAAAATGG TTACAAAACT GGAGGAACAC   1200
TATGAATGGA TGGTGACAAG GAATGTAAAA TTGGAGATAC CAGCTATAAA AGTGGGGCAA   1260
CAAGCTAAAG AATCAGAGGA ACAGAAATCG GAGCTGAAGG AGCACCATGA GGAGATGGGG   1320
CAACAAGCTA AGAATCAGA GGAACAGAAA TCGGAGCTGA AGGAGCACCA TGAGGAGATG   1380
GGGCAACAAG CTAAAGAATC AGAGGAACAG AAATCGGAGC TGAAGGAGCA CCATGAGGAG   1440
ATGGGGCAAC AAGCTAAAGA ATCAGAGGAA CAGAAATCGG AGCTGAAGGA GCACCATGAG   1500
GAGATGGGGC AACAAGCTAA AGAATCAGAG GAACAGAAAT CGGAGCTGAA GGAGCACCAT   1560
```

FIG. 18A

```
GAGGAGATGG GGCAACAAGC TAAAGAATCA GAGGAACAGA AATCGGAGCT GAAGGAGCAC    1620

CATGAGGAGA TGGGGCAACA AGCTAAAGAA TCAGAGGAAC AGAAATCGGA GCTGATGGTA    1680

GAAACTGAAG AAGCAGAAAA ACCATCTGAA GAATCAGATT GAGAGATGAA CTGCGCCTCC    1740

CAATAAGCAC AGGAGTTAAG CTTCATAGAT CAATGACTGT ACAGCAAACA AAACCACGA     1800

TAACTCAAAC AGAGCAAGGA AATCCACAGC GAGAACAAGA AGAGCCAGTG TTTGTGTTGA    1860

GTGAGAACAC TGCAGTTCTG TCAGCCAAAG CTGTCTGAGG GACCGCCAAA TTGAGGGTGT    1920

CGAACCTCCA ACTCAAAGCC AATTGGAAGA AAGAAACCAT AGAAAGGAAG AAAAGGGGAG    1980

GGAGACAGAG ATCCTGGAAA AGATATGGGC ATTTGGGGAA ATAGTGTGAC CATGTATCAG    2040

GCTTTATGGA AATCTAACAA ATATGTCATG GTTTTGTAAA TACAAGCATG CACGCAGAAA    2100

CAAAGGTAGA AAACTGCTTT GGGTGTTAGC ACTGTTCTCT GTCCCTATAT AATAAAGAAT    2160

ACCTGCTGAT GGCAAAAAAA AAAAAAA                                       2188
```

FIG. 18B

```
TTGCAAGAAT GCTTGGAGCT TAGATATCAG ATGGATCCAG CTGCGGTCCT CTGGTTTTGT    60
GCACCACTAC CGAAATGGAG AGGACCTGGA GCAGATGACA GAATATAAAG GGAGAACAGA   120
ACTGCTCAGG AAGGGTCTTT CTGATGGAAA CCTGGATTTG CGCATCACTG CTGTGAGCAC   180
CTCCGATAGT GGCTCATACA GCTGTGTTGT GCAAGACGAT GATGGCTATG CAGAAGCGTT   240
GGTGGAGCTG GAGGTGTCAG ATCCCTTTTC CCAGATCGTC CATCCCTGGA AGGTGGCTCT   300
GGCTGTGATC GTCACAATTC TGGTTGGGTC ATTTGTCATC ATTGCTTTTC TCTATAGGAA   360
GAAAGCGACA CAGAGCAGAG AGCTGAAAAG AAAAGATGCA ATGTTGGGAA GAAAAGATGC   420
AGTGCTGGAG GAACTACCTG CGATATTAGA TTCAAGTGCT GCAAATCTGA AGATACTAGC   480
TTCAAAACTG GTGAAACAAA CTGAAAAATT GGACATACGG AATTCACTAA TGAAGAAACA   540
GTATGAAATG ACAGAGAAAC AAGCTGCAGA ACTGGAGAAA CACTTAATAA ATACCGATTT   600
AAGTGCTGCA GATCTGAAGA TAGCAGCTGC AAAACTGGAC AAACAAACTG AAGAACTGGA   660
CAAATGGAAA TCAGCACTGA AGATACAATA TGAAAAGTTG GGTTTACGTG CTGCAAATCT   720
GAAGACACAA GTTACAGAAC TGGCGAAACA AACTGAAGAA GTGGAAAATC ACTATGAAGA   780
GATGGGTTTA CGTGCTCCTA ATCTGAAGAA AAATATAGTA GAACTGGAGA ACAAACTGA   840
GCACGTGGAC AATCGGAAAT CAGAGCTGAA GAAACAGTAT GAAAATTTGG CTTCACATGC   900
TTCAGAGCTG AAGAAACAAG CTGAAGTACT GGAGGAACAA GCTGAACAAC TGGAGATTCA   960
GAATTCACTG TTGAAGATAC GCAATAAACA TAGGGAGAGA AAGAATGAAA TGTTGGAGAA  1020
ACAAACTGTA GAACAGGAAC AAACTGAAGA ATGGGCAGAA TCTAAAAAAT CGGTGGTTGA  1080
AACTAAAGAA TTGGAACAAC CATCTAAAGA ACAGGATTGA GAGATGAACT GCGCCTCACA  1140
GTAACCACAG GAGTTAAGCT TCATGGACTG CTGACTGCAC AGGATAGCAA CACCGCCATA  1200
ATGCAAAGCG AGCAAGGAAA TCCACAGCGA AAACAAGAGG AGCCAGTGTT TGTGTTGAGT  1260
GAGAACACTG CAGTTCCATG AGCCAAACCT GCCTGAGGGA CCGCCCAATT GAGGGTGTGC  1320
GACCTCCAAC TCAAAGCCAA TTGGAAGAAA GAAACCATAG AAAGGAAGAC TACAAGAGGA  1380
AGACAGAGAT CCTGGAAAAG GGATAGACAT TTTGGGATTT AACATGGCCA TGTATCAGGG  1440
TTTGAGGAAT TCTAACGTAT ATATAAGGCT TTTGGAAATA TAAACAT              1487
```

FIG. 19

```
GGATGATCAT CCGACTCTTC TCATCATAAA TTCGTCTTCT TCTTTGCAGA GAAACTGGTT     60
ACAAAACTGG GTGAGTCCAA CCTCCCAAAC TAAATTAAAA GCAGTCAGAC TTTGTGAGCT    120
GTGGGATGAG ACGTTCTTCT CATCATGTGC TGCTTTCCTT TTACTTTTCC AGAGGAACAC    180
TTTGAATGGA TGGGTGAGTC TCCCCTCCCA AATTAAAAAT GTTGGGGTCT TCCTGTGTGA    240
GCTGTGGGAT GAGCTGTTCC TCCCATCATG CACTGGTTCT AATTTTCCTT TGCAGAGAGA    300
AGGAATGTAA AGTTGGGTGA GTCTTCTTCC CCAACCAAAG GGATTTGGGG TCTTCCATGG    360
GATCAGCCAT GGGATGATAA CCTGAACCTT ATCACATATT TCTTATTTGT TCTTTTTGCA    420
GAGATACCAG ATCTGTAATA CTGGGTGAGT CCTCCCTCCC AAATTAAATA CAAAAGGGGA    480
TCTGCCTGTG TGAGCTGTGG GATGAGATGT TCCTCTCATC ACGCATTATT TTCTCTTTCT    540
TTTCCAGGGC AACAAGCTAA AGAATCAGGT GAGTCTTCTT CCCTGTCCCA AGGACTATG     600
GGTTTCCCAT GGGATGACAA GCTGTGCCAC CTCCTCACGA GGTGCTTCTT CTTTCTTTTT    660
TGCAGAGAAA CAGAAATCGG AGCTGAGTAA GTTGCAGTCA CTGAACTGAG GAATGTGGG     720
GTCTTCCCAA AGTCTTGTGT ATGGGATGAA AAATCCCCTC TGACCATGCA CTGCTTTTCT    780
CCTCCTTTGC CAGAGGAGCG CCATGAGGAG ATGGGTGAGT CTCCCCTCCC ATATTAAAAT    840
CGTTGGGGTC TTCCTGTGTG AGCTGTGAGA TGAGATGTTC CTCTCATCAT GCGATGCTTT    900
TCTCTCTTTT CCAGCAGAAC AAACTGAAGC AGTGGGTGAG TCTTTGTCCC CAACCCAAAG    960
GAATATGGGG CAATCCATGG GATGACAAGC TGTCCCATCT CATCGTGCAT TGCTTTCCTA   1020
TTCCTTTTTT CTAGTGGTAG ATACTGAAGA AGCGGGTGAG TCTTTCCCAA ACCAAAGCAA   1080
TACGGGGTTT CCCATGGCAT GACAAGCTGT CCCACCTCAG CATCCGTTGT TTTTCTCTTT   1140
CTTTTCCAGA AAAACCATCT GAAGAATTGG ATTGAGAGAT GAACTGCGCC TCACAGTAAC   1200
CACAGGAGTT AAGCTTCATA GATCAATGAC TGCACAGCAT ACAAAAACCA CGATACCTCA   1260
AACAGAGCAA GGAAATCCAC AGCGAGAACA AGAGGAGCCA GTGTTTGTGT TGAGTGAGAA   1320
CACTGCAGTT CTGTCAGCCA AGCTGCCTG AGGGACCGCC AAACTGAGGG TGTGCGACCT    1380
CCAACTCAAA GCCAATTGGA AGAAAGAAAC CATAGAAAGG AAGGAAAGGG GAGGAAGACA   1440
GAGATCCTGG AAGAGATATG GGCATTTGGG GAAATAGTGT GACCATGTAT CAGGCTGTGT   1500
GGACATCTAA CGAATATGTC ATGTTTTTGT AAATACAAGC ATGCACTCAG AAACAAAGGT   1560
```

FIG. 20A

```
AGAAAACTGC TTTGGGTGGT AACACTGTTC TCTGTCAAAA TATAATAAAG AATACCTGCT    1620
GATGGTAATG GATCATTGAT TGTGAGCAGT TATTGGGGTT TGGTTCCATG AAACAGGCTG    1680
AGTCTTCTTC CCAGAAACAA AGCAACGTGG GCTCTATCGG ATAACAAGCC GACCCTTCTC    1740
ACCATGCACT GCTATTCCAG CACAACAAGG CTCTCTCCAG GAAGCTAAAA AGGGATAAAA    1800
TAAATTAATA GGAAAGAAAT ACACAAAAAC AAGAAAATTT AAAAAGAAT ACTCCAAAAA     1860
ATCTATAATT ATTACAATAA AAACTTTAAA AAAACACACC AACCTTCCAC CCTGGGGGAG    1920
CACCAATGAC AGCCTTTTGT GCCCCATCGC GGTTTTATGA GAACAGCCAC ACACTTCAGA    1980
GCTGACCCCG TGAGCCCCAC AGTGGGGGGA CCTCCCACAG TGGGTGGACC TCCTCCACAA    2040
CCACCCCCAT CACTCACATT GAATGCCCAA AGAAACAACA GCCCCAAAGG TTCCTCCTGG    2100
TGCTTCAGCC GCGTGTGTTC CTCATTCTGC TGTGCTGATG GTGATCATTA ACCCAACAGC    2160
TCATTAACCA GGTTATGGCT CAGGTGCGTG CTGCTGAACA AGCTTGGAGC CTAAAATGGT    2220
TCCTGCACAC ATCCCAGGGG ACGGCCCTCC ACCTTTCACT CCCCGCCATT ACAGCTCTCC    2280
TTAATCAGAG GAATACAGAT TCCATGCACT GAGTGCACTG AGCCATCGCC CACCTTCCCT    2340
ACAAACACCT CCTGGTCCCC ACAAACCCTC ACTGTGGGAA GAGGGGCTCT GGGGGGGTCA    2400
CAGGGACAAA CATTTAATAA TTCCTGTATT AATGGTTGAT TAACTTAAAA ATCTGTACTG    2460
ATCAAATAAA CTGCCACCCC TTGGGCATAG CTCAGAGCAT GCTCATGGAG TACAGCCCAC    2520
AGCTTTCCTC TGTGCTAGGG CAATGCTTCT CCTGGGTCCA TGTTCATCCT GGGTGGATGC    2580
AGAGCCCCAG GGTGGTACAT GAAACTGCAA TGGGATGTCA GTGTTCAGAG TTCTCCAACC    2640
GTCTGCCCCA TTGCCAAAGG GGTAAAGTTC CTCGGAGCAG ATTACCACAC CCTGGAGCTG    2700
GGCAAAGGTT GACGCTGGGC AAAGGTAGAA GCTGGGCATA GCTGCACGTT TCCTGCAGCT    2760
CAGGTGAGGG ATTTCTGTCT CTGTGGGGCT CCTTGTAGGG GAAATCCTTG GGGGGTCATC    2820
TGCTCTGCCT CACAGCCTGT GAGGAGCACT GGCACTGCCC AAGGCAGTGG TGGCTGTGCT    2880
CATGGAACTG ATGTTTGAGT GACCCCATCC CCTCCTCTCC TGGTGGCTGT AACCCTCTGG    2940
CCCCTCTCCT CCTACAGCTC CTTCCTGCAT ATTCTTCCTC AACTTTTTCT AAATCTTCTT    3000
TCCAAATCTT CTACCCCATC TGCTCCAGCA CCTCCTTCTC CATCTCCTTC CCCAAACTCC    3060
TCCTTATATC CCCTTCCCCA ATCTCCTTCA CCCACCTCCT TCTCCTATCA TCTTCTCTCA    3120
TCTTTTACCA TTTTCTACCC ACCTTCTGCC CCATCTCCTC CATCATATCC TTCTCAGTCT    3180
CCTTCCTCTC TCTCCTTTCC CCAACTCCTT CCCCCCTCCT CTTCTCCAGC ACAGATGGCC    3240
```

FIG. 20B

```
TTCACATCGA GCTGCAACCA CCCCAGTTTC ACCCTCCCCT GGAGGACCCT CCTGCCTTAT    3300
CTCGTGGCTC TGCACCACCT CCAGCCGGGA TCAGGTAGGG GTCCTGTGGG GCTGCTGTGC    3360
CTGGCACACG TGTTGCTATG GGGTGGGGGA GCCGCCATGG GGCAGGAGG  ACACAAGTCC    3420
AGCCCCCAGC CCCACTTGGG TTTCACTTTC ACTTTGGTAA TTCCATGATA GATGCCATTT    3480
TGGGTAGAAT TTCTGTCTCT TCTTCACCTC TGCCACACGG TGTGAGTGGG CTCCCACCCC    3540
CAGCAATCCT TCCCCCTCTC TCCTGATCCC TCCCCACTGC TTTTACACCA GATGGAGCAC    3600
ACACCAACTC ACCCTGTGCC GCTCCATGCC CCACATTAA  CACAGACACC ATCTCACCAT    3660
CTCTCCGTGC CCTTCGCATT GCCCAGCCCA GCTCAGGGTG GTGGCACCGA GCCTCCGTGT    3720
CACTGCCATT GTGGGACAGG ACGTCGTCTG CGCTGTCACT TGTCTCCTTG CAAGAATGCT    3780
TGGAATTCAG ACATCAGATG GATCCAGCAC CGTTCCTCTA GGATTGTGCA CCACTACCAA    3840
GACGGAGTGG ACCTGGAGCA GATGGAGGAA TATAAAGGGA GGACAGAACT GCTCAGGGAT    3900
GGTCTCTCTG ATGGAAACCT GGATTTGCGC ATCACTGCTG TGAGCACCTC TGATAGTGGC    3960
TCATACAGCT GTGCTGTGCA GGATGATGAT GGCTATGCAG AAGCTTTGGT GGAGCTGGAG    4020
GTGTCAGGTC AGTGGCTGGG GTGACGTCTC CAGGTGTCCC TGGGTTTGTG GGTCCCACCC    4080
AACCTCTGTC CATCCTCATC CTCACGTCCA TGGATGGAGA GCTGAAGGAC AGCAGCCTTT    4140
GGAAGAGGTC AGGGCTGAAT TGTTTTATGA GATGCTGGAA TTAGAGCGGA CACACGGTGT    4200
GATTTGGGGA ATAGACTGCA TGGATGAGGT GGTTGGGTTG GATTTCTGGG ATGGGTTTCT    4260
CCATGTATCA GTGGCAGTGG GCACACGATG CTGAGCAGCT CCTCCGCCTG TGCCAATATG    4320
GGGACGCTGC CATTGTGTGT CACTGTTCCC TGCTCACTGC TCCTTCTGAA CAGGTGAATT    4380
CCGTTACCTT TTCCTTGGGA ACAGGACTAC AAAAAAGGTC TAGGGAAAAG GGTCTAGCAG    4440
GTAGGGACCT TCCACCGAGA CCGACACTAG CAGTGTTAAG ACCAACCCAG TAGCCAGTAG    4500
TAACAAAAAG AGACATCTTT CTTTCCACTC AACTCGTACC TCCCCTACCT CGTGTCCTTC    4560
CACAACACGT ACCTGTCCTT ACCAGCCCCA CCACGACTCG AGTCCAGGTG TCTCCATGTG    4620
TCCTCCTGCT TCCCTCTAAA AAGGACTCTA AGGGTCACGA GTAATTTATT GAAAAGGGAA    4680
AGAAAAACCC TTACTTCCTT CCTTTTTTTC CCCACACCCA CCCTTCTATC CTTACACCGA    4740
CATCCGTCCA CCTTTCA                                                  4757
```

FIG. 20C

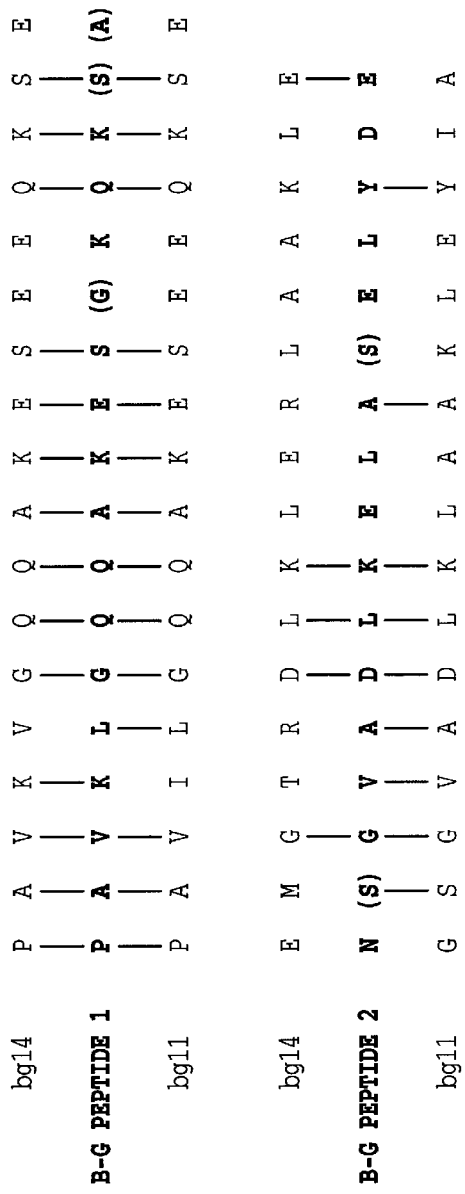

| | | | | | |
|---|---|---|---|---|---|
| CTGGGTCAGA | TCTCCCGGCT | TCATTTCTCT | CCATCCCTGG | GGTCCCCTCC | TCCCGTCTGA | 60 |
| CTGCTGGAGG | GCGGATGATC | ACCCCCTGTC | TGCACCCCTC | CCTGCGCTAT | CTGCAGCCCT | 120 |
| TCAGATGCAC | CGCACCCCAT | TTGCACTCCC | TGCCCCCCCT | TTGTACACAT | GGGGGGGATA | 180 |
| TCAGCCCTCC | TCCTTCCACC | CACCCGTATC | AGAGCCGCTG | TGCTGCTGAG | GGAGGCGGAT | 240 |
| GGGACGGCTG | CATCGCTCCC | CCTCAGCTTC | ACAGAGCTGC | TTTGCTGCGG | GTTTTGGCTG | 300 |
| CAATTCGGAC | CCTCTAAGAA | TGATCCCTCG | TTGTGAGACT | CCGCTGCAAA | GCTGATCCGT | 360 |
| TCGAGCTCTC | CTCCTACAGC | TGCTGCCCTC | ATATTCTCCC | CACACTTCTT | CCCCATATTC | 420 |
| TTTCCAAATC | CTCTTCCCCA | TCTCCTCCAC | CGTCTCTTTC | TCAGAGTCCT | TCCTCTCTCT | 480 |
| CCCTAAATTC | TTCCCCCCTC | CTCTCCTCCA | GCACAGATGC | GCTTCACATC | GGGATGCAAC | 540 |
| CACCCCAGTT | TCACCCTCCC | CTGGAGGACC | CTCCTGCCTT | ATCTCGTGGC | TCTGCACCTC | 600 |
| CTCCAGCCGG | GATCAGGTAG | GGGTCCTGTG | GGGCTGCTGT | GCCTGGCACA | GGTGTTGCTG | 660 |
| TGGGGTGGGG | GAGCAGCCAT | GGGGCAGGGA | GGACCCATGT | CCAGCACCCA | GCCTCGCTTG | 720 |
| GGTTTCTCTT | TCACTTGGGC | TATTTCATGA | AATGTGTGAT | TCGGGTGGA | ATTTCTGTCC | 780 |
| CTTCTTCACC | TCCACCACAC | GGTGTGAGTG | GGCTCCCACC | CCCAGCAATC | CTTGCCCACT | 840 |
| CCCTCCTGAT | CCCTCCCCAC | TGCTTTTACA | TGGGATGGAG | CACACACCAA | CTAACCCTGT | 900 |
| GCCGCTCCAT | GCCCCCACAT | TAACACAGCC | ACCATCTCAC | CATCTCTTCG | TGCCCTTCTC | 960 |
| ATTGCCCAGC | CCAGCTCAGG | GTGGTGGCGC | CGAGCCTCCG | TGTCACTGCC | ATCGTGGGAC | 1020 |
| AGGATGTCGT | GCTGCGCTGC | CACTTGTGCC | CTTGCAAGGA | TGCTTGGAGA | TTGGACATCA | 1080 |
| GATGGATCCT | GCAGCGGTCC | TCTGGTTTTG | TGCACCACTA | TCAAAATGGA | GTGGACCTGG | 1140 |
| GGCAGATGGA | GGAATATAAA | GGGAGAACAG | AACTGCTCAG | GGATGGTCTC | TATGATGGAA | 1200 |
| ACCTGGATTT | GCGCATCACT | GCTGTGAGCA | CCTCCGATAG | TGGCTCATAC | AGCTGTGCTG | 1260 |
| TGCAGGATGG | TGATGGCTAT | GCAGACGCTG | TGGTGGACCT | GGAGGTGTCA | GGTCAGTGGC | 1320 |
| TGGGGTGATG | TCTCCAGGTG | TCCCTGGGCT | TGTGTGTCCC | CTACCGACCT | CTGTCCATCC | 1380 |
| TCATCCTCAC | ATCCTAGGAT | GGAGAACTGA | AGGACAGCAG | CCTTTGGAAG | AGCTCAGGGC | 1440 |
| TGAACAGCTC | CATGAGATGC | TGGAGTTGGA | TCGGGCACAT | GGTGTAATTT | GAAAATGGAT | 1500 |
| ATGCATGGAT | GAGGTGGTTG | GGTTGGGTTT | CTGGGATGGG | TTTCTCCACG | TCTCAGTGGC | 1560 |

FIG. 25A

```
AGTGGGCACA CGATGCTGAG CAGCTCCTCC GCCTGTGCCA ATATGGGGAC GCTGCCATTG    1620
TGTGTCACTG CTCCCTGGTT GTTGTCCCTT CGGGTTCTGT GATCTCCAGA AGTCGAAGTC    1680
GTGTTTGTCC ACATAAGGCA GTGGAAAAAG GAACCCTTGT CCTGATGTCT TTTCCAGATC    1740
CCTTTTCCCA GATCGTCCAT CCCTGGAAGG TGGCTCTGGC TGTGGTCGTC ACAATTCTCG    1800
TTGGGTCATT TGTCATCAAT GTTTTTCTCT GTAGGAAGAA AGGTGAGCTG AGAGCGGAGG    1860
GGATGGAGCA CAGGGAGGTG TTGTGCATGG ACAGGGATGG TCGGGGTGGT GCTGAGCTCT    1920
GGTGTACAGA GGTACACAGG AGGAGAAAGG GAGATTTTTC CTGACATTCC CACTGCCCAT    1980
TAAATAACAT TGCCTTTCTT TTGGGGAAAT GAAGGAGGAA AAAAGAAGT GTGGGTGGGC     2040
AGATAGGAAA GTGGGTGGAC CGTGGGGCAG GTGGAAAGGT CCAGACCTCG GGACGTCCCC    2100
AAACCAAGCT GCCCTGCTGA CTACCTCTTC CTCCAATTTG TTTTCCAGCG GCACAGAGCA    2160
GAGAGCTGAG TGAGTCCTTC CAGCCCCTTC CACCACCAAA GTCCCTTTAA TGGAACTGAT    2220
AGAAGACTGC AGAGTGCTGG GTTTATGCCT TGTGCTGGGG CCATGGGATC TATGGGACCT    2280
TGGGATGTGT TGGGGCCGTG GGATGTGCTG GGTCGTGGGA ATCTGTCAAC CCTGATTGAT    2340
CCACTTCAGA ACTCTTGCCC AATCGGTTCC TTCCGATTCA TTTAACTCCT TCTTGAGGCC    2400
AAAGTGGTCA TTGGCCACAT CCCAGAAAAA AGGGTTTGGG GTCAGGGTGT GGGAGCTGAT    2460
CGCATGGAAA CGTGTCCCCT CTGACCATGC ATTTCATTTG CTTCTATTTT GCAGAGAGAA    2520
AAGATGCAGC GTTGGGTAAG TCTCCTCCCC ATATGTGAGG GAATTCAGGG TGTCCCCATG    2580
GCATCAGCAG TGGGATGAGC AGCTGTCCGC TCTGACCATG CACTGCTCTG CTCTTTCTTT    2640
TCCAGCGGAA CTAGATGAGA TATCGGGTGA GTCTCCATTC CCAATTGTAT TCTTTCAAAT    2700
GTTCTGCCTT GGGGAGCTGT GGGATAGGAT GTTCTTCTCA CCATGCACTG ATTCTACCTT    2760
TCCATTGCAG GTTTAAGTGC TGAAAATCTG AGTAAGTGTC CCTCCTGACA CTGAAGGAAT    2820
TTGGGGTATT CCCATGGGAT CAGCCATTGA ATGAAAACAT GGCCCCCTCT CTTCATGCAT    2880
TTCCTATTTC TTACCTTTGC AGAGCAATTA GCTTCAAAAC TGAGTGAGTG CTCACTCCCA    2940
AACTCAAAGT AAAGAGAGTC TGCCTGTGTG AGCTGTGGGA TGAGATGTTC CACTCATCGT    3000
GCATTGCTTT TCTCTTTATT TTCCAGACGA AAATGCTGAC GAGTGGGTGA GTCTACATTC    3060
ACTAATGCAA AGAAATATGG GGTCTCCCAA GGGATGACAA GCGTGTCCCG CATCATCATT    3120
TGGTGCTTCT TCTGTCTTTT TTTTTGCAGA GGATTGCAAT TCAGAGCTGA GTAAGTTGCA    3180
GTCACTGAAC TGAGGGAATG TGGGGTCTTC CCAAGGGACA GTGCATGGGA TGAAAAATCC    3240
```

FIG. 25B

```
CCTCTGACCA TGCACTGCTT TTCTCTTTCT TTCCCAGAGA AAGACTGTGA AGAGATGGGT    3300
GAGTCCCCCC CCCCAAAATT AAACGTTGGG GTCCTCATGT GGAGCTGTGG ATGAGATGTC    3360
CTCTCATCAC GCACTGTTTC TACATTTCTT TGCAGGTTCT GGCGTTGCAG ATCTGAGTAA    3420
GTCTCCCCTA CCAGCACGGA AGGAATTTGT GGTCTTCCCA TGGGATCAGC CATGGGACTG    3480
ATCATCTGAG CCCTCTCATC ATGCATTTCA TATTCGTTCC TTTTGCAGAG GAACTGGCTG    3540
CAAAATTGGG TGAGTGTTGC CTCCCAAATT AAATTAAAAA AGGGGGTCTG CCTGGGCTCG    3600
CTGTGGGATA GGATCTTCCT CTCACTGTGT GTTGCTTTTC CCTTTCTTTT CCAGAGGAAT    3660
ATATTGCAGT GAATCGTGAG TCTCCCCTCC GAAATTATAA ATGCTGGGGA AATCTTGTGT    3720
GCGATCGTGG GTAGAGCTCT TCCTCTCATC ATGCACTGTT TCTGCTTTTC CTTTGCAGGG    3780
AGAAGGAATG TAAAGTTGAG TGAGTCTCTC TTCCCAAACC AAACAGATTT GGGGTCTTCC    3840
CATGGGATCA GCCATGGGAT GATAATCTAA CCCTACTCAT CATGCATTTC TTATTGGTTC    3900
CTTTGGCAGA TAATATAGCT GCCAAACTGG GTGAGTCCCC CCTCACAGAT TACATAAAAA    3960
ATGGGGTCTG CCTGTGTGAG CTGTGGGATG AGATGTTCCT CTCATCATGT ACTACTTTTC    4020
TCTTCCTTTT CCAGCACAAC AAACTAAAGA ATTGGGTGAG TCTTCTTTCC CCAAACAAAG    4080
AAATACGGGA TTCCCATGGG ATGACAAGCT GTGCCACCTC ATCATGCCCT GTTTTTTCTG    4140
TCCTTTTTGC AGAGAAACAG CATTCACAGT TCCGTAAGTT GCAGTCACTA AACTGAAGGA    4200
ATGTGGGGTC TTCCCAAAGT CCTGCATACG GGATGAAAAA TCCCCTCTGA CCATGCACTG    4260
CTTTTCTCTT TCTATTCCAG ACAGACACTT TCAGCGTATG GGTGAGTCTC TCCCCCCCAA    4320
ATTAAAAACG CTGGGGGCAT CCTATGGGAG CTGTGGGATG AGATTTCCT CTCATCACAC     4380
ACTCCTTCTG CTTTTCCATT GCAGATTTAA GTGCTGTAAA CCAGAGTAAG TCTCCCTCCC    4440
TGCACAGAAG GAACTTCCAG TTTTCCCATG GGATCAGCCA TGGGATGATC ATCCGACTCT    4500
TCTCATCATA AATTCGTCTT CTTCTTTGCA GAGAAACTGG TTACAAAACT GGGTGAGTCC    4560
AACCTCCCAA ACTAAATTAA AAGCAGTCAG ACTTTGTGAG CTGTGGGATG AGACGTTCTT    4620
CTCATCATGT GCTGCTTTCC TTTTACTTTT CCAGAGGAAC ACTTTGAATG GATGGGTGAG    4680
TCTCCCCTCC CAAATTAAAA ATGTTGGGGT CTTCCTGTGT GAGCTGTGGG ATGAGCTGTT    4740
CCTCCCATCA TGCACTGGTT CTAATTTTCC TTTGCAGAGA GAAGGAATGT AAAGTTGGGT    4800
GAGTCTTCTT CCCCAACCAA AGGGATTTGG GGTCTTCCAT GGGATCAGCC ATGGGATGAT    4860
AACCTGAACC TTATCACATA TTTCTTATTT GTTCTTTTTG CAGAGATACC AGCTGTAATA    4920
```

FIG. 25C

```
CTGGGTGAGT CCTCCCTCCC AAATTAAATA CAAAAGGGGA TCTGCCTGTG TGAGCTGTGG      4980

GATGAGATGT TCCTCTCATC ACGCATTATT TTCTCTTTCT TTTCCAGGGC AACAAGCTAA      5040

AGAATCAGGT GAGTCTTCTT CCCTGTCCCA AAGGACTATG GGTTTCCCAT GGGATGACAA      5100

GCTGTGCCAC CTCCTCACGA GGTGCTTCTT CTTTCTTTTT TGCAGAGAAA CAGAAATCGG      5160

AGCTGAGTAA GTTGCAGTCA CTGAACTGAG GGAATGTGGG GTCTTCCCAA AGTCTTGTGT      5220

ATGGGATGAA AAATCCCCTC TGACCATGCA CTGCTTTTCT CCTCCTTTGC CAGAGGAGCG      5280

CCATGAGGAG ATGGGTGAGT CTCCCCTCCC ATATTAAAAT CGTTGGGGTC TTCCTGTGTG      5340

AGCTGTGAGA TGAGATGTTC CTCTCATCAT GCGATGCTTT TCTCTCTTTT CCAGCAGAAC      5400

AAACTGAAGC AGTGGGTGAG TCTTTGTCCC CAACCCAAAG GAATATGGGG CAATCCATGG      5460

GATGACAAGC TGTCCCATCT CATCGTGCAT TGCTTTCCTA TTCCTTTTTT CTAGTGGTAG      5520

ATACTGAAGA AGCGGGTGAG TCTTTCCCAA ACCAAAGCAA TACGGGGTTT CCCATGGCAT      5580

GACAAGCTGT CCCACCTCAG CATCCGTTGT TTTTCTCTTT CTTTTCCAGA AAAACCATCT      5640

GAAGAATTGG ATTGAGAGAT GAACTGCGCC TCACAGTAAC CACAGGAGTT AAGCTTCATA      5700

GATCAATGAC TGCACAGCAT ACAAAAACCA CGATACCTCA AACAGAGCAA GGAAATCCAC      5760

AGCGAGAACA AGAGGAGCCA GTGTTTGTGT TGAGTGAGAA CACTGCAGTT CTGTCAGCCA      5820

AAGCTGCCTG AGGGACCGCC AAACTGAGGG TGTGCGACCT CCAACTCAAA GCCAATTGGA      5880

AGAAAGAAAC CATAGAAAGG AAGGAAAGGG GAGGAAGACA GAGATCCTGG AAGAGATATG      5940

GGCATTTGGG GAAATAGTGT GACCATGTAT CAGGCTGTGT GGACATCTAA CGAATATGTC      6000

ATGTTTTTGT AAATACAAGC ATGCACTCAG AAACAAAGGT AGAAAACTGC TTTGGGTGGT      6060

AACACTGTTC TCTGTCAAAA TATAATAAAG AATACCTGCT GATGGTAATG GATCATTGAT      6120

TGTGAGCAGT TATTGGGGTT TGGTTCCATG AAACAGGCTG AGTCTTCTTC CCAGAAACAA      6180

AGCAACGTGG GCTCTATCGG ATAACAAGCC GACCCTTCTC ACCATGCACT GCTATTCCAG      6240

CACAACAAGG CTCTCTCCAG GAAGCTAAAA AGGGATAAAA TAAATTAATA GGAAAGAAAT      6300

ACACAAAAAC AAGAAAATTT AAAAAGAAT ACTCCAAAAA ATCTATAATT ATTACAATAA      6360

AAACTTTAAA AAAACACACC AACCTTCCAC CCTGGGGGAG CACCAATGAC AGCCTTTTGT      6420

GCCCCATCGC GGTTTTATGA GAACAGCCAC ACACTTCAGA GCTGACCCCG TGAGCCCCAC      6480

AGTGGGGGGA CCTCCCACAG TGGGTGGACC TCCTCCACAA CCACCCCCAT CACTCACATT      6540

GAATGCCCAA AGAAACAACA GCCCCAAAGG TTCCTCCTGG TGCTTCAGCC GCGTGTGTTC      6600
```

FIG. 25D

```
CTCATTCTGC TGTGCTGATG GTGATCATTA ACCCAACAGC TCATTAACCA GGTTATGGCT    6660
CAGGTGCGTG CTGCTGAACA AGCTTGGAGC CTAAAATGGT TCCTGCACAC ATCCCAGGGG    6720
ACGGCCCTCC ACCTTTCACT CCCCGCCATT ACAGCTCTCC TTAATCAGAG GAATACAGAT    6780
TCCATGCACT GAGTGCACTG AGCCATCGCC CACCTTCCCT ACAAACACCT CCTGGTCCCC    6840
ACAAACCCTC ACTGTGGGAA GAGGGGCTCT GGGGGGGTCA CAGGGACAAA CATTTAATAA    6900
TTCCTGTATT AATGGTTGAT TAACTTAAAA ATCTGTACTG ATCAAATAAA CTGCCACCCC    6960
TTGGGCATAG CTCAGAGCAT GCTCATGGAG TACAGCCCAC AGCTTTCCTC TGTGCTAGGG    7020
CAATGCTTCT CCTGGGTCCA TGTTCATCCT GGGTGGATGC AGAGCCCCAG GGTGGTACAT    7080
GAAACTGCAA TGGGATGTCA GTGTTCAGAG TTCTCCAACC GTCTGCCCCA TTGCCAAAGG    7140
GGTAAAGTTC CTCGGAGCAG ATTACCACAC CCTGGAGCTG GCAAAGGTT  GACGCTGGGC    7200
AAAGGTAGAA GCTGGGCATA GCTGCACGTT TCCTGCAGCT CAGGTGAGGG ATTTCTGTCT    7260
CTGTGGGGCT CCTTGTAGGG GAAATCCTTG GGGGGTCATC TGCTCTGCCT CACAGCCTGT    7320
GAGGAGCACT GGCACTGCCC AAGGCAGTGG                                     7350
```

FIG. 25E

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 525 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 1..525

(xi) SEQUENCE DESCRIPTION: SEQ ID NO:1:

```
GAC ATC AGA TGG ATC CAG CAG CGG TCC TCT CGG CTT GTG CAC CAC TAC      48
Asp Ile Arg Trp Ile Gln Gln Arg Ser Ser Arg Leu Val His His Tyr
 1               5                  10                  15

CGA AAT GGA GTG GAC CTG GGG CAC ATG GAG GAA TAT AAA GGG AGA ACA      96
Arg Asn Gly Val Asp Leu Gly His Met Glu Glu Tyr Lys Gly Arg Thr
```

|  |  |  |  |  |  |  |  |  |  | 20 |  |  |  |  | 25 |  |  |  |  | 30 |  |  |  |  |
|---|---|---|---|---|---|---|---|---|---|---|---|---|---|---|---|---|---|---|---|---|---|---|---|---|---|

```
GAA CTG CTC AGG GAT GGT CTC TCT GAT GGA AAC CTG GAT TTG CGC ATC        144
Glu Leu Leu Arg Asp Gly Leu Ser Asp Gly Asn Leu Asp Leu Arg Ile
             35                  40                  45

ACT GCT GTG ACC TCC TCT GAT AGT GGC TCC TAC AGC TGT GCT GTG CAA        192
Thr Ala Val Thr Ser Ser Asp Ser Gly Ser Tyr Ser Cys Ala Val Gln
         50                  55                  60

GAT GGT GAT GCC TAT GCA GAA GCT GTG GTG AAC CTG GAG GTG TCA GAC        240
Asp Gly Asp Ala Tyr Ala Glu Ala Val Val Asn Leu Glu Val Ser Asp
 65                  70                  75                  80

CCC TTT TCT ATG ATC ATC ATC CTT TAC TGG ACA GTG GCT CTG GCT GTG        288
Pro Phe Ser Met Ile Ile Ile Leu Tyr Trp Thr Val Ala Leu Ala Val
                 85                  90                  95

ATC ATC ACA CTT CTG GTT GGG TCA TTT GTC GTC AAT GTT TTT CTC CAT        336
Ile Ile Thr Leu Leu Val Gly Ser Phe Val Val Asn Val Phe Leu His
             100                 105                 110

AGA AAG AAA GTG GCA CAA GAG CAG AGA GCT GAA GAG AAA AGA TGC AGA        384
Arg Lys Lys Val Ala Gln Glu Gln Arg Ala Glu Glu Lys Arg Cys Arg
         115                 120                 125

GTT GGT GGA GAA AGC TGC AGC ATT GGA GAG AAA AGA TGC AGA GTT GGC        432
Val Gly Gly Glu Ser Cys Ser Ile Gly Glu Lys Arg Cys Arg Val Gly
 130                 135                 140

GGA ACA AGC AGC GCA ATC GAA GCA AAG AGA TGC AAT GTT GGA CAA ACA        480
Gly Thr Ser Ser Ala Ile Glu Ala Lys Arg Cys Asn Val Gly Gln Thr
145                 150                 155                 160

CGT TCT AAA CTG GAG GAA AGA CAG AGC AAG TGG AGA TTG GAA TTC            525
Arg Ser Lys Leu Glu Glu Arg Gln Ser Lys Trp Arg Leu Glu Phe
                 165                 170                 175
```

(2) INFORMATION FOR SEQ ID NO:2:

(i) SEQUENCE CHARACTERISTICS:
        (A) LENGTH: 523 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

```
GACATCAGAT GGATCCAGCA GCGGTCCTCT CGGCTTGTGC ACCACTACCG AAATGGAGTG      60

GACCTGGGGC AGATGGAGGA ATATAAAGGG AGAACAGAAC TGCTCAGGGA TGGTCTCTCT     120

GATGGAAACC TGGATTTGCG CATCACTGCT GTGACCTCCT CTGATAGTGG CTCCTACAGC     180

TGTGCTGTGC AAGATGGTGA TGCCTATGCA GAAGCTGTGG TGAACCTGGA GGTGTCAGAC     240

CCCTTTTCTA TGATCATCCT TTACTGGACA GTGGCTCTGG CTGTGATCAT CACACTTCTG     300

GTTGGGTCAT TTGTCGTCAA TGTTTTTCTC CATAGAAAGA AGTGGCACA GAGCAGAGAG      360

CTGAAGAGAA AAGATGCAGA GTTGGTGGAG AAAGCTGCAG CATTGGAGAG AAAAGATGCA     420

GAGTTGGCGG AACAAGCAGC GCAATCGAAG CAAAGAGATG CAATGTTGGA CAAACACGTT     480

CTAAAACTGG AGGAAAAGAC AGACGAAGTG GAGATTGGAA TTC                       523
```

(2) INFORMATION FOR SEQ ID NO:3:

(i) SEQUENCE CHARACTERISTICS:
        (A) LENGTH: 634 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:3:

```
CGGTGAACAG ATGGAGAGAA GGAATGCAAA GTTGGAGGCA GCAGCTGTAA AACTGGGACA      60

CAAAGCTAAA GAATCAGAGA AACAGAAATC GGAGCTGAAG GAGCGCCATG AGGAGATGGC     120

AGAACAAACT GAAGCAGTGG TGGTAGAAAC TGAAGAATAG GAAAAACCAT CTGAAGAATC     180

AGATTGAGAG ATGAACTGCG CCTCACAATA AGCACAGGAG TTAAGCTTCT TAGATCAATA     240

ACTGCACAGC ATACAAAACC ACAATAACTC AAACAGAGTA AGGAGGAGCC AGTGTTTGTG     300

TTGAGTGAGA ACACTGCAGT TCTGTCAGCC AAAGCTGCCT GAGGGACCGC CCAATTGAGG     360

GTGTGTGACC TCCAACTCAA ATCCAGTTGG AAGAAAGAAA CCATAGAAAG GAAGGAAAGG     420

GGAGGAAGAC AGAGATCCTG GAAGAGATAT GGGCATTTGG GGAAATAGTG TGATCATGTA     480

TCAGGCTTTG TGGACATCTA ATGAATATGT CATGCTTTTG TAACTACAAG CATGCACGCA     540

GAAACAAAGG TAGAAAACTG CTTTGGGTGT TAGCACTGTT CTCTGTCACT ATATAATAAA     600

GAATACCTGC TGATGGCAAT GGAACAAAAA AAAA                                634
```

(2) INFORMATION FOR SEQ ID NO:4:

(i) SEQUENCE CHARACTERISTICS:
        (A) LENGTH: 1785 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:

```
ATCCGTTCGA GCTCTCTCCT CCTACAGCTG CTGCCCTCAT ATTCTCCCCA CACTTCTTCC      60

CCATATTCTT TCCAAATCCT CTTCCCCATC TCCTCCACCG TCTCTTTCTC AGAGTCCTTC     120

CTCTCTCTCC CTAAATTCTT CCCCCCTCCT CTCCTCCAGC ACAGATGCGC TTCACATCGG     180

GATGCAACCA CCCCAGTTTC ACCCTCCCCT GGAGGACCCT CCTGCCTTAT CTCGTGGCTC     240

TGCACCTCCT CCAGCCGGGA TCAGCCCAGC TCAGGGTGGT GGCGCCGAGC CTCCGTGTCA     300

CTGCCATCGT GGGACAGGAT GTCGTGCTGC GCTGCCACTT GTGCCCTTGC AAGGATGCTT     360

GGAGATTGGA CATCAGATGG ATCCTGCAGC GGTCCTCTGG TTTTGTGCAC CACTATCAAA     420

ATGGAGTGGA CCTTGGGCAG ATGGAGGGAT ATAAAGGGAG AACAGAACTG CTCAGGGATG     480

GTCTCTATGA TGGAAACCTG GATTTGCGCA TCACTGCTGT GAGCACCTCC GATAGTGGCT     540

CATACAGCTG TGCTGTGCAG GATGGTGATG GCTATGCAGA CGCTGTGGTG GACCTGGAGG     600

TGTCAGATCC CTTTTCCCAG ATCGTCCATC CTGGAAGGT GGCTCTGGCT GTGGTCGTCA     660

CAATTCTCGT TGGGTCATTT GTCATCAATG TTTTTCTCTG TAGGAAGAAA GCGGCACAGA     720

GCAGAGAGCT GAGTGAGTCC TTCCAGCCCC TTCCACCACC AAAGTCCCTT TAATGGAACT     780

GATAGAAGAC TGCAGAGTGC TGGGTTTATG CCTTGTGCTG GGGCCATGGG ATCTATGGGA     840

CCTTGGGATG TGTTGGGGCC GTGGGATGTG CTGGGGTCGT GGGATCTGTC AACCCTGATT     900

GATCCACTTC AGAACTCTTG CCCAATCGGT TCCTTCCGAT TCATTTAACT CCTTCTTGAG     960

GCCAAAGTGG TCATTGGCCA CATCCCATAA AAAGGGTTT GGGGTCAGGG TGTGGGAGCT    1020

GATCGCATGG AAACGTGTCC CCTCTGACCA TGCATTTCAT TTGCTTCTAT TTTGCAGAGA    1080

GAAAAGATGC AGCGTTGGCG GAACTAGATG AGATATCGGG TTTAAGTGCT GAAAATCTGA    1140

AGCAATTAGC TTCAAAACTG AACGAAAATG CTGACGAAGT GGAGGATTGC AATTCAGAGC    1200

TGAAGAAAGA CTGTGAAGAG ATGGGTTCTG GCGTTGGAGA TCTGAAGGAA CTGGCTGCAA    1260
```

```
AATTGGAGGA ATATATTGCA GTGAATCGGA GAAGGAATGT AAAGTTGAAT AATATAGCTG      1320

CCAAACTGGC ACAACAAACT AAAGAATTGG AGAAACAGCA TTCACAGTTC CACAGACACT      1380

TTCAGCGTAT GGATTTAAGT GCTGTAAACC AGAAGAAACT GGTTACAAAA CTGGAGGAAC      1440

ACTTTGAATG GATGGAGAGA AGGAATGTAA AGTTGGAGAT ACCAGCTGTA ATACTGGGGC      1500

AACAAGCTAA AGAATCAGAG AAACAGAAAT CGGAGCTGAA GGAGCGCCAT GAGGAGATGG      1560

CAGAACAAAC TGAAGCAGTG GTGGTAGATA CTGAAGAAGC GGAAAAACCA TCTGAAGAAT      1620

TGGATTGAGA GATGAACTGC GCCTCACAGT AACCACAGGA GTTAAGCTTC ATAGATCAAT      1680

GACTGCACAG CATACAAAAA CCACGATACC TCAAACAGAG CAAGGAAATC CACAGCGAGA      1740

ACAAGAGGAG CCAGTGTTTG TGTTGAGTGA GAACACTGCA GTTCT                     1785

(2) INFORMATION FOR SEQ ID NO:5:

(i) SEQUENCE CHARACTERISTICS:
         (A) LENGTH: 1816 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:5:

TTCTGCCCTC ATATTCTCCC CACACTTCTT CCCCATATTC TTTCCAAATC CTCTTCCCCA        60

TCTCCTCCAT CGTCTCCTTC TCAGAGTCCT TCCTCTCTCT CCCTAAATTC TTCCCCCCTC       120

CTCTTCTCCA GCACAGATGG CCTTCACATC GGGCTGCAAC CACCCCAGTT TCACCCTCCC       180

CTGGAGGACC CTCCTGCCTT ATCTCGTGGC TCTGCACCTC CTCCAGCCGG GATCAGCCCA       240

GATCACGGTG GTGGCACCGA GCCTCCGTGT CACTGCCATC GTGGGACAGG ATGTTGTGCT       300

GCGCTGCCAC TTGTCCCCAT GCAAGGATGT TCGGAATTCA GACATCAGAT GGATCCAGCA       360

GCGGTCCTCT CGGCTTGTGC ACCACTACCG AAATGGAGTG GACCTGGGGC AGATGGAGGA       420

ATATAAAGGG AGAACAGAAC TGCTCAGGGA TGGTCTCTCT GATGGAAACC TGGATTTGCG       480

CATCACTGCT GTGACCTCCT CTGATAGTGG CTCCTACAGC TGTGCTGTGC AAGATGGTGA       540

TGCCTATGCA GAAGCTGTGG TGAACCTGGA GGTGTCAGAC CCCTTTTCTA TGATCATCCT       600

TTACTGGACA GTGGCTCTGG CTGTGATCAT CACACTTCTG GTTGGGTCAT TTGTCGTCAA       660

TGTTTTTCTC CATAGAAAGA AAGTGGCACA GAGCAGAGAG CTGAAGAGAA AAGATGCAGA       720

GTTGGTGGAG AAAGCTGCAG CATTGGAGAG AAAAGATGCA GAGTTGGCGG AACAAGCAGC       780

GCAATCGAAG CAAAGAGATG CAATGTTGGA CAAACACGTT CTAAAACTGG AGGAAAAGAC       840

AGACGAAGTG GAGAACTGGA ATTCAGTGCT GAAAAAAGAC AGTGAAGAGA TGGGTTATGG       900

CTTTGGAGAT CTGAAGAAAC TGGCTGCAGA ACTGGAGAAA CACTCTGAAG AGATGGGGAC       960

AAGGGATTTA AGTTGGAGC GACTAGCTGC CAAACTGGAA CATCAAACTA AGAATTGGA       1020

GAAACAGCAT TCACAGTTCC AGAGACACTT TCAGAATATG TATTTAAGTG CTGGAAAACA      1080

GAAGAAAATG GTTACAAAAC TGGAGGAACA CTGTGAATGG ATGGTGAGAA GGAATGTAAA      1140

GTTGGAGATA CCAGCTGTAA AAGTGGGGCA ACAAGCTAAA GAATCAGAGG AACAGAAATC      1200

GGAGCTGAAG GAGCACCATG AGGAGACGGG GCAACAAGCT AAAGAATCAG AGAAACAGAA      1260

ATCGGAGCTG AAGGAGCGCC ATGAGGAGAT GGCAGAACAA ACTGAAGCAG TGGTGGTAGA      1320

AACTGAAGAA TAGGAAAAAC CATCTGAAGA ATTGGATTGA GAGATGAACT GCGCCTCGCA      1380

GTAACCACAG GAGTTAAGCT TCATAGATCA ATAACTGCAC AGCATACAAA ACCACAATAA      1440
```

-continued

```
CTCAAACAGG GTAAGGAGGA GCCAGTGTTT GTGTTGAGTG AGAACACTGC AGTTCTGTCA      1500

GCCAAAGCTG CCTGAGGGAC CGCCCAATTG AGGGTGTGCG ACCTCCAACT CAAAGCCAAT      1560

TGGAAGAAAG AAACCATAGA AAGGAAGAAA AGGGGAGGAA GACAGAGATC CTGGAAGAGA      1620

TATGGGCATT TGGGGAAATA GTGTGACCAT GTATCAGGCT TTGTGGACAT CTAACGAATA      1680

TGTCATGTTT TTGTAAATAC AAGCATGCAC GCAGAAACAA AGGGAGAAAA CTGCTTTGGG      1740

TGTTAGCACT GTTCTCTGTC CCTATATAAT AAAGAATACC TGCTGATGGC AAAAAAAAAA      1800

AAAAAAAAAA AAAAA                                                       1816

(2) INFORMATION FOR SEQ ID NO:6:

(i) SEQUENCE CHARACTERISTICS:
        (A) LENGTH: 1822 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

AAATGAAGAC TTCAGGATCC TTCCATAAAA GCTATCAGTT TGACTTCAGA GAGGGCTATT        60

CTCGGTGTTT GCAAGAAGCT TTCCATCGTC TCCTTCTCAG AGTCCTTCCT CTCTCTCCCT       120

AAATTCTTCC CCCCTCCTCT TCTCCAGCAC AGATGGCCTT CACATCGGGC TGCAACCACC       180

CCAGTTTCAC CCTCCCCTGG AGGACCCTCC TGCCTTATCT CGTGGCTCTG CACCTCCTCC       240

AGCCGGGATC AGCCCAGATC ACGGTGGTGG CACCGAGCCT CCGTGTCACT GCCATCGTGG       300

GACAGGATGT TGTGCTGCGC TGCCACTTGT CCCCATGCAA GGATGTTCGG AATTCAGACA       360

TCAGATGGAT CCAGCAGCGG TCCTCTCGGC TTGTGCACCA CTACCGAAAT GGAGTGGACC       420

TGGGGCAGAT GGAGGAATAT AAAGGGAGAA CAGAACTGCT CAGGGATGGT CTCTCTGATG       480

GAAACCTGGA TTTGCGCATC ACTGCTGTGA CCTCCTCTGA TAGTGGCTCC TACAGCTGTG       540

CTGTGCAAGA TGGTGATGCC TATGCAGAAG CTGTGGTGAA CCTGGAGGTG TCAGACCCCT       600

TTTCTATGAT CATCCTTTAC TGGACAGTGG CTCTGGCTGT GATCATCACA CTTCTGGTTG       660

GGTCATTTGT CGTCAATGTT TTTCTCCATA GAAAGAAAGT GGCACAGAGC AGAGAGCTGA       720

AGAGAAAAGA TGCAGAGTTG GTGGAGAAAG CTGCAGCATT GGAGAGAAAA GATGCAGAGT       780

TGGCGGAACA AGCAGCGCAA TCGAAGCAAA GAGATGCAAT GTTGGACAAA CACGTTCTAA       840

AACTGGAGGA AAAGACAGAC GAAGTGGAGA ATTGGAATTC AGTGCTGAAA AAGACAGTG        900

AAGAGATGGG TTATGGCTTT GGAGATCTGA AGAAACTGGC TGCAGAACTG AGAAACACT        960

CTGAAGAGAT GGGGACAAGG GATTTAAAGT TGGAGCGACT AGCTGCCAAA CTGGAACATC      1020

AAACTAAAGA ATTGGAGAAA CAGCATTCAC AGTTCCAGAG ACACTTTCAG AATATGTATT      1080

TAAGTGCTGG AAAACAGAAG AAAATGGTTA CAAAACTGGA GGAACACTGT GAATGGATGG      1140

TGAGAAGGAA TGTAAAGTTG GAGATACCAG CTGTAAAAGT GGGGCAACAA GCTAAAGAAT      1200

CAGAGGAACA GAAATCGGAG CTGAAGGAGC ACCATGAGGA GACGGGGCAA CAAGCTAAAG      1260

AATCAGAGAA ACAGAAATCG GAGCTGAAGG AGCGCCATGA GGAGATGGAA CAAACTGAAG      1320

CAGTGGTGGT AGAAACTGAA GAATAGGAAA AACCATCTGA AGAATTGGAT TGAGAGATGA      1380

ACTGCGCCTC GCAGTAACCA CAGGAGTTAA GCTTCATAGA TCAATAACTG CACAGCATAC      1440

AAAATCACAA TAACTCAAAC AGGGTAAGGA GGAGCCAGTG TTTGTGTTGA GTGAGAACAC      1500

TGCAGTTCTG TCAGCCAAAG CTGCCTGAGG GACCGCCCAA TTGAGGGTGT GCGACCTCCA      1560
```

```
ACTCAAAGCC AATTGGAAGA AGAAACCAT  AGAAAGGAAG AAAAGGGGAG GAAGACAGAG    1620

ATCCTGGAAG AGATATGGGC ATTTGGGGAA ATAGTGTGAC CATGTATCAG GCTTTGTGGA    1680

CATCTAACGA ATATGTCATG TTTTTGTAAA TACAAGCATG CACGCAGAAA CAAAGGGAGA    1740

AAACTGCTTT GGGTGTTAGC ACTGTTCTCT GTCCCTATAT AATAAAGAAT ACCTGCTGAT    1800

GGCAATGGAA AAAAAAAAA AA                                              1822
```

(2) INFORMATION FOR SEQ ID NO:7:

(i) SEQUENCE CHARACTERISTICS:
        (A) LENGTH: 3134 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

```
ATCCGCTCGA GCTCTCTCCT CCTACAGTTT CTGCCCTCAT ATTCTCCCCA CACTTCTTCC      60

CCATATTCTT TCCAAATCCT CTTCCCCATC TCCTCCATCG TCTCCTTCTC AGAGTCCTTC     120

CTCTCTCTCC CTAAATTCTT CCCCCCTCCT CTTCTCCAGC ACAGATGGCC TTCACATCGG     180

GCTGCAACCA CCCCAGTTTC ACCCTCCCCT GGAGGACCCT CCTGCCTTAT CTCGTGGCTC     240

TGCACCTCCT CCAGCCGGGA TCAGCCCAGA TCACGGTGGT GGCACCGAGC CTCCGTGTCA     300

CTGCCATCGT GGGACAGGAT GTTGTGCTGC GCTGCCACTT GTCCCCATGC AAGGATGTTC     360

GGAATTCAGA CATCAGATGG ATCCAGCAGC GGTCCTCTCG GCTTGTGCAC CACTACCGAA     420

ATGGAGTGGA CCTGGGGCAG ATGGAGGAAT ATAAAGGGAG AACAGAACTG CTCAGGGATG     480

GTCTCTCTGA TGGAAACCTG GATTTGCGCA TCACTGCTGT GACCTCCTCT GATAGTGGCT     540

CCTACAGCTG TGCTGTGCAA GATGGTGATG CCTATGCAGA AGCTGTGGTG AACCTGGAGG     600

TGTCAGACCC CTTTTCTATG ATCATCCTTT ACTGGACAGT GGCTCTGGCT GTGATCATCA     660

CACTTCTGGT TGGGTCATTT GTCGTCAATG TTTTTCTCCA TAGAAAGAAA GTGGCACAGA     720

GCAGAGAGCT GAGTGAGTCC TTCCATCCCC ATCCACCAAC CAAAGTCCCT TTAATGGAAC     780

TGACAGCAGA CTGCAGAGTG CTGGGTTATG CCATGTGCTG GGGCCATGAG CTATGTTGAG     840

GCTTTGGAAT GTGTTGGGGT TGTGGGATGT ACTGGGGTCG TGGGATGTGT TATTCCTGGC     900

TGATTCACGT GGAAAAACCT TTCACAATCG GTTCCTTCCA GTTTGTTTAA TTCCTTCTTG     960

GGCCCAAAGT GGTCATTGGA CTCCTCCCAG AAAAAAGGGT TTGGGGTCAG GGTGTGAGAG    1020

CTGATGGCAC GGAAACGTGT CCCCTCTGAC CATGCATTTC ATTTGCTTCT ATTTTGCAGA    1080

GAGAAAAGAT GCAGAGTTGG GTAAGTCTCC TTCCCTAAAG CGAGGGAATT CAGGGTGTCC    1140

CCATGGCATC AGCCGTGGAA TTAGTAGCTG TCCTCTCTGA CAATTCACTG CTCTGCTCTT    1200

TCCTTTCCAG TGGAGAAAGC TGCAGCATTG GGTGAGTTAT ATTCCCCAAG CCAAAGTACT    1260

TTGGGTCTTC CCATTGGAAG TTATTTCCTC AGACCATCCT TTCTGTTGTG TTTGCTTTGG    1320

CATCATGTTA GTAAAATGCC TTCTTGGGAC CAAAGTGGTC ATTGGCCACT TCCCAGAAAA    1380

AAAGGTTTGG GGTCAGGGTG TGGGAGCTGA TGGCATGGAA ACATGTTCCC TCTGACCATG    1440

CATTTCCTTT GCTTCTTTTT CCAGAGAGAA AAGATGCAGA GTTGGCGGAA CAAGCAGCGC    1500

AATCGAGTGA GTCTCCCCCT CCATTTTTAT TATTTTTAAA TGTTCAGCCT CCGGTAGCTG    1560

TGGGATGAGA TGTTCCTCTC ATCATACACT GACTCTGCTT TTCCTTTGCA GAGCAAAGAG    1620

ATGCAATGTT GGACAAACAC GTTCTAAAAC TGGGTGAGTC CTCACTCCCA AATTATAAAG    1680
```

```
CAAAGGGTTC TGCCTGTGTG AGCTGTGGGA TCAGACGTTC CTCTCATCGT GCATTGCTTT      1740

TCTCTTTCTT TTTCAGAGGA AAAGACAGAC GAAGTGGAGA ATTGGAATTC AGTGCTGAGT      1800

AAGTTGCAGT CACTGAACTG AGGGAATGTG GGGTCTTCCT AAGGGACTGC GTAGGGGAGA      1860

AGTTCCCATG CACTGCTTTT CTCTTTCTTT TCCAGAAAAA GACAGTGAAG AGATGGGTTA      1920

TGGCTTTGGA GATCTGAGTA AGTCTCCCTC CCAACATGGA AGGAATTTAT GGTCTTAGCA      1980

TGGGATCAGC CATGGGATGA TCATCTGACC CCTCTCATCA TGCAATTCAT ATTTGTTCCT      2040

TTTGCAGAGA AACTGGCTGC AGAACTGGAG AAACACTCTG AAGAGATGGG GACAAGGGAT      2100

TTAAAGTTGG AGCGACTAGC TGCCAAACTG GAACATCAAA CTAAAGAATT GGAGAAACAG      2160

CATTCACAGT TCCAGAGACA CTTTCAGAAT ATGTATTTAA GTGCTGGAAA ACAGAGTAAG      2220

TCTCCCTCCC TGCACAGAAG GAACTTACGG TTTTCCCATG GGATCAGCCA TGGGACGATC      2280

ATCCGACTCT TCTCATCATG AATTTCGTCT TTCTTTCTTT TGCAGAGAAA ATGGTTACAA      2340

AACTGGAGGA ACACTGTGAA TGGATGGTGA GAAGGAATGT AAAGTTGGAG ATACCAGCTG      2400

TAAAAGTGGG GCAACAAGCT AAAGAATCAG AGGAACAGAA ATCGGAGCTG AAGGAGCACC      2460

ATGAGGAGAC GGGGCAACAA GCTAAAGAAT CAGAGAAACA GAAATCGGAG CTGAAGGAGC      2520

GCCATGAGGA GATGGCAGAA CAAACTGAAG CAGTGGTGGT AGAAACTGAA GAATAGGGTG      2580

AGTCTTTCCC AAACCAAAGC AATACGGGGT TTCCCATGGC ATGACAAGCT GTCCCACCTC      2640

AGCATCCGTT CCTTTTCTT TCTTTTCCAG AAAAACCATC TGAAGAATTG GATTGAGAGA       2700

TGAACTGCGC CTCGCAGTAA CCACAGGAGT TAAGCTTCAT AGATCAATAA CTGCACAGCA      2760

TACAAAACCA CAATAACTCA AACAGGGTAA GGAGGAGCCA GTGTTTGTGT TGAGTGAGAA      2820

CACTGCAGTT CTGTCAGCCA AAGCTGCCTG AGGGACCGCC CAATTGAGGG TGTGCGACCT      2880

CCAACTCAAA GCCAATTGGA AGAAAGAAAC CATAGAAAGG AAGAAAAGGG GAGGAAGACA      2940

GAGATCCTGG AAGAGATATG GGCATTTGGG GAAATAGTGT GACCATGTAT CAGGCTTTGT      3000

GGACATCTAA CGAATATGTC ATGTTTTTGT AAATACAAGC ATGCACGCAG AAACAAAGGG      3060

AGAAAACTGC TTTGGGTGTT AGCACTGTTC TCTGTCCCTA TAATAAAG AATACCTGCT       3120

GATGGCAAAA AAAA                                                      3134

(2) INFORMATION FOR SEQ ID NO:8:

(i) SEQUENCE CHARACTERISTICS:
        (A) LENGTH: 1449 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

CGATGTTCGG AATTCAGACA TCAGATGGAT CCAGCTGCGG TCCTCTAGGA TTGTGCACCA       60

CTACCAAAAT GGAGAGGACC TGGATCAGAT GGAGGAATAT GAAGGGAGAA CAGAACTGCT      120

CAGGGATGGT CTCTCTGATG GAAACCTGGA TTTGCGCATC ACTGCTGTGA GCTCCTCTGA      180

CAGTGGCTCG TACAGCTGTG CTGTGCAAGA TGATGATGGC TATGCAGAAG CTGTGGTGAA      240

CCTGGAGGTG TCAGATCCCT TTTCCCAGAT CGTCCATCCC TGGAAGGTGG CTCTGCCTGT      300

GGTCGTCACA ATTCTCGTTG GGTCATTTGT CATCATTGTT TTTCTCTATA GGAAGAAAGT      360

GGCACAGAGC AGAGAGCTGA AGGGAAAAGA TGCAGCACTG GCGGAACTAC CTGCGATATT      420

GGGTGTATGT ACTGCAAATT TGAAGATCCT AGCTTCAAAA CTGATGAAAC AAATGGAAAA      480
```

```
ATTGGAGATT CAGAATTCAC TCTTGAAGAA ACGGTATGAG ATTACGGAGG AACTGGCTGC     540

AGATCTGGAG GAACATCTTG CTGAGAAGGA TTTAAGCACT GCAGATCTGA AGCTACTAGC     600

TGCAAAACTG GTGGAACAAA GAGAAGCAGT GGAGGAACGG GATTCACAGC TGAGGAAACA     660

GTATGAAAAG TTGGGTTCGC GTGCTACAAA TCTGAAGACA CAACTTAAAA AGTTGGAGAA     720

CGAAATTGAA GAAGTGGAGA ACACCTTAA AAAGATTGGT ATACGTGCTC CTAATCTGAA      780

GCTACACATG GCAGAACTGG TGGATCAAGC TGAAGCAGTG GAGAAACGGA AATCAGAGCT     840

GAAGAGCTAT TTGACAAATA TAGGTTTACG TGCTGCAGAG CTGAAAAAAT ACATTGCAGC     900

ACTGGAGAAA CGAATTGAAG CATTGGAAAC TAAAGAATTG GAACAACCAT CTAAAGAACA     960

GGATTGAAAG ATGAACTGCG CCTCACAGTA ACCACAGGAG TTAAGCTTCA TAGACTGCAG    1020

ACTGCACAGG ATAGCAACAT CGCCATAACG CAAAGCAAGC AAGGAAATCC ACACGGGGAA    1080

CAAGAGGAGC CAGTGTTTGT ATTGAGTGAG AACACTGCAG TTCTGCAAGC CACAGCTGCC    1140

TGAGGGACCA GCAAACTGAG GGTGTGTGAC CTCCATCTCA AATCCAGTTG AAGAAAGAC     1200

ACCATAGAAA AGAAGACTAC AAGAGGAAGA CAGAGATCCT GGAAAAGGGA CAGACATTTT    1260

GGGAATGAAC ATGGCCATGT ATCAGGGTTT GAGGAATTCT AATGAATATG TAAGGCTTCT    1320

GGAAATATAA ACATGCACAC AGAAGTAAAG GTAGAAAACT GCTTTGGGTG TTAACACTGT    1380

TCTCTATCAC AATATAATAA AGAAATACCT GCTGATGGCG ATGGAAAAGA AAAAAAAAA     1440

AAAAAAAA                                                            1449

(2) INFORMATION FOR SEQ ID NO:9:

(i) SEQUENCE CHARACTERISTICS:
        (A) LENGTH: 2217 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 252..821

(ix) FEATURE:
        (A) NAME/KEY: CDS
        (B) LOCATION: 1165..1647

(xi) SEQUENCE DESCRIPTION: SEQ ID NO:9:

GCTCCTTCTG CATATTCTTC CTGAACTTTT TCTAAATCTT CTTTCCAGAT CTTCTTCCCC      60

ATCTGCTCCA GCACCTCCTC CTTGTATCCC CTTCCCCAAT CTTCCCTTCC CCACCTCCTT     120

CTCCTATCAT CTCTCATCTT TTACCCATTT TCTACCCACC TTCTGCCCCA TCTCCTCCAT     180

CATCTCCTTC TCAGTCTCCT TCCTCTCTCT CCTTTCCCCA ACTCCTCCCC CCTCCTCTT      240

CTCCAGCACA G ATG CAC TTC ACA TCG GGC TGC AAC CAC CCC AGT TTC ACC      290
             Met His Phe Thr Ser Gly Cys Asn His Pro Ser Phe Thr
               1               5                  10

CTC CCC TGG AGG ACC CTC CTG CCT TAT CTC ATG GCT CTG CAC CTC CTC       338
Leu Pro Trp Arg Thr Leu Leu Pro Tyr Leu Met Ala Leu His Leu Leu
     15                  20                  25

CAG CCG GGA TCA GCC CAG CAA AGG GTG GTG GCA CCG AGC CTC CGT GTC       386
Gln Pro Gly Ser Ala Gln Gln Arg Val Val Ala Pro Ser Leu Arg Val
 30              35                  40                      45

ACT GCC ATC GTG GGA CAG GAT GTT GTG CTG CGC TGC CAG TTG TCC CCT       434
Thr Ala Ile Val Gly Gln Asp Val Val Leu Arg Cys Gln Leu Ser Pro
             50                  55                  60
```

```
TGC AAG GAA GCT TGG AGA TCA GAC AAC AGA TGG ATC CAG CTG CGG TCC      482
Cys Lys Glu Ala Trp Arg Ser Asp Asn Arg Trp Ile Gln Leu Arg Ser
            65                  70                  75

TCT CGG CTT GTG CAC CAC TAT CAA TAT GGA TTG GAC CTG GGG CAG ATG      530
Ser Arg Leu Val His His Tyr Gln Tyr Gly Leu Asp Leu Gly Gln Met
        80                  85                  90

GAG GAA TAT AAA GGG AGG ACA GAA CTA CTC AGG AAG GGT CTC TCT GAT      578
Glu Glu Tyr Lys Gly Arg Thr Glu Leu Leu Arg Lys Gly Leu Ser Asp
    95                  100                 105

GGA AAC CTG GAT TTG CGC TTC ACT GCT GTG AGC ACC TCC GAT AAT GGC      626
Gly Asn Leu Asp Leu Arg Phe Thr Ala Val Ser Thr Ser Asp Asn Gly
110                 115                 120                 125

TCA TAC AGC TGT GCT GTG CAA GAT GAT GAT GGC TAC GGA GAC GCT GTT      674
Ser Tyr Ser Cys Ala Val Gln Asp Asp Asp Gly Tyr Gly Asp Ala Val
                130                 135                 140

GTG GAG CTG GAG GTG TCA GAT CCC TTT TCC CAG ATC GTC CAT CCC TGG      722
Val Glu Leu Glu Val Ser Asp Pro Phe Ser Gln Ile Val His Pro Trp
            145                 150                 155

AAG GTG GCT CTG GCT GTG GTT GTC ACA ATT CTG GTT GGG TCA TCT GTC      770
Lys Val Ala Leu Ala Val Val Val Thr Ile Leu Val Gly Ser Ser Val
        160                 165                 170

ATC AAT GTT TTT CTC TAT AGA AAG AAA GCT GCA CAG AGC AGA GAG CTG      818
Ile Asn Val Phe Leu Tyr Arg Lys Lys Ala Ala Gln Ser Arg Glu Leu
    175                 180                 185

AGT GAGTCCTTCC AGCACCTTCC ACCACCAAAG TCCCTTTAAT GGAACTGATA           871
Ser
190

GAAGACTGCA GAGTGCTGGG TTTATGCCAT GGGCTGGGGC TGTGGGATCT TTGGGGCTTG    931

GGATGTGTTG GGGCCGTGGG ATGTGCTGGG GTCGTGGGAT CTGTCAATCC TGATTGCTCC    991

TCTTCAGAAC TCTTGCCCAA TCGGTTCCTT CCGATTCATT TAACTCCTTC TTGGACCAAA   1051

GTGGTCATTG GCCTCTTACT AGAAAGAAAA GATTTGGGGT CTGGGTATGG GAGCAGCCAT   1111

GGGATGAGAA GGTGTTCCCT CTGACCATAC ATTTCTTTTG CTTCTATTTT GCA GAG      1167
                                                            Glu
                                                            1

AGA AAA GAT GCA ATG TTG GGT CCC GGT GCT GAA AAG CTG AAG AAA TTA     1215
Arg Lys Asp Ala Met Leu Gly Pro Gly Ala Glu Lys Leu Lys Lys Leu
            5                   10                  15

GCT TCA AAA CTG AAC GAA AAT GCT GAC GAA GTG GAG AAT TGC AAT TTA     1263
Ala Ser Lys Leu Asn Glu Asn Ala Asp Glu Val Glu Asn Cys Asn Leu
        20                  25                  30

GAG CTG AAA AAA GAC TGT GAC GAG ATG AGT TCT GCC GTT GCA GAT CTG     1311
Glu Leu Lys Lys Asp Cys Asp Glu Met Ser Ser Ala Val Ala Asp Leu
    35                  40                  45

AAG AAA TTG GCT GCA GTG ATT TGG ATA TGG GAT TTA AAG TTG TAT AAT     1359
Lys Lys Leu Ala Ala Val Ile Trp Ile Trp Asp Leu Lys Leu Tyr Asn
50                  55                  60                  65

CTA GCT GCC AAA CTG GGA CAA CAA ACT AAA GAA CTG GAG GAA CAG CAT     1407
Leu Ala Ala Lys Leu Gly Gln Gln Thr Lys Glu Leu Glu Glu Gln His
            70                  75                  80

TCA CAG TTC CAG GGT CAC TTT CAG CAT ATG GAT TTA AGT GCT GTA AAA     1455
Ser Gln Phe Gln Gly His Phe Gln His Met Asp Leu Ser Ala Val Lys
        85                  90                  95

CAG AAG AAA CTG GTT ACA AAA CTG GAG GAA CAC TGT AAT CAG ATG GTG     1503
Gln Lys Lys Leu Val Thr Lys Leu Glu Glu His Cys Asn Gln Met Val
    100                 105                 110

AGA AGG AAT GTA AAG TTG GAG GCA GCA GCT GTA AAA CTG GGG CAA CAA     1551
Arg Arg Asn Val Lys Leu Glu Ala Ala Ala Val Lys Leu Gly Gln Gln
```

```
                115                 120                 125
GCT AAA GAA TCA GAG GAA CAG AAA TCG GAG CTG AAG GAG CGC CAT GAG      1599
Ala Lys Glu Ser Glu Glu Gln Lys Ser Glu Leu Lys Glu Arg His Glu
130                 135                 140                 145

GAG ATG GCA GAA CAA ACT GAA GCA GTG GTG GTA GAT ACT GAA GAA TAG      1647
Glu Met Ala Glu Gln Thr Glu Ala Val Val Val Asp Thr Glu Glu  *
                150                 155                 160

GGTGAGTCTT CCCCAAACCA AAGCAATACG GGGTTTCCCA TGGCATGACA AGCTGTCCCA    1707

CCTCAGCATC CGTTGCTTTT TATTTCTTTT CCAGAAAAAC CATCTGAAGA ATTGGATTGA    1767

GAGATGAACT GCGCCTCACA GTAACCACAG GAGTTAAGCT TCATAGATCA ATTACTACAC    1827

AGCATAAAAA ACCACGATTC CACAAACAGA GCAAGGAAAT CCACAGCGAG AACAAGAGGA    1887

GCCAGTGTTT GTGTTGAGTG AGAACACTGC AGTTCTGTGA GCCAAAGCTG CCTGAGGGAC    1947

CGCCGAACTG AGGGTGTGCG ACCTCCAACT CAAAGCAATT GGAAGAAAGA AACCATAGAA    2007

AGGAAGGAAA GGGGAGGAAG ACAGAGATCC TGGAAGAGAT ATGGGCATTT GGGGAAATAG    2067

TGTGACCATG TATCAGGCTT TGTGGACATC TAATGAGTAT GTAATGCTTA TGGAAGTAGA    2127

AGCATGCACG CAGAAACAAA GGTAGAAAAC TGCTTTGGGT GTTAACACTG TTCTCTGTCA    2187

CTATATAATA AAGAATACCT GCTGATGGCA                                    2217

(2) INFORMATION FOR SEQ ID NO:10:

(i) SEQUENCE CHARACTERISTICS:
        (A) LENGTH: 2188 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

AAAGGAGTGA GTTGTGTACA GGGGGGTTAA ATGCTTTATA GACAAGAAAG AAATTGCTCT      60

AAAAGAGACT TATTCATCAT CATCATCATC TTCCTCCTCC TCTTCTTCCT CTTCTTCGTC     120

CTCTTCATCC TCTTCGTCTT CGTCCTCATC TTCCTCTTCT TCCTTCTTCT TCTTGCTCTT     180

CTCGGCCTTG GCAACTACTT TTTTGCCTGC ATCAACCTTC CCTTTGGCCC GGTATGCAGC     240

GATATCCTTC TCAGTCTCCT TCCTCTCTCT CCTTGGCCCA ACTCCTCCCC CCTCCTCTTC     300

TCCAGCACAG ATGGCCTTCA CATCGAGCTG CAACCACCCC AGTTTCACCC TCCCCTGGAG     360

GACCCTCCTG CCTTATCTCG TGGCTCTGCA CCACCTCCAG CCGGGATCAG CCCAGCTCAG     420

GGTGGTGGCA CCGAGCCTCC GTGTCACTGC CATTGTGGGA CAGGACGTCG TCTGCGCTGT     480

CACTTGTCTC CTTGCAAGAA TGCTTGGAAT TCAGACATCA GATGGATCCA GCACCGTTCC     540

TCTAGGATTG TGCACCACTA CCAAGACGGA GTGGACCTGG AGCAGATGGA GGAATATAAA     600

GGGAGGACAG AACTGCTCAG GGATGGTCTC TCTGATGGAA ACCTGGATTT GCGCATCACT     660

GCTGTGAGCA CCTCTGATAG TGGCTCATAC AGCTGTGCTG TGCAGGATGA TGATGGCTAT     720

GCAGAAGCTT TGGTGGAGCT GGAGGTGTCA GATCCCTTTT CCCAGATCGT CCATCCCTGG     780

AAGGTGGCTC TGGCTGTGAT CGTCACAATT CTGGTTGGGT CATCGGTCAT CATTGTTTTT     840

CTCTGTAGAA AGAAAGAGAG AAAAGATGGA GAGTTGGCGG AACAAGCTGA ATACTGGAG      900

AGAAAAGATG CAATGTTGAC GGAACAAGCT GAAACACTGG AGAAAAAGA TGTAATGTTG      960

AAGGAACAAG CTATGATAGC GGAATCAAAT GCTGAAGATC TGAAGAAACT GGCTGCGAAA    1020

CTGGAGAAAC ACTCTGAAGA GATGGGGACA AGGGATTTAA AGTTGGATAA ATTAGCTGCC    1080
```

```
AAACTGGAAC ATCAAACTAA AGAATTGGAG AAACAGAAAT CGGAGCTGAA GAGTCACTTT   1140

CAGTATATGG ATTTCAATGC TGGAAAACAG AAGAAAATGG TTACAAAACT GGAGGAACAC   1200

TATGAATGGA TGGTGACAAG GAATGTAAAA TTGGAGATAC CAGCTATAAA AGTGGGGCAA   1260

CAAGCTAAAG AATCAGAGGA ACAGAAATCG GAGCTGAAGG AGCACCATGA GGAGATGGGG   1320

CAACAAGCTA AGAATCAGA GGAACAGAAA TCGGAGCTGA AGGAGCACCA TGAGGAGATG    1380

GGGCAACAAG CTAAAGAATC AGAGGAACAG AAATCGGAGC TGAAGGAGCA CCATGAGGAG   1440

ATGGGGCAAC AAGCTAAAGA ATCAGAGGAA CAGAAATCGG AGCTGAAGGA GCACCATGAG   1500

GAGATGGGGC AACAAGCTAA AGAATCAGAG GAACAGAAAT CGGAGCTGAA GGAGCACCAT   1560

GAGGAGATGG GGCAACAAGC TAAAGAATCA GAGGAACAGA ATCGGAGCT GAAGGAGCAC    1620

CATGAGGAGA TGGGCAACA AGCTAAAGAA TCAGAGGAAC AGAAATCGGA GCTGATGGTA    1680

GAAACTGAAG AAGCAGAAAA ACCATCTGAA GAATCAGATT GAGAGATGAA CTGCGCCTCC   1740

CAATAAGCAC AGGAGTTAAG CTTCATAGAT CAATGACTGT ACAGCAAACA AAACCACGA    1800

TAACTCAAAC AGAGCAAGGA AATCCACAGC GAGAACAAGA AGAGCCAGTG TTTGTGTTGA   1860

GTGAGAACAC TGCAGTTCTG TCAGCCAAAG CTGTCTGAGG GACCGCCAAA TTGAGGGTGT   1920

CGAACCTCCA ACTCAAAGCC AATTGGAAGA AGAAACCAT AGAAAGGAAG AAAAGGGGAG    1980

GGAGACAGAG ATCCTGGAAA AGATATGGGC ATTTGGGGAA ATAGTGTGAC CATGTATCAG   2040

GCTTTATGGA AATCTAACAA ATATGTCATG GTTTTGTAAA TACAAGCATG CACGCAGAAA   2100

CAAAGGTAGA AAACTGCTTT GGGTGTTAGC ACTGTTCTCT GTCCCTATAT AATAAAGAAT   2160

ACCTGCTGAT GGCAAAAAAA AAAAAAAA                                     2188

(2) INFORMATION FOR SEQ ID NO:11:

(i) SEQUENCE CHARACTERISTICS:
         (A) LENGTH: 1487 base pairs
         (B) TYPE: nucleic acid
         (C) STRANDEDNESS: double
         (D) TOPOLOGY: linear (ii) MOLECULE TYPE: DNA (genomic)

(xi) SEQUENCE DESCRIPTION: SEQ ID NO:11:

TTGCAAGAAT GCTTGGAGCT TAGATATCAG ATGGATCCAG CTGCGGTCCT CTGGTTTTGT     60

GCACCACTAC CGAAATGGAG AGGACCTGGA GCAGATGACA GAATATAAAG GGAGAACAGA    120

ACTGCTCAGG AAGGGTCTTT CTGATGGAAA CCTGGATTTG CGCATCACTG CTGTGAGCAC    180

CTCCGATAGT GGCTCATACA GCTGTGTTGT GCAAGACGAT GATGGCTATG CAGAAGCGTT    240

GGTGGAGCTG GAGGTGTCAG ATCCCTTTTC CCAGATCGTC CATCCCTGGA AGGTGGCTCT    300

GGCTGTGATC GTCACAATTC TGGTTGGGTC ATTTGTCATC ATTGCTTTTC TCTATAGGAA    360

GAAAGCGACA CAGAGCAGAG AGCTGAAAAG AAAAGATGCA ATGTTGGGAA GAAAAGATGC    420

AGTGCTGGAG GAACTACCTG CGATATTAGA TTCAAGTGCT GCAAATCTGA AGATACTAGC    480

TTCAAAACTG GTGAAACAAA CTGAAAAATT GGACATACG AATTCACTAA TGAAGAAACA    540

GTATGAAATG ACAGAGAAAC AAGCTGCAGA ACTGGAGAAA CACTTAATAA ATACCGATTT    600

AAGTGCTGCA GATCTGAAGA TAGCAGCTGC AAAACTGGAC AAACAAACTG AAGAACTGGA    660

CAAATGGAAA TCAGCACTGA AGATACAATA TGAAAGTTG GGTTTACGTG CTGCAAATCT     720

GAAGACACAA GTTACAGAAC TGGCGAAACA AACTGAAGAA GTGGAAAATC ACTATGAAGA    780

GATGGGTTTA CGTGCTCCTA ATCTGAAGAA AAATATAGTA GAACTGGAGA AACAAACTGA    840
```

```
GCACGTGGAC AATCGGAAAT CAGAGCTGAA GAAACAGTAT GAAAATTTGG CTTCACATGC    900

TTCAGAGCTG AAGAAACAAG CTGAAGTACT GGAGGAACAA GCTGAACAAC TGGAGATTCA    960

GAATTCACTG TTGAAGATAC GCAATAAACA TAGGGAGAGA AAGAATGAAA TGTTGGAGAA   1020

ACAAACTGTA GAACAGGAAC AAACTGAAGA ATGGGCAGAA TCTAAAAAAT CGGTGGTTGA   1080

AACTAAAGAA TTGAACAAC CATCTAAAGA ACAGGATTGA GAGATGAACT GCGCCTCACA    1140

GTAACCACAG GAGTTAAGCT TCATGGACTG CTGACTGCAC AGGATAGCAA CACCGCCATA   1200

ATGCAAAGCG AGCAAGGAAA TCCACAGCGA AACAAGAGG AGCCAGTGTT TGTGTTGAGT    1260

GAGAACACTG CAGTTCCATG AGCCAAACCT GCCTGAGGGA CCGCCCAATT GAGGGTGTGC   1320

GACCTCCAAC TCAAAGCCAA TTGGAAGAAA GAAACCATAG AAAGGAAGAC TACAAGAGGA   1380

AGACAGAGAT CCTGGAAAAG GGATAGACAT TTTGGGATTT AACATGGCCA TGTATCAGGG   1440

TTTGAGGAAT CTAACGTAT ATATAAGGCT TTTGGAAATA TAAACAT                 1487

(2) INFORMATION FOR SEQ ID NO:12:

(i) SEQUENCE CHARACTERISTICS:
        (A) LENGTH: 4757 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

GGATGATCAT CCGACTCTTC TCATCATAAA TTCGTCTTCT TCTTTGCAGA GAAACTGGTT     60

ACAAAACTGG GTGAGTCCAA CCTCCCAAAC TAAATTAAAA GCAGTCAGAC TTTGTGAGCT    120

GTGGGATGAG ACGTTCTTCT CATCATGTGC TGCTTTCCTT TTACTTTTCC AGAGGAACAC    180

TTTGAATGGA TGGGTGAGTC TCCCCTCCCA AATTAAAAAT GTTGGGGTCT TCCTGTGTGA    240

GCTGTGGGAT GAGCTGTTCC TCCCATCATG CACTGGTTCT AATTTTCCTT TGCAGAGAGA    300

AGGAATGTAA AGTTGGGTGA GTCTTCTTCC CCAACCAAAG GGATTTGGGG TCTTCCATGG    360

GATCAGCCAT GGGATGATAA CCTGAACCTT ATCACATATT TCTTATTTGT TCTTTTTGCA    420

GAGATACCAG ATCTGTAATA CTGGGTGAGT CCTCCCTCCC AAATTAAATA CAAAAGGGGA    480

TCTGCCTGTG TGAGCTGTGG GATGAGATGT TCCTCTCATC ACGCATTATT TTCTCTTTCT    540

TTTCCAGGGC AACAAGCTAA AGAATCAGGT GAGTCTTCTT CCCTGTCCCA AAGGACTATG    600

GGTTTCCCAT GGGATGACAA GCTGTGCCAC CTCCTCACGA GGTGCTTCTT CTTTCTTTTT    660

TGCAGAGAAA CAGAAATCGG AGCTGAGTAA GTTGCAGTCA CTGAACTGAG GAATGTGGG    720

GTCTTCCCAA AGTCTTGTGT ATGGGATGAA AAATCCCCTC TGACCATGCA CTGCTTTTCT    780

CCTCCTTTGC CAGAGGAGCG CCATGAGGAG ATGGGTGAGT CTCCCCTCCC ATATTAAAAT    840

CGTTGGGGTC TTCCTGTGTG AGCTGTGAGA TGAGATGTTC CTCTCATCAT GCGATGCTTT    900

TCTCTCTTTT CCAGCAGAAC AAACTGAAGC AGTGGGTGAG TCTTTGTCCC CAACCCAAAG    960

GAATATGGGG CAATCCATGG GATGACAAGC TGTCCCATCT CATCGTGCAT TGCTTTCCTA   1020

TTCCTTTTTT CTAGTGGTAG ATACTGAAGA AGCGGGTGAG TCTTTCCCAA ACCAAAGCAA   1080

TACGGGGTTT CCCATGGCAT GACAAGCTGT CCCACCTCAG CATCCGTTGT TTTTCTCTTT   1140

CTTTTCCAGA AAAACCATCT GAAGAATTGG ATTGAGAGAT GAACTGCGCC TCACAGTAAC   1200

CACAGGAGTT AAGCTTCATA GATCAATGAC TGCACAGCAT ACAAAAACCA CGATACCTCA   1260

AACAGAGCAA GGAAATCCAC AGCGAGAACA AGAGGAGCCA GTGTTTGTGT TGAGTGAGAA   1320
```

```
CACTGCAGTT CTGTCAGCCA AAGCTGCCTG AGGGACCGCC AAACTGAGGG TGTGCGACCT    1380

CCAACTCAAA GCCAATTGGA AGAAAGAAAC CATAGAAAGG AAGGAAAGGG GAGGAAGACA    1440

GAGATCCTGG AAGAGATATG GGCATTTGGG GAAATAGTGT GACCATGTAT CAGGCTGTGT    1500

GGACATCTAA CGAATATGTC ATGTTTTTGT AAATACAAGC ATGCACTCAG AAACAAAGGT    1560

AGAAAACTGC TTTGGGTGGT AACACTGTTC TCTGTCAAAA TATAATAAAG AATACCTGCT    1620

GATGGTAATG GATCATTGAT TGTGAGCAGT TATTGGGGTT TGGTTCCATG AAACAGGCTG    1680

AGTCTTCTTC CCAGAAACAA AGCAACGTGG GCTCTATCGG ATAACAAGCC GACCCTTCTC    1740

ACCATGCACT GCTATTCCAG CACAACAAGG CTCTCTCCAG GAAGCTAAAA AGGGATAAAA    1800

TAAATTAATA GGAAAGAAAT ACACAAAAAC AAGAAAATTT AAAAAGAAT ACTCCAAAAA    1860

ATCTATAATT ATTACAATAA AAACTTTAAA AAAACACACC AACCTTCCAC CCTGGGGGAG    1920

CACCAATGAC AGCCTTTTGT GCCCCATCGC GGTTTTATGA GAACAGCCAC ACACTTCAGA    1980

GCTGACCCCG TGAGCCCCAC AGTGGGGGGA CCTCCCACAG TGGGTGGACC TCCTCCACAA    2040

CCACCCCCAT CACTCACATT GAATGCCCAA AGAAACAACA GCCCCAAAGG TTCCTCCTGG    2100

TGCTTCAGCC GCGTGTGTTC CTCATTCTGC TGTGCTGATG GTGATCATTA ACCCAACAGC    2160

TCATTAACCA GGTTATGGCT CAGGTGCGTG CTGCTGAACA AGCTTGGAGC CTAAAATGGT    2220

TCCTGCACAC ATCCCAGGGG ACGGCCCTCC ACCTTTCACT CCCCGCCATT ACAGCTCTCC    2280

TTAATCAGAG GAATACAGAT TCCATGCACT GAGTGCACTG AGCCATCGCC CACCTTCCCT    2340

ACAAACACCT CCTGGTCCCC ACAAACCCTC ACTGTGGGAA GAGGGGCTCT GGGGGGGTCA    2400

CAGGGACAAA CATTTAATAA TTCCTGTATT AATGGTTGAT TAACTTAAAA ATCTGTACTG    2460

ATCAAATAAA CTGCCACCCC TTGGGCATAG CTCAGAGCAT GCTCATGGAG TACAGCCCAC    2520

AGCTTTCCTC TGTGCTAGGG CAATGCTTCT CCTGGGTCCA TGTTCATCCT GGGTGGATGC    2580

AGAGCCCCAG GGTGGTACAT GAAACTGCAA TGGGATGTCA GTGTTCAGAG TTCTCCAACC    2640

GTCTGCCCCA TTGCCAAAGG GGTAAAGTTC CTCGGAGCAG ATTACCACAC CCTGGAGCTG    2700

GGCAAAGGTT GACGCTGGGC AAAGGTAGAA GCTGGGCATA GCTGCACGTT TCCTGCAGCT    2760

CAGGTGAGGG ATTTCTGTCT CTGTGGGGCT CCTTGTAGGG GAAATCCTTG GGGGGTCATC    2820

TGCTCTGCCT CACAGCCTGT GAGGAGCACT GGCACTGCCC AAGGCAGTGG TGGCTGTGCT    2880

CATGGAACTG ATGTTTGAGT GACCCCATCC CCTCCTCTCC TGGTGGCTGT AACCCTCTGG    2940

CCCCTCTCCT CCTACAGCTC CTTCCTGCAT ATTCTTCCTC AACTTTTTCT AAATCTTCTT    3000

TCCAAATCTT CTACCCCATC TGCTCCAGCA CCTCCTTCTC CATCTCCTTC CCCAAACTCC    3060

TCCTTATATC CCCTTCCCCA ATCTCCTTCA CCCACCTCCT TCTCCTATCA TCTTCTCTCA    3120

TCTTTTACCA TTTTCTACCC ACCTTCTGCC CCATCTCCTC CATCATATCC TTCTCAGTCT    3180

CCTTCCTCTC TCTCCTTTCC CCAACTCCTT CCCCCCTCCT CTTCTCCAGC ACAGATGGCC    3240

TTCACATCGA GCTGCAACCA CCCCAGTTTC ACCCTCCCCT GGAGGACCCT CCTGCCTTAT    3300

CTCGTGGCTC TGCACCACCT CCAGCCGGGA TCAGGTAGGG GTCCTGTGGG GCTGCTGTGC    3360

CTGGCACACG TGTTGCTATG GGGTGGGGA GCCGCCATGG GGCAGGGAGG ACACAAGTCC    3420

AGCCCCCAGC CCCACTTGGG TTTCACTTTC ACTTTGGTAA TTCCATGATA GATGCCATTT    3480

TGGGTAGAAT TTCTGTCTCT TCTTCACCTC TGCCACACGG TGTGAGTGGG CTCCCACCCC    3540

CAGCAATCCT TCCCCCTCTC TCCTGATCCC TCCCCACTGC TTTTACACCA GATGGAGCAC    3600

ACACCAACTC ACCCTGTGCC GCTCCATGCC CCCACATTAA CACAGACACC ATCTCACCAT    3660

CTCTCCGTGC CCTTCGCATT GCCCAGCCCA GCTCAGGGTG GTGGCACCGA GCCTCCGTGT    3720
```

```
CACTGCCATT GTGGGACAGG ACGTCGTCTG CGCTGTCACT TGTCTCCTTG CAAGAATGCT      3780

TGGAATTCAG ACATCAGATG GATCCAGCAC CGTTCCTCTA GGATTGTGCA CCACTACCAA      3840

GACGGAGTGG ACCTGGAGCA GATGGAGGAA TATAAAGGGA GGACAGAACT GCTCAGGGAT      3900

GGTCTCTCTG ATGGAAACCT GGATTTGCGC ATCACTGCTG TGAGCACCTC TGATAGTGGC      3960

TCATACAGCT GTGCTGTGCA GGATGATGAT GGCTATGCAG AAGCTTTGGT GGAGCTGGAG      4020

GTGTCAGGTC AGTGGCTGGG GTGACGTCTC CAGGTGTCCC TGGGTTTGTG GGTCCCACCC      4080

AACCTCTGTC CATCCTCATC CTCACGTCCA TGGATGGAGA GCTGAAGGAC AGCAGCCTTT      4140

GGAAGAGGTC AGGGCTGAAT TGTTTTATGA GATGCTGGAA TTAGAGCGGA CACACGGTGT      4200

GATTTGGGGA ATAGACTGCA TGGATGAGGT GGTTGGGTTG GATTTCTGGG ATGGGTTTCT      4260

CCATGTATCA GTGGCAGTGG GCACACGATG CTGAGCAGCT CCTCCGCCTG TGCCAATATG      4320

GGGACGCTGC CATTGTGTGT CACTGTTCCC TGCTCACTGC TCCTTCTGAA CAGGTGAATT      4380

CCGTTACCTT TTCCTTGGGA ACAGGACTAC AAAAAAGGTC TAGGGAAAAG GGTCTAGCAG      4440

GTAGGGACCT TCCACCGAGA CCGACACTAG CAGTGTTAAG ACCAACCCAG TAGCCAGTAG      4500

TAACAAAAAG AGACATCTTT CTTTCCACTC AACTCGTACC TCCCCTACCT CGTGTCCTTC      4560

CACAACACGT ACCTGTCCTT ACCAGCCCCA CCACGACTCG AGTCCAGGTG TCTCCATGTG      4620

TCCTCCTGCT TCCCTCTAAA AAGGACTCTA AGGGTCACGA GTAATTTATT GAAAAGGGAA      4680

AGAAAAACCC TTACTTCCTT CCTTTTTTTC CCCACACCCA CCCTTCTATC CTTACACCGA      4740

CATCCGTCCA CCTTTCA                                                    4757

(2) INFORMATION FOR SEQ ID NO:13:

(i) SEQUENCE CHARACTERISTICS:
        (A) LENGTH: 35 amino acids
        (B) TYPE: amino acid
        (C) STRANDEDNESS: single
        (D) TOPOLOGY: Not Relevant (ii) MOLECULE TYPE: peptide (v) FRAGMENT TYPE: N-terminal (xi) SEQUENCE DESCRIPTION: SEQ ID NO:13:

Pro Ala Val Lys Val Gly Gln Gln Ala Lys Glu Ser Glu Glu Gln Lys
1               5                   10                  15

Ser Glu Glu Met Gly Thr Arg Asp Leu Lys Leu Glu Arg Leu Ala Ala
            20                  25                  30

Lys Leu Glu
        35

(2) INFORMATION FOR SEQ ID NO:14:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:14:

Pro Ala Val Lys Leu Gly Gln Gln Ala Lys Glu Ser Gly Lys Gln Lys
1               5                   10                  15
```

```
Ser Ala Asn Ser Gly Val Ala Asp Leu Lys Glu Leu Ala Ser Glu Leu
            20                  25                  30

Tyr Asp Glu
        35

(2) INFORMATION FOR SEQ ID NO:15:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (v) FRAGMENT TYPE: N-terminal (xi) SEQUENCE DESCRIPTION: SEQ ID NO:15:

Pro Ala Val Ile Leu Gly Gln Gln Ala Lys Glu Ser Glu Glu Gln Lys
1               5                   10                  15

Ser Glu Gly Ser Gly Val Ala Asp Leu Lys Leu Ala Ala Lys Leu Glu
            20                  25                  30

Tyr Ile Ala
        35

(2) INFORMATION FOR SEQ ID NO:16:

(i) SEQUENCE CHARACTERISTICS:
        (A) LENGTH: 7350 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:16:
```

| | | | | | |
|---|---|---|---|---|---|
| CTGGGTCAGA | TCTCCCGGCT | TCATTTCTCT | CCATCCCTGG | GGTCCCCTCC | TCCCGTCTGA | 60 |
| CTGCTGGAGG | GCGGATGATC | ACCCCCTGTC | TGCACCCCTC | CCTGCGCTAT | CTGCAGCCCT | 120 |
| TCAGATGCAC | CGCACCCCAT | TTGCACTCCC | TGCCCCCCCT | TTGTACACAT | GGGGGGGATA | 180 |
| TCAGCCCTCC | TCCTTCCACC | CACCCGTATC | AGAGCCGCTG | TGCTGCTGAG | GGAGGCGGAT | 240 |
| GGGACGGCTG | CATCGCTCCC | CCTCAGCTTC | ACAGAGCTGC | TTTGCTGCGG | GTTTTGGCTG | 300 |
| CAATTCGGAC | CCTCTAAGAA | TGATCCCTCG | TTGTGAGACT | CCGCTGCAAA | GCTGATCCGT | 360 |
| TCGAGCTCTC | CTCCTACAGC | TGCTGCCCTC | ATATTCTCCC | CACACTTCTT | CCCCATATTC | 420 |
| TTTCCAAATC | CTCTTCCCCA | TCTCCTCCAC | CGTCTCTTTC | TCAGAGTCCT | TCCTCTCTCT | 480 |
| CCCTAAATTC | TTCCCCCCTC | CTCTCCTCCA | GCACAGATGC | GCTTCACATC | GGGATGCAAC | 540 |
| CACCCCAGTT | TCACCCTCCC | CTGGAGGACC | CTCCTGCCTT | ATCTCGTGGC | TCTGCACCTC | 600 |
| CTCCAGCCGG | GATCAGGTAG | GGGTCCTGTG | GGGCTGCTGT | GCCTGGCACA | GGTGTTGCTG | 660 |
| TGGGGTGGGG | GAGCAGCCAT | GGGGCAGGGA | GGACCCATGT | CCAGCACCCA | GCCTCGCTTG | 720 |
| GGTTTCTCTT | TCACTTGGGC | TATTTCATGA | AATGTGTGAT | TCGGGTGGA | ATTTCTGTCC | 780 |
| CTTCTTCACC | TCCACCACAC | GGTGTGAGTG | GGCTCCCACC | CCCAGCAATC | CTTGCCCACT | 840 |
| CCCTCCTGAT | CCCTCCCCAC | TGCTTTTACA | TGGGATGGAG | CACACACCAA | CTAACCCTGT | 900 |
| GCCGCTCCAT | GCCCCCACAT | TAACACAGCC | ACCATCTCAC | CATCTCTTCG | TGCCCTTCTC | 960 |
| ATTGCCCAGC | CCAGCTCAGG | GTGGTGGCGC | CGAGCCTCCG | TGTCACTGCC | ATCGTGGGAC | 1020 |
| AGGATGTCGT | GCTGCGCTGC | CACTTGTGCC | CTTGCAAGGA | TGCTTGGAGA | TTGGACATCA | 1080 |

```
GATGGATCCT GCAGCGGTCC TCTGGTTTTG TGCACCACTA TCAAAATGGA GTGGACCTGG    1140

GGCAGATGGA GGAATATAAA GGGAGAACAG AACTGCTCAG GGATGGTCTC TATGATGGAA    1200

ACCTGGATTT GCGCATCACT GCTGTGAGCA CCTCCGATAG TGGCTCATAC AGCTGTGCTG    1260

TGCAGGATGG TGATGGCTAT GCAGACGCTG TGGTGGACCT GGAGGTGTCA GGTCAGTGGC    1320

TGGGGTGATG TCTCCAGGTG TCCCTGGGCT TGTGTGTCCC CTACCGACCT CTGTCCATCC    1380

TCATCCTCAC ATCCTAGGAT GGAGAACTGA AGGACAGCAG CCTTTGGAAG AGCTCAGGGC    1440

TGAACAGCTC CATGAGATGC TGGAGTTGGA TCGGGCACAT GGTGTAATTT GAAAATGGAT    1500

ATGCATGGAT GAGGTGGTTG GGTTGGGTTT CTGGGATGGG TTTCTCCACG TCTCAGTGGC    1560

AGTGGGCACA CGATGCTGAG CAGCTCCTCC GCCTGTGCCA ATATGGGAC GCTGCCATTG     1620

TGTGTCACTG CTCCCTGGTT GTTGTCCCTT CGGGTTCTGT GATCTCCAGA AGTCGAAGTC    1680

GTGTTTGTCC ACATAAGGCA GTGGAAAAAG GAACCCTTGT CCTGATGTCT TTTCCAGATC    1740

CCTTTTCCCA GATCGTCCAT CCCTGGAAGG TGGCTCTGGC TGTGGTCGTC ACAATTCTCG    1800

TTGGGTCATT TGTCATCAAT GTTTTTCTCT GTAGGAAGAA AGGTGAGCTG AGAGCGGAGG    1860

GGATGGAGCA CAGGGAGGTG TTGTGCATGG ACAGGGATGG TCGGGGTGGT GCTGAGCTCT    1920

GGTGTACAGA GGTACACAGG AGGAGAAAGG GAGATTTTTC CTGACATTCC CACTGCCCAT    1980

TAAATAACAT TGCCTTTCTT TTGGGGAAAT GAAGGAGGAA AAAAGAAGT GTGGGTGGGC     2040

AGATAGGAAA GTGGGTGGAC CGTGGGGCAG GTGGAAAGGT CCAGACCTCG GGACGTCCCC    2100

AAACCAAGCT GCCCTGCTGA CTACCTCTTC CTCCAATTTG TTTTCCAGCG GCACAGAGCA    2160

GAGAGCTGAG TGAGTCCTTC CAGCCCCTTC CACCACCAAA GTCCCTTTAA TGGAACTGAT    2220

AGAAGACTGC AGAGTGCTGG GTTTATGCCT TGTGCTGGGG CCATGGGATC TATGGGACCT    2280

TGGGATGTGT TGGGGCCGTG GGATGTGCTG GGGTCGTGGG ATCTGTCAAC CTGATTGAT     2340

CCACTTCAGA ACTCTTGCCC AATCGGTTCC TTCCGATTCA TTTAACTCCT TCTTGAGGCC    2400

AAAGTGGTCA TTGGCCACAT CCCAGAAAAA AGGGTTTGGG GTCAGGGTGT GGGAGCTGAT    2460

CGCATGGAAA CGTGTCCCCT CTGACCATGC ATTTCATTTG CTTCTATTTT GCAGAGAGAA    2520

AACATGCAGC GTTGGGTAAG TCTCCTCCCC ATATGTGAGG GAATTCAGGG TGTCCCCATG    2580

GCATCAGCAG TGGGATGAGC AGCTGTCCGC TCTGACCATG CACTGCTCTG CTCTTTCTTT    2640

TCCAGCGGAA CTAGATGAGA TATCGGGTGA GTCTCCATTC CCAATTGTAT TCTTTCAAAT    2700

GTTCTGCCTT GGGGAGCTGT GGGATAGGAT GTTCTTCTCA CCATGCACTG ATTCTACCTT    2760

TCCATTGCAG GTTTAAGTGC TGAAAATCTG AGTAAGTGTC CCTCCTGACA CTGAAGGAAT    2820

TTGGGGTATT CCCATGGGAT CAGCCATTGA ATGAAAACAT GGCCCCCTCT CTTCATGCAT    2880

TTCCTATTTC TTACCTTTGC AGAGCAATTA GCTTCAAAAC TGAGTGAGTG CTCACTCCCA    2940

AACTCAAAGT AAAGAGAGTC TGCCTGTGTG AGCTGTGGGA TGAGATGTTC CACTCATCGT    3000

GCATTGCTTT TCTCTTTATT TTCCAGACGA AAATGCTGAC GAGTGGGTGA GTCTACATTC    3060

ACTAATGCAA AGAAATATGG GGTCTCCCAA GGGATGACAA GCGTGTCCCG CATCATCATT    3120

TGGTGCTTCT TCTGTCTTTT TTTTTGCAGA GGATTGCAAT TCAGAGCTGA GTAAGTTGCA    3180

GTCACTGAAC TGAGGGAATG TGGGGTCTTC CCAAGGGACA GTGCATGGGA TGAAAAATCC    3240

CCTCTGACCA TGCACTGCTT TTCTCTTTCT TTCCCAGAGA AAGACTGTGA AGAGATGGGT    3300

GAGTCCCCCC CCCCAAAATT AAACGTTGGG GTCCTCATGT GGAGCTGTGG ATGAGATGTC    3360

CTCTCATCAC GCACTGTTTC TACATTTCTT TGCAGGTTCT GGCGTTGCAG ATCTGAGTAA    3420

GTCTCCCCTA CCAGCACGGA AGGAATTTGT GGTCTTCCCA TGGGATCAGC CATGGGACTG    3480
```

```
ATCATCTGAG CCCTCTCATC ATGCATTTCA TATTCGTTCC TTTTGCAGAG GAACTGGCTG      3540

CAAAATTGGG TGAGTGTTGC CTCCCAAATT AAATTAAAAA AGGGGGTCTG CCTGGGCTCG      3600

CTGTGGGATA GGATCTTCCT CTCACTGTGT GTTGCTTTTC CCTTTCTTTT CCAGAGGAAT      3660

ATATTGCAGT GAATCGTGAG TCTCCCCTCC GAAATTATAA ATGCTGGGGA AATCTTGTGT      3720

GCGATCGTGG GTAGAGCTCT TCCTCTCATC ATGCACTGTT TCTGCTTTTC CTTTGCAGGG      3780

AGAAGGAATG TAAAGTTGAG TGAGTCTCTC TTCCCAAACC AAACAGATTT GGGGTCTTCC      3840

CATGGGATCA GCCATGGGAT GATAATCTAA CCCTACTCAT CATGCATTTC TTATTGGTTC      3900

CTTTGGCAGA TAATATAGCT GCCAAACTGG GTGAGTCCCC CCTCACAGAT TACATAAAAA      3960

ATGGGGTCTG CCTGTGTGAG CTGTGGGATG AGATGTTCCT CTCATCATGT ACTACTTTTC      4020

TCTTCCTTTT CCAGCACAAC AAACTAAAGA ATTGGGTGAG TCTTCTTTCC CCAAACAAAG      4080

AAATACGGGA TTCCCATGGG ATGACAAGCT GTGCCACCTC ATCATGCCCT GTTTTTCTG       4140

TCCTTTTTGC AGAGAAACAG CATTCACAGT TCCGTAAGTT GCAGTCACTA AACTGAAGGA      4200

ATGTGGGGTC TTCCCAAAGT CCTGCATACG GGATGAAAAA TCCCCTCTGA CCATGCACTG      4260

CTTTTCTCTT TCTATTCCAG ACAGACACTT TCAGCGTATG GGTGAGTCTC TCCCCCCCAA      4320

ATTAAAAACG CTGGGGGCAT CCTATGGGAG CTGTGGGATG AGATTTTCCT CTCATCACAC      4380

ACTCCTTCTG CTTTTCCATT GCAGATTTAA GTGCTGTAAA CCAGAGTAAG TCTCCCTCCC      4440

TGCACAGAAG GAACTTCCAG TTTTCCCATG GGATCAGCCA TGGGATGATC ATCCGACTCT      4500

TCTCATCATA AATTCGTCTT CTTCTTTGCA GAGAAACTGG TTACAAAACT GGGTGAGTCC      4560

AACCTCCCAA ACTAAATTAA AAGCAGTCAG ACTTTGTGAG CTGTGGGATG AGACGTTCTT      4620

CTCATCATGT GCTGCTTTCC TTTTACTTTT CCAGAGGAAC ACTTTGAATG GATGGGTGAG      4680

TCTCCCCTCC CAAATTAAAA ATGTTGGGGT CTTCCTGTGT GAGCTGTGGG ATGAGCTGTT      4740

CCTCCCATCA TGCACTGGTT CTAATTTTCC TTTGCAGAGA GAAGGAATGT AAAGTTGGGT      4800

GAGTCTTCTT CCCCAACCAA AGGGATTTGG GGTCTTCCAT GGGATCAGCC ATGGGATGAT      4860

AACCTGAACC TTATCACATA TTTCTTATTT GTTCTTTTTG CAGAGATACC AGCTGTAATA      4920

CTGGGTGAGT CCTCCCTCCC AAATTAAATA CAAAAGGGGA TCTGCCTGTG TGAGCTGTGG      4980

GATGAGATGT TCCTCTCATC ACGCATTATT TTCTCTTTCT TTTCCAGGGC AACAAGCTAA      5040

AGAATCAGGT GAGTCTTCTT CCCTGTCCCA AAGGACTATG GGTTTCCCAT GGGATGACAA      5100

GCTGTGCCAC CTCCTCACGA GGTGCTTCTT CTTTCTTTTT TGCAGAGAAA CAGAAATCGG      5160

AGCTGAGTAA GTTGCAGTCA CTGAACTGAG GGAATGTGGG GTCTTCCCAA AGTCTTGTGT      5220

ATGGGATGAA AAATCCCCTC TGACCATGCA CTGCTTTTCT CCTCCTTTGC AGAGGAGCG      5280

CCATGAGGAG ATGGGTGAGT CTCCCCTCCC ATATTAAAAT CGTTGGGGTC TTCCTGTGTG      5340

AGCTGTGAGA TGAGATGTTC CTCTCATCAT GCGATGCTTT TCTCTCTTTT CCAGCAGAAC      5400

AAACTGAAGC AGTGGGTGAG TCTTTGTCCC CAACCCAAAG GAATATGGGG CAATCCATGG      5460

GATGACAAGC TGTCCCATCT CATCGTGCAT TGCTTTCCTA TTCCTTTTTT CTAGTGGTAG      5520

ATACTGAAGA AGCGGGTGAG TCTTTCCCAA ACCAAAGCAA TACGGGGTTT CCCATGGCAT      5580

GACAAGCTGT CCCACCTCAG CATCCGTTGT TTTTCTCTTT CTTTTCCAGA AAAACCATCT      5640

GAAGAATTGG ATTGAGAGAT GAACTGCGCC TCACAGTAAC CACAGGAGTT AAGCTTCATA      5700

GATCAATGAC TGCACAGCAT ACAAAAACCA CGATACCTCA AACAGAGCAA GGAAATCCAC      5760

AGCGAGAACA AGAGGAGCCA GTGTTTGTGT TGAGTGAGAA CACTGCAGTT CTGTCAGCCA      5820
```

-continued

```
AAGCTGCCTG AGGGACCGCC AAACTGAGGG TGTGCGACCT CCAACTCAAA GCCAATTGGA   5880
AGAAAGAAAC CATAGAAAGG AAGGAAAGGG GAGGAAGACA GAGATCCTGG AAGAGATATG   5940
GGCATTTGGG GAAATAGTGT GACCATGTAT CAGGCTGTGT GGACATCTAA CGAATATGTC   6000
ATGTTTTTGT AAATACAAGC ATGCACTCAG AAACAAAGGT AGAAAACTGC TTTGGGTGGT   6060
AACACTGTTC TCTGTCAAAA TATAATAAAG AATACCTGCT GATGGTAATG GATCATTGAT   6120
TGTGAGCAGT TATTGGGGTT TGGTTCCATG AAACAGGCTG AGTCTTCTTC CCAGAAACAA   6180
AGCAACGTGG GCTCTATCGG ATAACAAGCC GACCCTTCTC ACCATGCACT GCTATTCCAG   6240
CACAACAAGG CTCTCTCCAG GAAGCTAAAA AGGGATAAAA TAAATTAATA GGAAAGAAAT   6300
ACACAAAAAC AAGAAAATTT AAAAAGAAT ACTCCAAAAA ATCTATAATT ATTACAATAA    6360
AAACTTTAAA AAAACACACC AACCTTCCAC CCTGGGGGAG CACCAATGAC AGCCTTTTGT   6420
GCCCCATCGC GGTTTTATGA GAACAGCCAC ACACTTCAGA GCTGACCCCG TGAGCCCCAC   6480
AGTGGGGGGA CCTCCCACAG TGGGTGGACC TCCTCCACAA CCACCCCCAT CACTCACATT   6540
GAATGCCCAA AGAAACAACA GCCCCAAAGG TTCCTCCTGG TGCTTCAGCC GCGTGTGTTC   6600
CTCATTCTGC TGTGCTGATG GTGATCATTA ACCCAACAGC TCATTAACCA GGTTATGGCT   6660
CAGGTGCGTG CTGCTGAACA AGCTTGGAGC CTAAAATGGT TCCTGCACAC ATCCCAGGGG   6720
ACGGCCCTCC ACCTTTCACT CCCCGCCATT ACAGCTCTCC TTAATCAGAG GAATACAGAT   6780
TCCATGCACT GAGTGCACTG AGCCATCGCC CACCTTCCCT ACAAACACCT CCTGGTCCCC   6840
ACAAACCCTC ACTGTGGGAA GAGGGGCTCT GGGGGGGTCA CAGGGACAAA CATTTAATAA   6900
TTCCTGTATT AATGGTTGAT TAACTTAAAA ATCTGTACTG ATCAAATAAA CTGCCACCCC   6960
TTGGGCATAG CTCAGAGCAT GCTCATGGAG TACAGCCCAC AGCTTTCCTC TGTGCTAGGG   7020
CAATGCTTCT CCTGGGTCCA TGTTCATCCT GGGTGGATGC AGAGCCCCAG GGTGGTACAT   7080
GAAACTGCAA TGGGATGTCA GTGTTCAGAG TTCTCCAACC GTCTGCCCCA TTGCCAAAGG   7140
GGTAAAGTTC CTCGGAGCAG ATTACCACAC CCTGGAGCTG GGCAAAGGTT GACGCTGGGC   7200
AAAGGTAGAA GCTGGGCATA GCTGCACGTT TCCTGCAGCT CAGGTGAGGG ATTTCTGTCT   7260
CTGTGGGGCT CCTTGTAGGG GAAATCCTTG GGGGGTCATC TGCTCTGCCT CACAGCCTGT   7320
GAGGAGCACT GGCACTGCCC AAGGCAGTGG                                    7350
```

RESTRICTION FRAGMENT LENGTH POLYMORPHISM TEST FOR HAPLOTYPING DOMESTICATED FOWL

This is a division of application Ser. No. 07/865,662 filed Apr. 7, 1992, issued as U.S. Pat. No. 5,451,670, which is a continuation of application Ser. No. 07/688,326 filed Apr. 22, 1991 (now abandoned), which is a continuation-in-part of Ser. No. 07/588,922 filed Sep. 27, 1990 now abandoned, which is a continuation-in-part of Ser. No. 07/210,405 filed Jun. 23, 1988 now abandoned, which is a continuation-in-part of Ser. No. 07/130,529 filed Dec. 9, 1987 (now abandoned), which is a continuation-in-part of Ser. No. 07/068,176 filed Jun. 30, 1987 (now abandoned) and which is a continuation-in-part of Ser. No. 07/413,301 filed Sep. 28, 1989 (now abandoned).

Each of applications Ser. Nos. 210,405; 130,529; 068,176; 413,301, and 588,922 is incorporated herein by reference.

FIELD OF THE INVENTION

This invention relates to restriction fragment length polymorphism pattern tests useful to genotype domesticated fowl for the major histocompatibility B-G loci. The invention also relates to the use of certain B-G polypeptides to impart immunity to or to control the susceptibility of domesticated fowl to various diseases.

BACKGROUND OF THE INVENTION

In domesticated fowl the major histocompatibility complex (MHC) which is associated with the regulation of immune recognition and immune response is called the B system. Resistance to Marek's disease is closely related to the domesticated fowl MHC. Resistance to other diseases, general fitness, and productivity also appear to be influenced to some extent by MHC haplotype.

MHC haplotyping of chickens is presently done by hemagglutination assay which relies on the production of specific antisera. The assay in itself is technically simple. However, the production of the antisera and the interpretation of the assays require a highly trained individual. The MHC haplotypes present in commercial strains of chickens are usually a trade secret known only to individual breeders. Isolation of cloned gene sequences from the B system provides a means of developing alternative methods for MHC haplotyping of birds and for determining the genotype at particular loci within the B system. The interpretation of results is generally simpler and more uniform since typing by restriction fragment length polymorphism patterns is no longer dependent upon alloantisera which often require selective absorptions with blood samples from genetically-defined animals to delineate haplotype specificity.

SUMMARY OF THE INVENTION

The B system of histocompatibility in domesticated fowl is known to contain three subregions which are identified as B-F, B-G and B-L. B-F, B-G and B-L are described as subregions because multiple genes of each type are present within the region of the B system. This invention includes cDNA clones encoding B-G antigens of the B system. MHC haplotyping is accomplished by use of novel probes provided by these clones to detect restriction fragment length polymorphism (RFLP) patterns typical for various B-G alleles present at the multiple loci within the B-G subregion.

Genetic recombination within the B system of the chicken is rare. For that reason, while the probes of this invention screen for the B-G genes, additional genes also of importance to disease resistance may be located in regions within and closely adjacent to the B system and genetically and physically linked to the B-G type. Other genes of mostly unknown function are located within the MHC as well.

A. Coomassie-blue stained SDS-8% polyacrylamide gel containing the following protein samples: 1 μg purified B-G21 antigen (lane 1); 40 μg of total cell protein from a λbg28 lysogen grown in the presence of IPTG (lane 2); 40 μg of total cell protein from a λgt11 lysogen grown in the presence of IPTG (lane 3); 40 μg of total cell protein from λbg28 lysogen grown in the absence of IPTG (lane 4); and protein size markers (marked MK) with their respective molecular weights given to the left in kilodaltons (kDa).

Figures 1A, 1B:
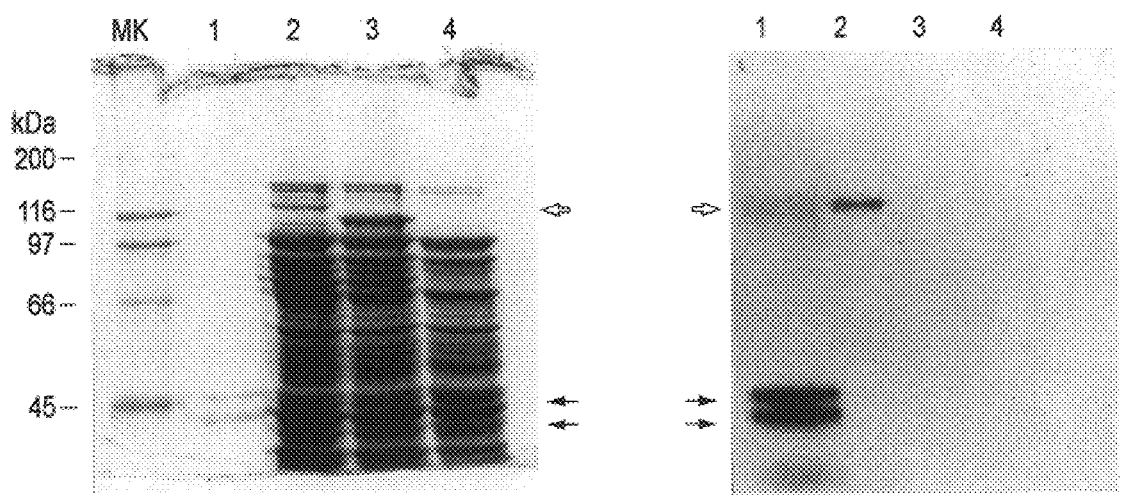
FIG. 1. Immunoblot of B-G21 antigen and λbg28 lysogen proteins reacted with antibodies specific to the bg28-β-galactosidase fusion protein.

B. Parallel immunoblot. The same protein samples were subjected to SDS-polyacrylamide gel electrophoresis as in FIG. 1A and then were electrophoretically transferred to a hybridization membrane. The proteins were reacted with B-G antigen-directed antiserum that had been affinity purified against bg28-β-galactosidase fusion protein. Bound antibodies were detected with $^{125}$I-Protein A and the above autoradiogram was the result of an overnight exposure with an intensifying screen at −70° C. The white arrowheads mark the position of the bg28-β-galactosidase fusion protein. The dark arrowheads mark the positions of the two polypeptides of B-G21 antigen.

FIG. 2. Northern analyses of poly(A)$^+$ RNA from embryonic tissues. Poly(A)$^+$ RNA samples (1 μg each) from the brain (BR), gizzard (GI), and erythrocytes B (ER) were subjected to formaldehyde agarose gel electrophoresis, transferred to a hybridization membrane, and hybridized with either $^{32}$P-labeled bg28 insert (A) or a $^{32}$P-labeled β-actin probe (B). The autoradiogram shown in (A) was the result of a 16-hour exposure the autoradiogram shown in (B) was the result of a 1-hour exposure. A 16-hour exposure of (B) revealed an actin mRNA species in the erythrocyte RNA sample (data not shown).

Figure 3:
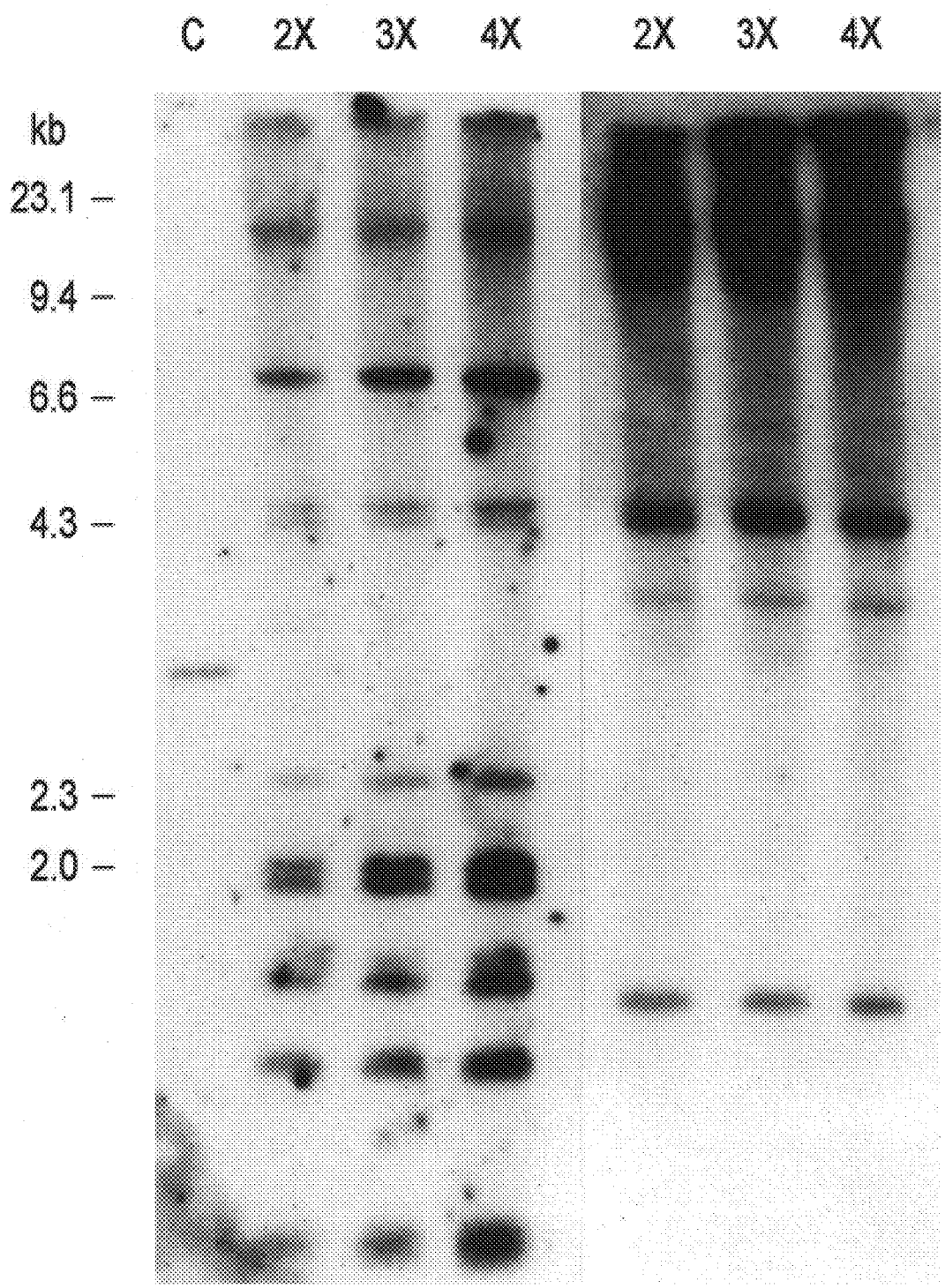

FIG. 3. Southern analyses of chicken genomic DNA from birds disomic, trisomic, or tetrasomic for the B system-bearing microchromosome. PvuII-digested genomic DNA (5 μg each) from chickens either disomic (2×), trisomic (3×), or tetrasomic (4×) for the B-complex microchromosome were subjected to electrophoresis on an 0.8% agarose gel and hybridized within the gel to either $^{32}$P-labeled λbg28 insert (left 4 samples) or a $^{32}$P-labeled β-actin probe (right 3 samples). The lane marked C contained 10 pg of HindIII-linearized Bluescript plasmid containing the bg28 insert. on the left are molecular size markers (in kilobase pairs) based on a HindIII digest of phage λ. The above autoradiograms were the result of an overnight exposure.

Figure 4:
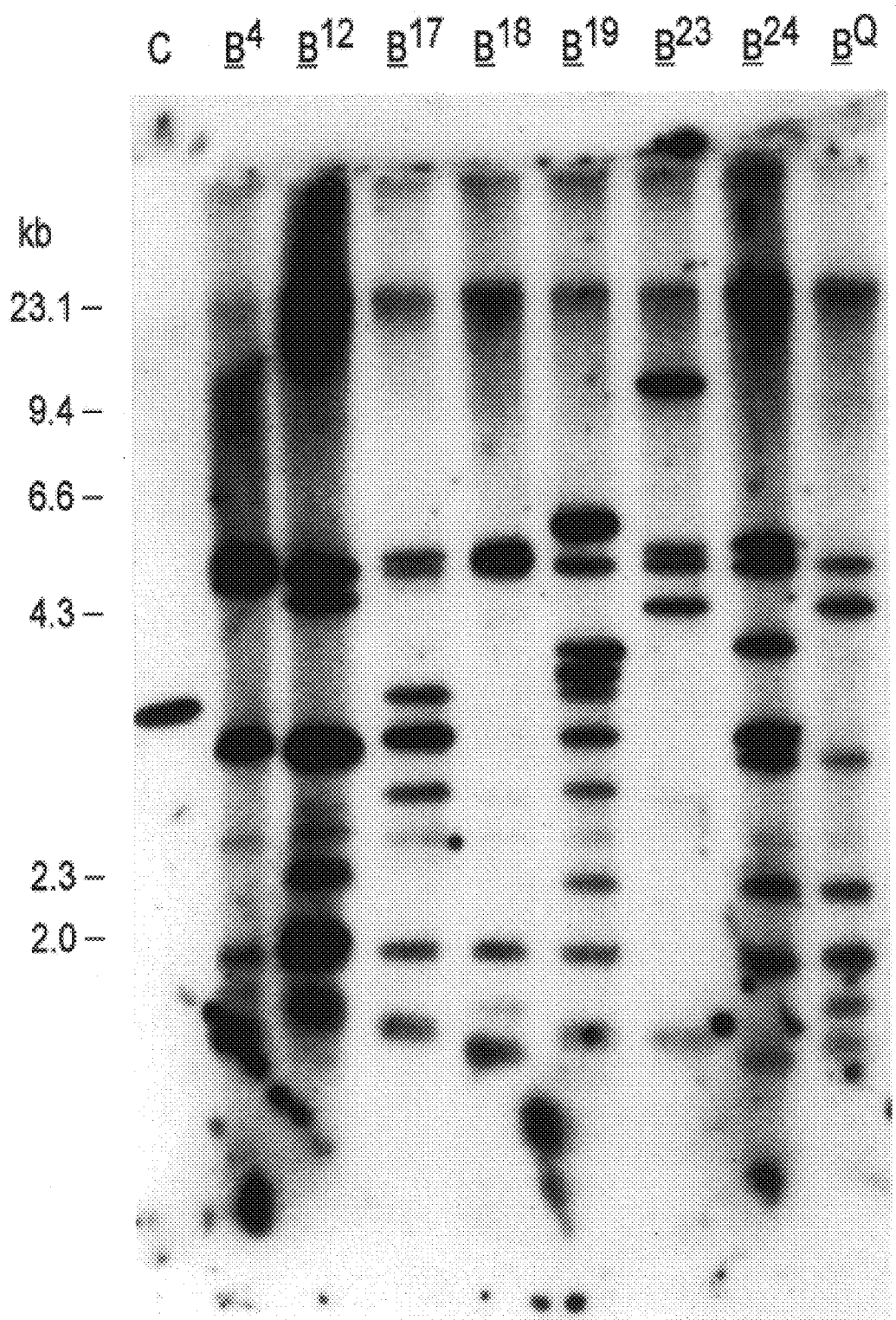

FIG. 4. Hybridization of the bg28 insert to restriction digests of chicken genomic DNA from birds of different B haplotypes. PvuII-digested genomic DNA (5 μg each) from chickens of different B haplotypes were subjected to electrophoresis on an 0.8% agarose gel and hybridized within the gel to $^{32}$P-labeled bg28 insert. DNA samples are labeled according to their respective B haplotype (see Table 1). The lane marked C contained 10 pg of HindIII-linearized Bluescript plasmid containing the bg28 insert. On the left are molecular size markers (in kilobase pairs) based on a HindIII digest of phage λ. The above autoradiogram was the result of an overnight exposure.

Figure 5:
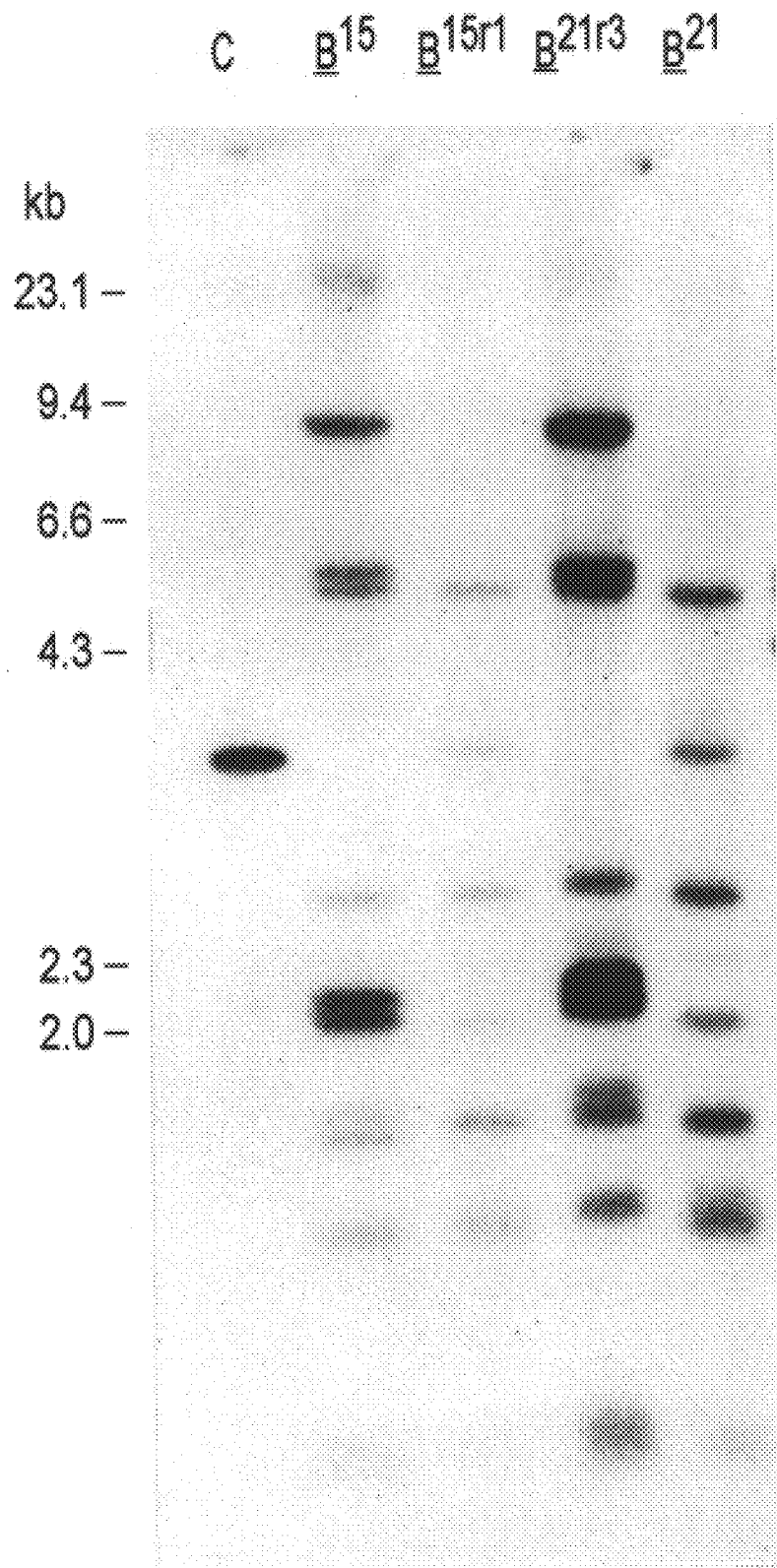

FIG. 5. Hybridization of the bg28 insert to restriction digests of chicken genomic DNA from birds of B-region recombinant haplotype. PvuII-digested genomic DNA (5 μg each) from chickens of either the parental $\underline{B}^{15}$ and $\underline{B}^{21}$ haplotypes or the recombinant $\underline{B}^{15r1}$ and $\underline{B}^{21r3}$ haplotypes were subjected to electrophoresis on an 0.8% agarose gel and hybridized within the gel to $_{32}$P-labeled bg28 insert. DNA samples are labeled according to their respective haplotype (see Table 1). The lane marked C contained 10 pg of HindIII-linearized Bluescript plasmid containing the bg28 insert. On the left are molecular size markers (in kilobase pairs) based on a HindIII digest of phage λ. The above autoradiogram was the result of an overnight exposure.

FIG. 6. SEQ ID NO: 1 Partial nucleotide sequence of the bg28 insert and the corresponding amino-acid sequence, determined by the dideoxy-chain-termination method of nucleotide sequencing on one strand only of bg28 cloned cDNA.

FIG. 7. SEQ ID NO: 2 Nucleotide sequence of the bg28 insert, determined by the dideoxy-chain-termination method of nucleotide sequencing of both strands of bg28 cloned cDNA.

Figure 8:
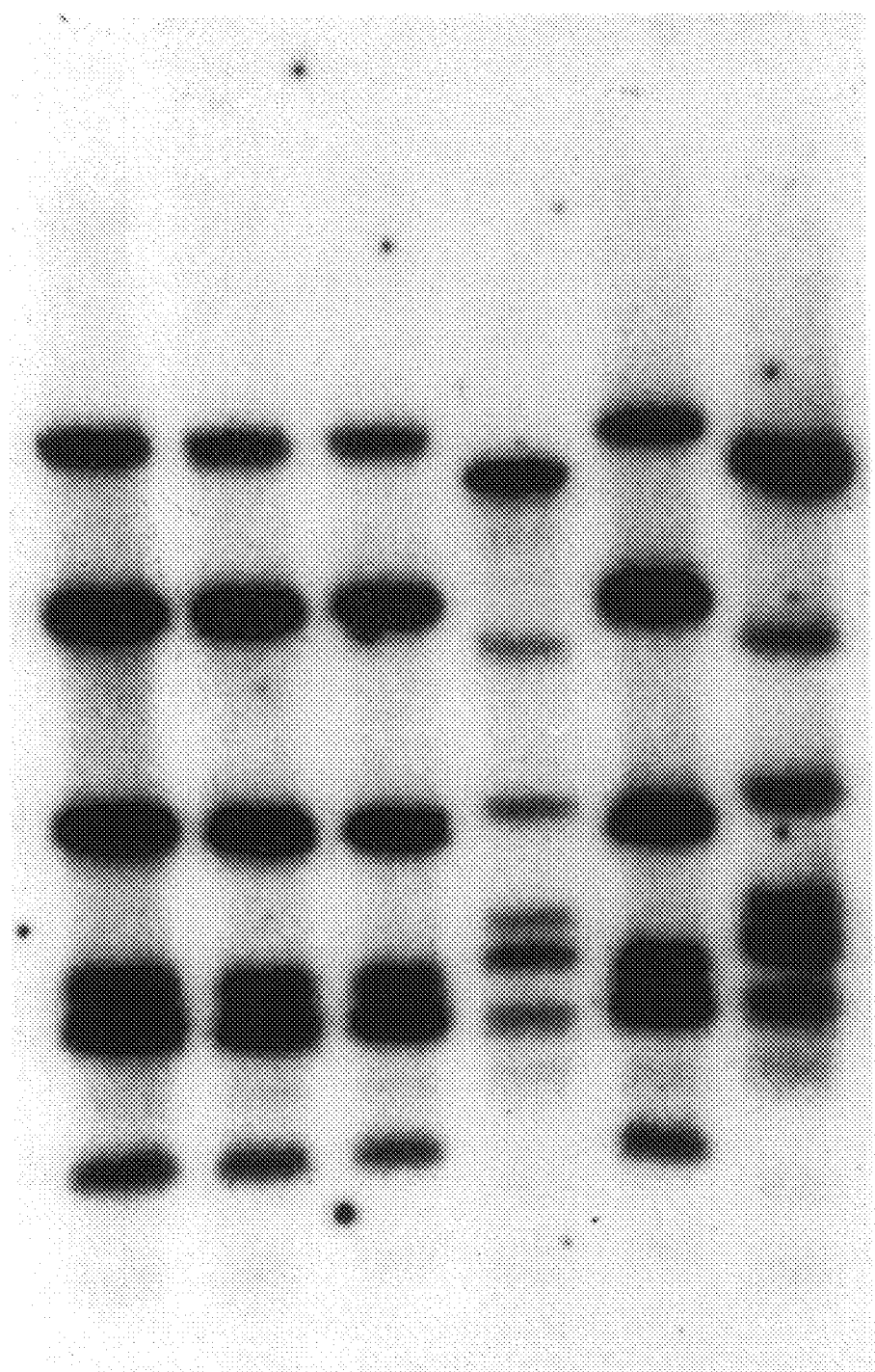

FIG. 8. Southern blot analyses of hybridization between bg32.1 and chicken genomic DNA. DNA samples are from birds of $\underline{B}^{15}$ haplotype disomic (2×), trisomic (3×) and tetrasomic (4×) for the $\underline{B}$ system-bearing microchromosome and from birds of $\underline{B}^{15r1}$, $\underline{B}^{21r3}$, and $\underline{B}^{21}$ haplotypes. Pvu II-digested genomic DNA samples (5 μg each) were subjected to electrophoresis in an 0.8% agarose gel and hybridized within the gel to $^{32}$P-labeled bg32.1 insert. On the left are molecular size markers (in kilobase pairs) based on a Hind III digestion of phage λ. The autoradiogram is the result of an overnight exposure.

Figure 9A:
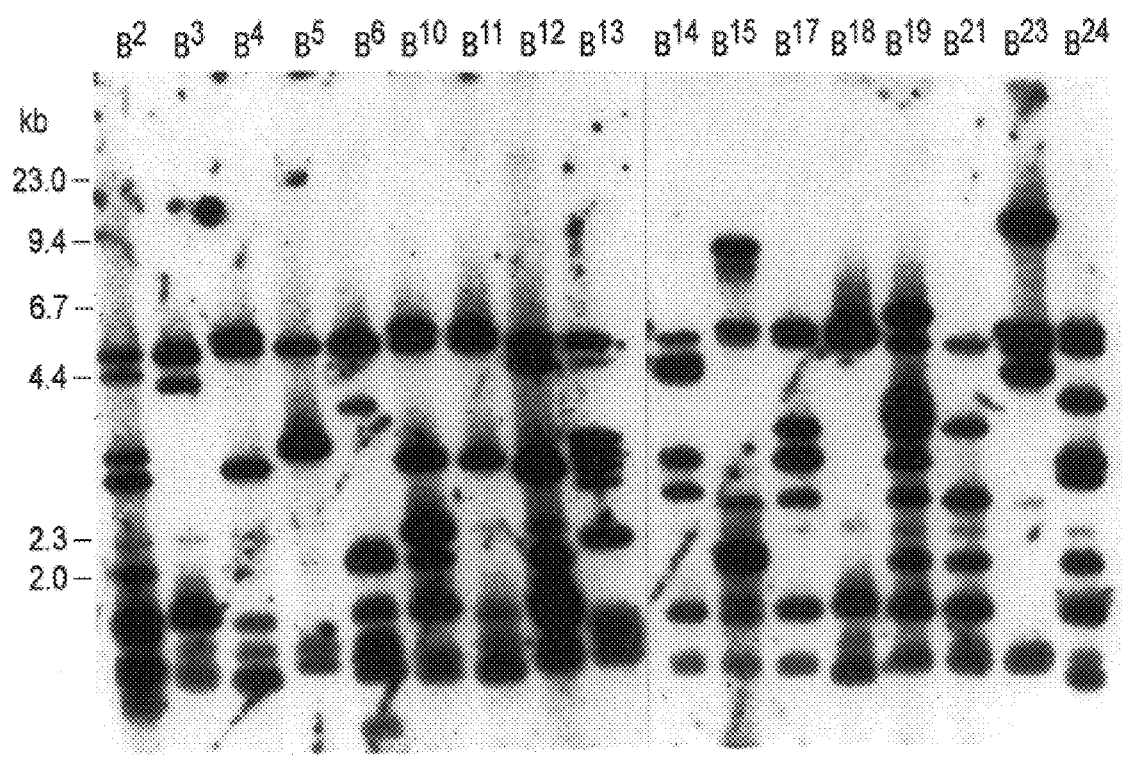
Figure 9B:
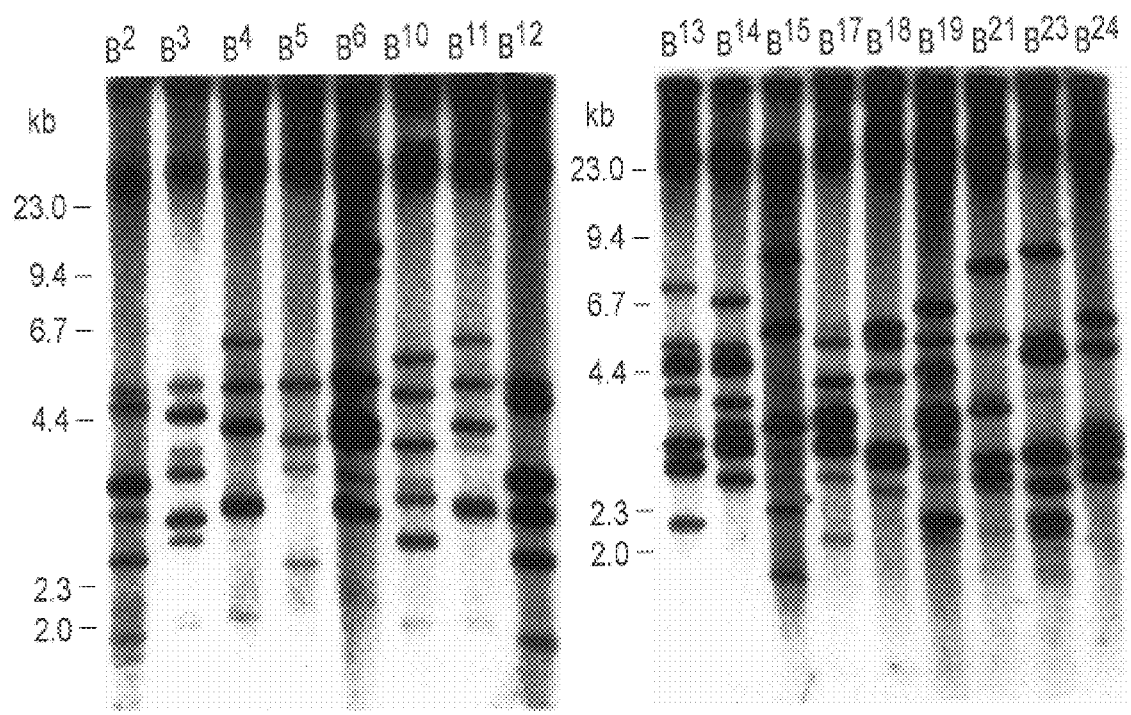

FIGS. 9A and 9B. Hybridization of the bg28 (A) and bg32.1 (B) probes to restriction digests of chicken genomic DNA from birds of 17 standard haplotypes. Pvu II-digested genomic DNA (5 μg each sample) were subjected to electrophoresis in an 0.8% agarose gel and hybridized within the gel to the $^{32}$P-labeled probes. DNA samples are labeled according to their respective $\underline{B}$ haplotype (see Table 3). Molecular size markers (in kilobase pairs) are based on a Hind III digestion of phage λ. The autoradiograms are the result of overnight exposures.

Figure 10:
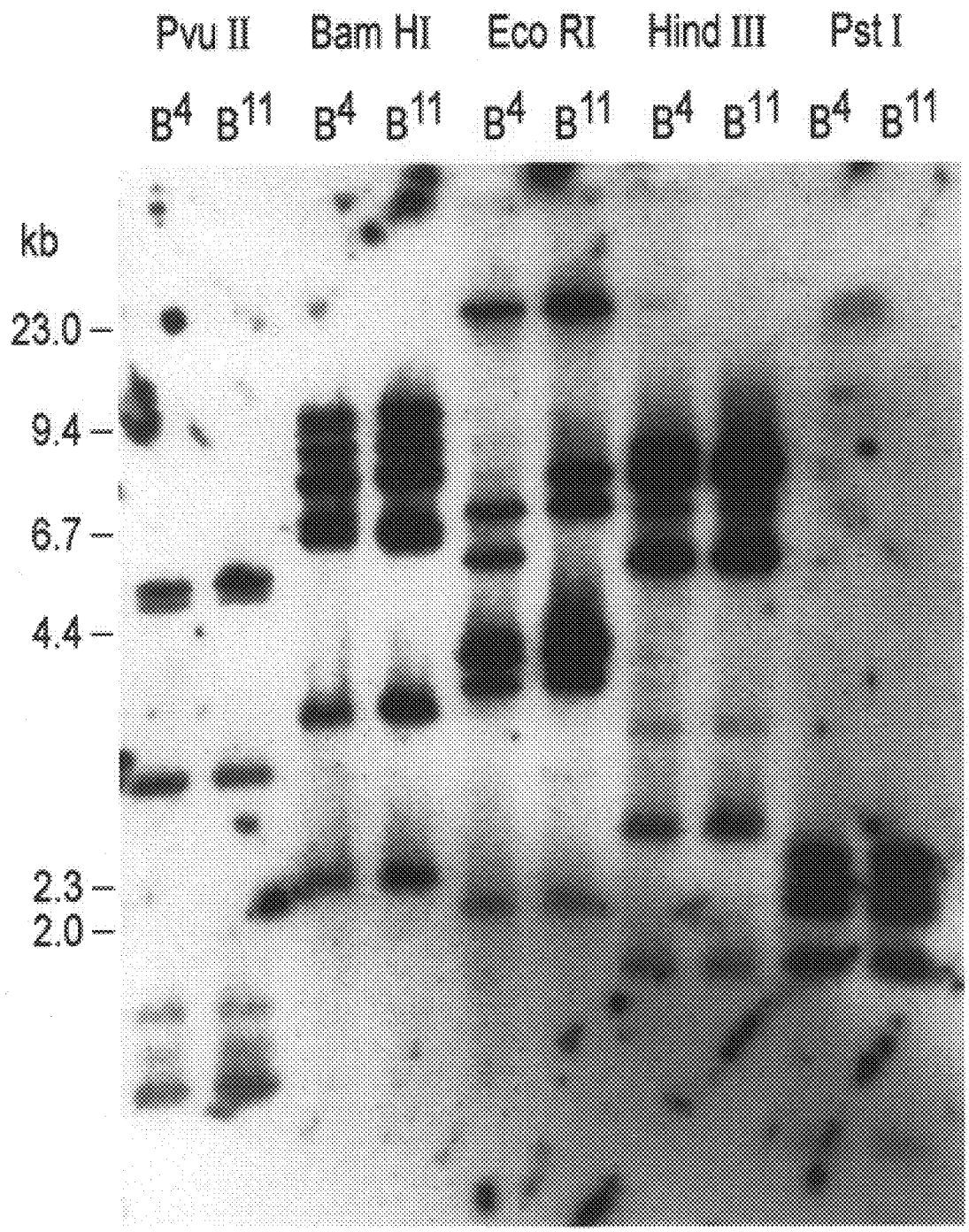

FIG. 10. Hybridization of the bg28 probe to genomic DNA (5 μg each lane) from birds of $\underline{B}^{4}$ and $\underline{B}^{11}$ haplotypes digested with Pvu II, Bam HI, Eco RI, Hind III and Pst I. On the left are molecular size markers (in kilobase pairs) based on a Hind II digestion of phage λ. The autoradiogram is the result of an overnight exposure.

FIG. 11. SEQ ID NO: 3 Nucleotide sequence of bg32.1

FIG. 12. SEQ ID NO: 4 Nucleotide sequence of bg11.

FIG. 13. SEQ ID NO: 5 Nucleotide sequence of bg14.

FIG. 14. SEQ ID NO: 6 Nucleotide sequence of bg3.

FIG. 15. SEQ ID NO: 7 Nucleotide sequence of bg8.

FIG. 16. SEQ ID NO: 8 Nucleotide sequence of bg17.

FIG. 17. SEQ ID NO: 9 Nucleotide sequence of gi6.

FIG. 18. SEQ ID NO: 10 Nucleotide sequence of gi9.

FIG. 19. SEQ ID NO: 11 Nucleotide sequence of gi11.

FIG. 20. SEQ ID NO: 12 Nucleotide sequence of a 4.757 Kb fragment of chicken genomic DNA to which all the cDNA clones will hybridize under stringent conditions (in overnight. aqueous solution hybridizations at 65° C. in 5×SSPE, 5×Denhardt's, 1% SDS, 100 ug/ml salmon sperm DNA, $^{32}$P-labeled denatured probe, followed by a 65° C. stringent washrin 0.5×SSC).

FIG. 21. Percent similarity among the bg CDNA clone sequences as exemplified by comparison of all clones to bg14 using the ALIGN program in the DNASTAR.

FIG. 22. SEQ ID NOS: 13–15 Comparison of the peptide sequence of two B-G 21 peptides with the predicted amino acid sequences of bg14 and bg11 CDNA clones.

Figure 23:
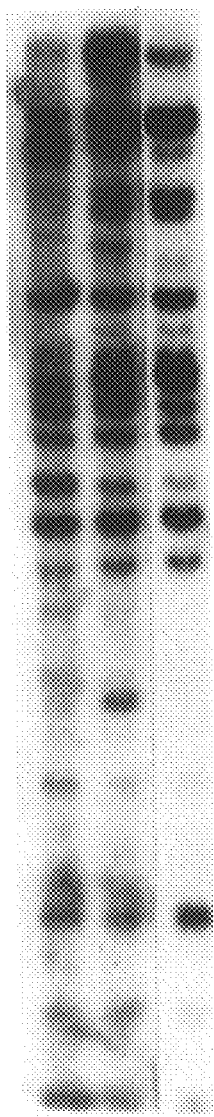

FIG. 23. Hybridization of the bg11 probe to restriction digests of turkey genomic DNA from three inbred lines. Sst 1-digested DNA samples (10 ug each sample) were subjected to electrophoresis; in an 0.8% agarose gel, alkaline transferred by positive pressure displacement into a hybridization membrane (NEN Gene Screen), baked for 1 hour at 80° C., briefly UV cross-linked. Hybridization was carried out at 60° C. in aqueous solution overnight (5×SSPE, 5×Denhardt's, 1% SDS, 100 ug/ml salmon sperm DNA, $^{32}$P-labeled denatured probe). Wash conditions were as follows: (a) a room temperature wash for 5 min. in 2×SSC (sodium chloride/sodium citrate), (b) followed by 60° C. stringent temperature wash for 30 min. in 0.5×SSC +1% SDS (sodium dodecy:L sulfate) and (c) a second room temperature wash for 5 min. in 2×SSC to remove the SDS before an overnight exposure of film to the membrane.

Figure 24:
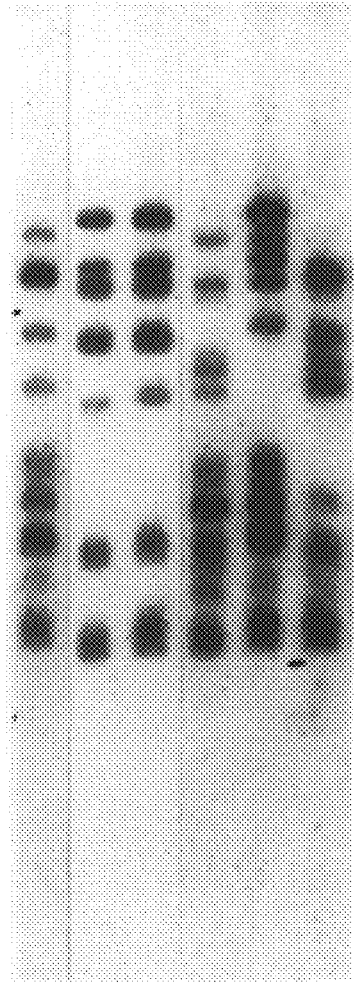

FIG. 24. Hybridization of the bg32.1 probe to restriction digests of pheasant DNA samples (10 ug each digested with Pvu II) from a family of pheasants (dam, sire and four progeny) in which $\underline{B}$ haplotypes have been defined by serological methods. Conditions of hybridization and washing are identical to those provided in FIG. 22.

FIG. 25. SEQ ID NO: 16 Sequence of a complete B-G gene. Included is a portion of the DNA upstream from the transcription start site.

DETAILED DESCRIPTION OF THE INVENTION

Pursuant to this invention, probes are provided by cloning of CDNA fragments from genes found within the B-G subregion of the MHC of a domesticated fowl, e.g., a chicken. With these probes, the presence of multiple alleles within the B-G subregion, a subregion of the $\underline{B}$ region encompassing multiple B-G loci, is demonstrated through homologous DNA hybridization of the B-G gene sequences in genomic DNA cut with a restriction enzyme, electrophoresed and analyzed in a Southern hybridization carried out either directly in the agarose matrix of the electrophoretic gel or in hybridization-membranes into which the DNA has been transferred. RFLP patterns which appear to be typical for each of a plurality of B-G alleles are described. Probes subsumed by the invention including synthetic oligonucleotide probes synthesized based on the sequences of the B-G CDNA clones described herein provide a new means of haplotyping chickens and other domesticated fowl including poultry (principally in the Order Galliformes) and game birds (principally in the Orders Anseriformes and Galliformes).

In one embodiment of the invention, a CDNA clone bg28 for a B-G antigen of the chicken major histocompatibility complex (MHC) was isolated by screening of a lambda gtll CDNA library constructed from chicken embryo erythroid cell poly((A$^{+}$) RNA. The identity of the cDNA clone as one encoding a B-G antigen was confirmed (1) by demonstrating that the clone is complementary to an erythroid cell-specific messenger RNA, (2) by obtaining the predicted patterns of hybridization of the clone with restriction endonuclease digested genomic DNA from inbred, MHC recombinant and polysomic chicken lines, and (3) by demonstrating the specific reactivity of antibodies monospecific for the fusion protein of this clone with B-G antigen protein.

Screening of the lambda gt11 cDNA library. A previously described lambda gt11 library,1/ the M library prepared from gradient-fractionated poly (A)$^{+}$ erythroid cell RNA was screened essentially as described previously.2/ Overnight cultures of E. coli strain Y10883/ were infected with 50,000 plaque-forming units of recombinant lambda gt11, suspended in top agarose, and plated on 150 mm TYE-plates. Two plates were prepared for each of five aliquots of the amplified M library. The rabbit antiserum prepared against purified B-G21 was preabsorbed by the addition of 4 mg/ml ovalbumin, and by mixing 250 µl of the antiserum with Y1088 cells from a 10 ml overnight culture, spun down and resuspended in 10 ml of G buffer (TBS containing 0.1% gelatin). After 30 minutes incubation on ice, the cells were spun out and the antibody containing solution was then poured onto the surface of a 150 mm plate containing confluently lysed Y1088 cells infected with wild type lambda gt11. After an additional 30 minutes incubation on this plate (with rocking), the antibody containing solution was collected and the debris removed by centrifugation. It was then diluted to a final volume of 125 ml with GT and added to the filters. The additional steps in screening are as previously described (Moon, et al., 1985). Approximately 100 plaques were found to react positively with the rabbit anti-β-G21 serum. Thirty of these were picked for a second screening, the majority of which were again positive on the second screening. From these, six clones of varying intensity of reactivity with the antiserum were picked for further study. Three of these were subcloned.

1/ See Moon, et al., *J.Cell Biol.* 100:152–160 (1985).
2/ See Young, et al., *Proc.Nat.Acad.Sci.* 80:1194–1198 (1983).
3/ See Young, et al., *Science* 222:778–782 (1983).

Subcloning lambda qt11 inserts into M13 and Bluescript. cDNA inserts were obtained from recombinant clones of lambda gt11 by digestion with <u>EcoR1</u>. Insertion into the M13 and Bluescript (Stratagene) vectors was carried out by mixing the digested recombinant clones with the new vector in a ratio of 3:1 and religating. Recombinant colonies were selected using X-gal plates. The subclone with the longest insert 0.5 kb in size, designated bg28, was selected for further analysis.

Antiserum 7 used in identifying those clones was prepared against purified B-G21 antigen and was demonstrated to be specific for B-G antigens and for bg28 fusion protein in Western blot preparations. The presence of antibodies within this antiserum which recognize epitopes shared by the fusion protein product and B-G21 protein was also demonstrated. Antibodies affinity-purified with the bg28 lysogen lysate were found to bind to B-G21 antigen in immunoblots. See FIG. 1.

Preparation of fusion protein B-G28. *E. coli* strain Y1089 (supF)4/ were infected with the lambda gt11 recombinant clones, colonies replica plated and lysogens selected as previously described.5/ One lysogen, grown up in an overnight culture, was inoculated into 25 ml TYE media and incubated at 32° C. to an $OD_{600}$ of 0.6. The cells were then heat shocked at 42° C. for 20 minutes, IPTG added to a final concentration of 10 mM, and incubation continued at 37° C. for two hours. Parallel cultures of the lambda gt11 wild type and an uninduced culture of the lysogen were prepared to serve as controls. The cultures were harvested by pelleting the cells, resuspending in PBS and 0.1% phenyl methyl sulfonyl fluoride (PMSF). The cells were lysed by sonication, the cellular debris removed by centrifugation, and the resulting supernatants were used as a, source of the bg28 fusion protein.

4 See Young, et al., *Science* 222:778–782 (1983).
5 See Cox et al., *J.Cell Biol.* 100:1548–1557 (1985).

Figure 2A:
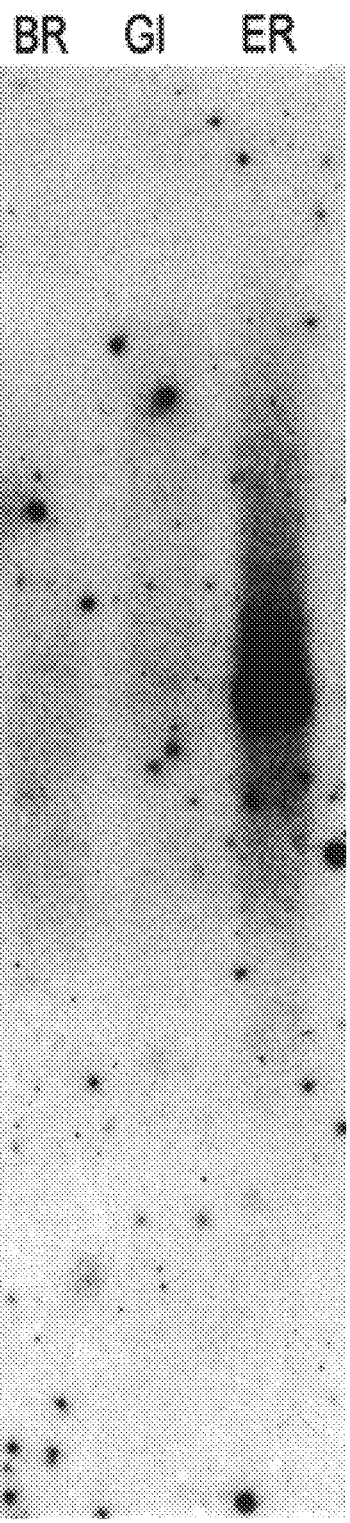
Figure 2B:
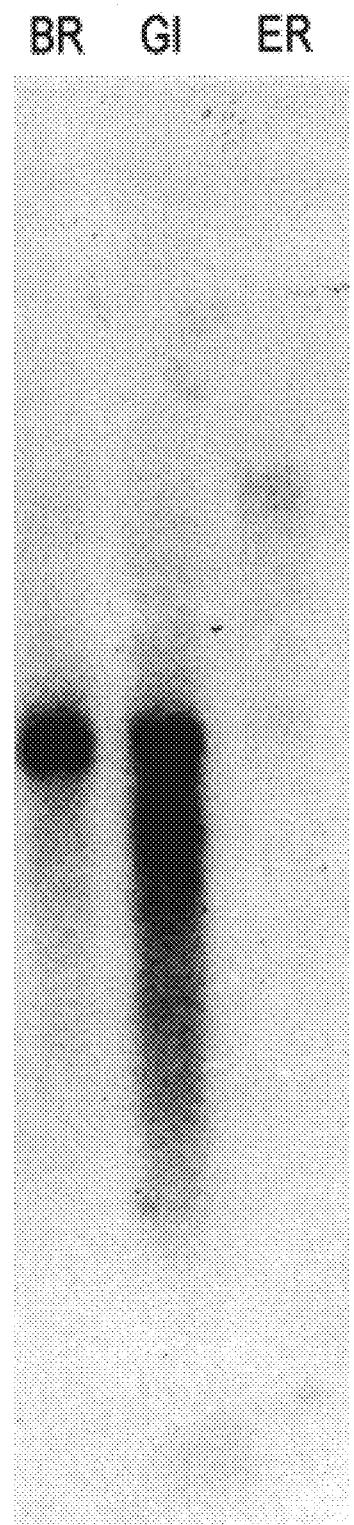

Hybridization of bq28 cDNA insert to transcripts from erythroid and nonerythroid cells. Poly(A)+ RNA was isolated from different tissues of 14-day chick embryos. The RNA samples were subjected to denaturing agarose gel electrophoresis, capillary blotted into hybridization membranes and hybridized with $^{32}$P-labeled bg28 cDNA insert. Only for the erythroid cells, the only cells known to carry B-G antigen, was a hybridizing MRNA species found (FIG. 2A). The lack of hybridization seen for other tissues were not due to RNA degradation since the same samples were shown to hybridize to a β-actin probe in a parallel hybridization experiment (FIG. 2B). Bursa poly(A)+ RNA was similarly analyzed with both probes and was found to hybridize to only the β-actin probe (data not shown). The size of the erythroid mRNA that hybridized to the bg28 insert was 2.1 kb, which is sufficiently long to encode a protein of 48 kDa.

Hybridization of bg28 to genomic DNA from chickens differing at the B system loci. Additional evidence for the identity of bg28 as a cDNA clone from the B-G region of the chicken MHC are provided by the patterns of hybridization of this clone to restriction endonuclease-digested genomic DNA from chickens differing in MHC haplotype, as shown in Table 1.

TABLE 1

Sources of Blood Samples Used in Southern Analyses

| B Haplo-type[1] | B-G Allele | Line | FIGURE | Source |
|---|---|---|---|---|
| $B^{15}$ | $B-G^{15}$ | diploid | 3 | Cornell[a] |
| $B^{15}$ | $B-G^{15}$ | trisomic | 3 | Cornell[a] |
| $B^{15}$ | $B-G^{15}$ | tetrasomic | 3 | Cornell[a] |
| $B^{4}$ | $B-G^{4}$ | CC | 4 | Basel[b] |
| $B^{12}$ | $B-G^{12}$ | CB | 4 | Basel[b] |
| $B^{17}$ | $B-G^{17}$ | UCD-003 | 4 | Davis[c] |
| $B^{18}$ | $B-G^{18}$ | UCD-253 | 4 | Davis[c] |
| $B^{19}$ | $B-G^{19}$ | UCD-235 | 4 | Davis[c] |
| $B^{23}$ | $B-G^{23}$ | UNH-105 | 4 | DeKalb[d] |
| $B^{24}$ | $B-G^{24}$ | UNH-105 | 4 | DeKalb[d] |
| $B^{Q}$ | $B-G^{Q}$ | UCD-001 | 4 | Davis[c] |
| $B^{15}$ | $B-G^{15}$ | UCD-315 | 5 | Davis[c] |
| $B^{15r1}$ | $B-G^{21}$ | — | 5 | Basel[e] |
| $B^{21}$ | $B-G^{21}$ | UCD-330 | 5 | Davis[c] |
| $B^{21r3}$ | $B-G^{15}$ | — | 5 | Basel[e] |

[1]Assignment of haplotype based on Chicken MHC Nomenclature Workshop; see Briles, et al., Immunogenetics 15: 441–447 (1982).
[a]Bloom, et al., J. Heredity 76:146–154 (1985).
[b]Hasek, et al., Folia biol. (Praha), 12: 335–341 (1966).
[c]Abplanalp, Inbred lines as genetic resources of chickens. Proceedings of the Third World Congress of Genetics Applied to Livestock Production, Lincoln, Nebraska, Vol. X, pp. 257–268 (1986).
[d]Briles, et al., Immunogenetics 15: 449–452 (1982).
[e]Koch, et al., Tissue Antigens 21: 129–137 (1983).

A first line of evidence supporting the designation of bg28 as a MHC clone was obtained by the analysis of genomic DNA from disomic, trisomic and tetrasomic chickens of $\underline{B}^{15}$ haplotype. The recent demonstration of a linkage between the major histocompatibility ($\underline{B}$) complex and the nucleolar organizer on a microchromosome in the chicken6/ has made it possible to select polysomics of a single haplotype. As would be expected if the bg28 clone were an MHC element, an increasing intensity of hybridization was obtained between the probe genomic DNA prepared from diploid, trisomic and tetrasomic birds. See FIG. 3, three samples on left. In contrast, hybridization of an actin probe is uniform across the three samples. See FIG. 3, three samples on right.

In the second set of Southern hybridizations, bg28 was hybridized with PvuII-digested DNA from eight lines of chickens differing at the MHC (see FIG. 4), restriction fragment length polymorphisms would be predicted if the clone is indeed from this region of the chicken genome. Antigens of the chicken MHC have been demonstrated previously to be polymorphic both immunologically7/ and biochemically. A polymorphic pattern of restriction fragment lengths is evident when bg28 is used as a probe.

The third line of evidence from genomic DNA studies for the designation of bg28 as a chicken MHC clone, and for its identity with the B-G subregion is provided by the pattern of hybridization of this clone with DNA from MHC recombinant haplotypes. Substantially reciprocal recombinants, designated as $\underline{B}^{15r1}$ and $\underline{B}_{21r3}$ which are $\underline{B\text{-}G}^{21}\text{-}\underline{B\text{-}F}^{15}$ and $\underline{B\text{-}G}^{15}\text{-}\underline{B\text{-}F}^{21}$, respectively, provide a means of further testing the bg28 clone for assignment to the B-G subregion. As would be predicted, the restriction fragment length pattern of hybridization of this probe with both recombinants produces a pattern indicating that the B-G subregion is that which has been cloned. See FIG. 5.

6/ See Bloom, et al., *J. Heredity* 76:146–154 (1985).
7/ See Briles, et al., *Immunogenetics* 15:441–447 (1982).

Sequence of the bg28 and comparison of the amino acid composition translated sequence with the amino acid composition of purified protein. bg28 was subcloned into M13mp19 and the entire insert sequenced in one direction by the dideoxy-chain-termination method. Translation of this nucleotide sequence and its complement into peptide sequence in all six reading frames produced only one peptide without internal stop codons. See FIGS. 6 and 7. Two nucleotide sequences of bg28 are presented. The first determination was made by sequencing only one strand of the cloned fragment, and the second was a full sequence determination on both strands;. The two sequences determinations are 99% identical. The differences between the first and second determinations are minor, they consist of: (1) a change from G>C at position 72, (2) the deletion of ATC at positions 258–260, (3) the deletion of A at position 354, (4) the insertion of A at position 490, and (5) the transposition of GC to CG at positions 506–507. The differences are of such a minor nature that probes of either sequence would provide identical RFLP patterns in Southern hybridizations. As Table 2 shows, the amino acid composition of this peptide (genotype unknown) compares well with the amino acid composition of the B-G21.

TABLE 2

Amino Acid Composition Comparison

|  | B-G21 antigen | Translated bg28 | Ratio |
|---|---|---|---|
| Ala | 41 | 11 | 3.7 |
| Cys | 6 | 5 | 1.2 |
| Phe | 37 | 13 | 2.85 |
| His | 12 | 4 | 3 |
| Ile | 17 | 10 | 1.7 |
| Lys | 48 | 8 | 4.2 |

TABLE 2-continued

Amino Acid Composition Comparison

|  | B-G21 antigen | Translated bg28 | Ratio |
|---|---|---|---|
| Leu | 48 | 15 | 3.2 |
| Met | 8 | 2 | 4 |
| Asx (Asn or Asp) | 39 | 14 | 2.8 |
| Pro | 17 | 1 | 17 |
| Glx (Gln or Glu) | 70 | 21 | 3.3 |
| Arg | 31 | 18 | 1.7 |
| Ser | 24 | 17 | 2.1 |
| Thr | 19 | 7 | 2.7 |
| Val | 30 | 17 | 1.8 |
| Trp | — | 3 | — |
| Tyr | 13 | 5 | 2.6 |
| TOTAL | 431 | 167 | 2.6 |

A second cDNA probe useful in this invention and identified as bg32.1 was also subcloned into Blue-script and purified from the vector prior to labeling by random priming.

The bg32.1 is a 650 bp cDNA clone isolated from a lambda gt11 expression library made erythroid from erythrocyte mRNA8/ by cross-hybridization with bg32, a clone originally obtained screening the same library with antibodies prepared against purified B-G 21 antigen as described above. Under conditions of high stringency, the bg32 and bg32.1 fragments fail to hybridize with the previously described bg28 clone. However, as demonstrated previously with bg28, the bg32.1 clone can be assigned to $\underline{B}$ system-bearing microchromosome and further assigned to the $\underline{B\text{-}G}$ subregion on the basis of the patterns of hybridization with DNA from birds polysomic for the $\underline{B}$ system bearing microchromosome and with DNA from MHC. recombinant haplotypes (FIG. 8). The intensity of hybridization of the bg32.1 probe to the DNA of polysomic birds increases proportionate to the copy number of the $\underline{B}$ system bearing microchromosome. The bg32.1 probe can be further assigned to the $\underline{B\text{-}G}$ subregion on the basis of the pattern of hybridization with DNA from $\underline{B}$ system recombinants derived from two independent recombinant events which produced essentially reciprocal rearrangements of the B-F/B-L and B-G subregions in $\underline{B}^{15}$ and $\underline{B}^{21}$ haplotypes. The pattern of hybridization with DNA of the recombinants matches that of the $\underline{B\text{-}G}$ subregion contributing parental haplotype (FIG. 8). The nucleotide sequence of λbg32.1 is shown by FIG. 11.

8/ Moon, R. T., et al., *J. Cell Biol.* 100:152–160 (1985).

High molecular weight DNA was isolated from blood samples collected from birds of known $\underline{B}$ system haplotype carried in several different flocks (see Table 3).

TABLE 3

B-G Genotypes Analyzed

| B-G Allele | B Haplo-Type | Line | Status | FIG.(S) Illustrating | Sample Size | Source |
|---|---|---|---|---|---|---|
| B-G$^2$ | B$^2$ | RPRL-15.7-2* | C+ | 2 | 3 | East Lansing# |
| B-G$^2$ | B$^2$ | RPRL-15.6-2 | I,C | — | 3 | East Lansing |
| B-G$^2$ | B$^2$ | UCD-331 | I,C | — | 3 | Davis |
| B-G$^2$ | B$^2$ | Reference Stock | S | — | 1 | DeKalb |
| B-G$^3$ | B$^3$ | UCD-313 | I,C | 2 | 2 | Davis |
| B-G$^4$ | B$^4$ | PR-CC* | I,C | 2,3 | 1 | Basel |
| B-G$^5$ | B$^5$ | RPRL-15.151-5* | I | 2 | 2 | East Lansing |

TABLE 3-continued

B-G Genotypes Analyzed

| B-G Allele | B Haplo-Type | Line | Status | FIG.(S) Illustrating | Sample Size | Source |
|---|---|---|---|---|---|---|
| $B\text{-}G^6$ | $B^6$ | G-B2* | I | 2 | 1 | Athens |
| $B\text{-}G^{10}$ | $B^{10}$ | Reference Stock* | S | 2 | 2 | DeKalb |
| $B\text{-}G^{11}$ | $B^{11}$ | Wis 3* | S | 2,3 | 2 | DeKalb |
| $B\text{-}G^{12}$ | $B^{12}$ | PR-CB* | I,C | 2 | 1 | Basel |
| $B\text{-}G^{12}$ | $B^{12}$ | RPRL 15.C-12 | I,C | — | 2 | East Lansing |
| $B\text{-}G^{13}$ | $B^{13}$ | G-B1* | I | 2 | 1 | Athens |
| $B\text{-}G^{13}$ | $B^{13}$ | RPRL 15.p-13 | I,C | — | 2 | East Lansing |
| $B\text{-}G^{14}$ | $B^{14}$ | UCD-316 | I,C | 2 | 2 | Davis |
| $B\text{-}G^{15}$ | $B^{15}$ | RPRL-$151_5$-15* | I,C | 2 | 2 | East Lansing |
| $B\text{-}G^{15}$ | $B^{15}$ | Polysomic | S | 1 | 9 | Ithaca |
| $B\text{-}G^{15}$ | $B^{15}$ | UCD-254 | I,C | 4 | 2 | Davis |
| $B\text{-}G^{15}$ | $B^{15}$ | UCD-011 | I | — | 2 | Davis |
| $B\text{-}G^{15}$ | $B^{15}$ | UCD-057 | I | — | 2 | Davis |
| $B\text{-}G^{15}$ | $B^{15}$ | UCD-035 | I | — | 1 | Davis |
| $B\text{-}G^{15}$ | $B^{21r3}$, | $R^5$, UCD-386 | I,R | — | 2 | Basel/Davis |
| $B\text{-}G^{15}$ | $B^{15}$ | UCD-396(BN) | I | — | 1 | Davis |
| $B\text{-}G^{17}$ | $B^{17}$ | UCD-003* | I,C | 2,4 | 4 | Davis |
| $B\text{-}G^{18}$ | $B^{18}$ | UCD-253* | I,C | 2 | 2 | Davis |
| $B\text{-}G^{19}$ | $B^{19}$ | RPRL.15.P-19* | I,C | 2 | 2 | East Lansing |
| $B\text{-}G^{19}$ | $B^{19}$ | UCD-335 | I,C | 2 | 2 | Davis |
| $B\text{-}G^{21}$ | $B^{21}$ | RPRL.15N-21* | I,C | 2 | 3 | East Lansing |
| $B\text{-}G^{21}$ | $B^{21}$ | UCD-330 | I,C | 1 | >20 | Davis |
| $B\text{-}G^{21}$ | $B^{21}$ | UCD-100 (Australorp) | I | — | 5 | Davis |
| $B\text{-}G^{21}$ | $B^{21}$ | Ref. Stock | S | — | 1 | DeKalb |
| $B\text{-}G^{21}$ | $B^{15r1}$ | $R^4$, UCD-387 | I,R | 1 | 2 | Basel/Davis |
| $B\text{-}G^{23}$ | $B^{23}$ | UNH-105* | S | 2 | 1 | DeKalb |
| $B\text{-}G^{24}$ | $B^{24}$ | UNH-105* | S | 2 | 1 | DeKalb |
| $B\text{-}G^{24}$ | $B^{24}$ | UCD-312 | I | — | 1 | Davis |
| $B\text{-}G^C$ | $B^C$ | UCD-342 (Ceylonese X Red Jungle Fowl) | I,C | — | 1 | Davis |
| $B\text{-}G^J$ | $B^J$ | UCD-333 (Red Jungle Fowl) | I | — | 1 | Davis |
| $B\text{-}G^O$ | $B^O$ | UCD-104 | I,C | — | 1 | Davis |
| $B\text{-}G^Q$ | $B^Q$ | UCD-336 (Red Jungle Fowl) | I | — | 1 | Davis |

*Reference lines used as the type population in standardizing the B system nomenclature (see Briles et al., Immunogenetics 15:441–447 (1982)), although the RPRL samples are now represented by congenic lines.

Samples were taken from one or more individuals of each flock examined. FIGS. 9A and 9B depict patterns of hybridization between bg28 and bg32.1 and Pvu II digested DNA from a single representative from each of the 17 standard haplotypes examined. Multiple DNA restriction fragments, 4–10 per haplotype ranging size from approximately 1 to about 10 Kb are detected by the two probes. Some fragments are common to the patterns produced by both probes. For example, the three largest fragments in the B-G$^{21}$ patterns produced with both probes appear identical. Other fragments are detected only by one or the other of the probes. A number of the restriction fragments appear to be widely shared among the haplotypes, although with the exception of perhaps one fragment of about 5.2 Kb present in Pvu II-digested DNA probed with bg28, none are shared in common across all the haplotypes examined. The B-G subregions are each so different, as reflected in the restriction fragment patterns, that generally the different genotypes can be distinguished readily from each other in a Southern hybridization using this single restriction enzyme and either of the two B-G c-DNA probes. The only exceptions appear to be the patterns produced by DNA from birds of B$^4$ and B$^{11}$ haplotypes. The other important finding is that without exception the restriction fragment patterns were the same for each B-G allele across the samples included in this study including samples obtained from different populations known on the basis of serological typing to carry the same B haplotypes.

In order to distinguish clearly the B-G genotype of B$^4$ and B$^{11}$ birds, it was necessary to employ additional restriction enzymes. Among the digestions with five restriction enzymes only those produced with Eco RI provided patterns clearly differentiating the two B-G genotypes (FIG. 10). It is notable that even with this enzyme the patterns of the two haplotypes differ only by a proportionate shift in the size of two restriction fragments out of the seven fragments produced.

Additional cDNA probes derived from erythrocytic mRNA of B$^{21}$ haplotype useful in this invention and identified as bg11 (FIG. 12), bg14 (FIG. 13), bg3 (FIG. 14), bg8 (FIG. 15) and bg17 (FIG. 16), as well as the additional clones gi6 (FIG. 17), gi9 (FIG. 18) and gi11 (FIG. 19) derived from mRNA of the small intestine (also B$^{21}$) were also subcloned into Bluescript, fully sequenced and found to have properties like those of bg28 and bg32.1 when employed in the Southern hybridizations. The strong sequence similarity among all the cDNA clones is depicted in FIG. 20 where all the cDNA clone sequences are compared to bg14 (a full length cDNA clone having no intronic sequences) using the ALIGN program in DNASTAR. (ALIGN is an algorithm for optimal local alignment of two partially homologous DNA sequences.) These sequences, encompassing full-length (also including introns in some), near the full-length or partial lengths of transcripts for individual B-G polypeptides, all show significant sequence similarity with bg14. Moreover, bg14 shows significant similarity to the nucleotide sequence of a 4.757 Kb fragment of chicken genomic DNA, typifying a segment of genomic DNA to which these B-G cDNA clones would hybridize will hybridize under straight conditions. Using the SEQCOMP program in DNASTAR (an algorithm appropriate for alignment with very large sequences in a reasonable length of time by time locating regions of perfect match and then optimizing fit) sequences the similarity between the two sequences is 89%.

Analysis of these sequences have provided an understanding of the organization of the B-G transcripts and prediction of the amino acid sequence of the B-G polypeptides. For purposes of illustration the organization of bg14 is described. The fully processed transcript cloned in bg14 is 1816 bp. It contains both 5'- and 3'-noncoding sequences. An open reading frame corresponds to a 398 amino acid polypeptide (including signal peptide) with calculated $M_r$ 45,298. Within the coding region there are sequences for: (a) a N-terminal signal peptide of 34 amino acids, (b) a single extracellular domain (amino acid residues 35–148), (c) a transmembrane domain (residues 149–178), and (d) a cytoplasmic region made up from a series of domains (residues 179–398). The single extracellular domain has properties that identify as highly similar to members of the immunoglobulin gene superfamily. The intracellular domains are characterized by a strong heptad pattern, repeats of seven amino acids the seventh residue of which is nearly always hydrophobic. This pattern is consistent with the primary sequence patterns of molecules β-alpha helical coiled coil conformation. All the cDNA clones are similarly organized. Some are missing portions of the full transcript sequence (for example bg17 is missing a portion of the 5' end and bg11 is missing a small portion at the 3' end) and some contain unprocessed introns (bg8, for example, possesses 9 unprocessed introns; bg11 contains 1). Comparisons of the sequences bg28 and bg32.1 with the sequences of clones full transcripts provide evidence that these probes encompass respectively portions of the 5' end and 3' end of B-G transcripts.

Since none of the transcripts represented in the sequences of these clones are identical, except for bg14 and bg8 which apparently represent the same transcript type and differ only by the presence of intronic sequences with bg8 and a single, silent base difference, there is now evidence for the expression of 8 transcript types. Six of these are from libraries of $B^{21}$ haplotype and the remaining two, bg28 and bg32.1 are from birds of unknown genetic background. Hence the multiple transcript types provide evidence for the expression of alleles are multiple loci within the B-G subregion. Probes derived from these cDNA clones hybridize under stringent conditions (e.g., overnight aqueous hybridization in 5×SSPE, 5×Denhardt's, 1% SDS, 100 ug/ml salmon sperm DNA, $^{32}$P-labeled denatured probe at 65° C. and stringent temperature wash at 65° C. in 0.5×SSC) to multiple bands in Southern hybridizations with genomic DNA from chickens of many different haplotypes, as illustrated by FIGS. 3, 4, 5, 9 (A and B), and 10. Hybridization temperatures and wash temperatures of from about 55° C. to about 70° C. are appropriate.

These sequences and subsequences derived from them for the production of synthetic oligonucleotide probes have the capability for producing RFLP patterns by hybridization with gene sequences in other bird species. Illustrated in FIG. 23 is the hybridization of bg11 under moderately high stringency (overnight aqueous hybridization in 5×SSPE, 5×Denhardt's, 1% SDS, 100 ug/ml salmon sperm DNA, $^{32}$P-labeled denatured probe at 60° C. and stringent temperature wash at 60° C. in 0.5×SSC) and produces polymorphic band patterns with Sst 1 digested genomic from turkeys.

The capability of these probes to produce RFLP patterns in genomic DNA of other bird species is further illustrated by FIG. 24 where bg32.1 hybridizes to multiple, polymorphic bands in genomic DNA from a family of ring-necked pheasants serologically B typed.

I claim:

1. A process for determining the haplotype of a fowl of the order Galliformes or the order Anseriformes which comprises:
   (i) providing a sample of DNA from said fowl;
   (ii) cleaving said sample of DNA with a restriction enzyme to provide cleavage reaction products;
   (iii) fractionating said cleavage reaction products;
   (iv) subjecting said cleavage reaction products to electrophoresis on a gel to produce a pattern of said cleavage reaction products on said gel;
   (v) hybridizing a probe complementary to the B-G sub-region of the major histocompatibility complex of said fowl to said cleavage reaction products;
   (vi) detecting the pattern produced by said hybridized cleavage reaction products, and
   (vii) comparing said pattern with a pattern which results from the hybridization of said probe with the cleavage reaction products produced by the DNA of a fowl having a known B region haplotype.

2. A process as defined by claim 1 in which said fowl is a chicken.

3. A process as defined by claim 1 in which said fowl is a turkey.

4. A process as defined by claim 1 in which said fowl is a pheasant.

* * * * *